US011180806B2

(12) United States Patent
Davin et al.

(10) Patent No.: US 11,180,806 B2
(45) Date of Patent: *Nov. 23, 2021

(54) PROCESS AND KIT FOR DETERMINING IN VITRO THE IMMUNE STATUS OF AN INDIVIDUAL

(71) Applicants: BIOMERIEUX, Marcy l'Etoile (FR); HOSPICES CIVILS DE LYON (HCL), Lyons (FR)

(72) Inventors: Fanny Davin, Saint Jean de Muzols (FR); Alain Lepape, Saint-Genis Laval (FR); Guillaume Monneret, Lyons (FR); Florence Frager, Lyons (FR)

(73) Assignees: BIOMERIEUX, Marcy l'Etoile (FR); HOSPICES CIVILS DE LYON (HCL), Lyons (FR)

( * ) Notice: Subject to any disclaimer, the term of this patent is extended or adjusted under 35 U.S.C. 154(b) by 347 days.

This patent is subject to a terminal disclaimer.

(21) Appl. No.: 15/960,966

(22) Filed: Apr. 24, 2018

(65) Prior Publication Data

US 2018/0312921 A1 Nov. 1, 2018

Related U.S. Application Data

(63) Continuation of application No. 13/978,827, filed as application No. PCT/FR2012/050172 on Jan. 27, 2012, now Pat. No. 9,982,298.

(30) Foreign Application Priority Data

Jan. 27, 2011 (FR) ...................................... 1150646

(51) Int. Cl.
 *C40B 30/04* (2006.01)
 *C12Q 1/6876* (2018.01)
 (Continued)

(52) U.S. Cl.
 CPC ......... *C12Q 1/6876* (2013.01); *C12Q 1/6883* (2013.01); *G01N 33/68* (2013.01);
 (Continued)

(58) Field of Classification Search
 None
 See application file for complete search history.

(56) References Cited

U.S. PATENT DOCUMENTS

| 2003/0228617 | A1 | 12/2003 | Aune et al. |
| 2004/0014059 | A1* | 1/2004 | Liew ................... C12Q 1/6886 |
| | | | 435/6.16 |
| 2005/0196764 | A1 | 9/2005 | Liew |

FOREIGN PATENT DOCUMENTS

| FR | 2855832 A1 | 12/2004 |
| WO | 94/12670 A2 | 6/1994 |

(Continued)

OTHER PUBLICATIONS

Jul. 30, 2013 Written Opinion issued in PCT/FR2012/050172.
(Continued)

*Primary Examiner* — Christian C Boesen
(74) *Attorney, Agent, or Firm* — Oliff PLC

(57) ABSTRACT

The present invention relates to a process for determining in vitro the immune status of an individual according to which: (a) a blood sample from the individual is provided, (b) at least two reagents specific to at least two products of expression of at least two target genes are provided; (c) the expression of said at least two target genes is determined, and (d) the expression of said at least two target genes respectively is compared with a reference expression, with a change in the expression of said at least two target genes relative to their reference expression indicating that the individual's immune status has changed, and a correlation between the expression of said at least two target genes with their reference expression indicating that the individual's immune status is normal; as well as a kit for determining said immune status of the individual.

13 Claims, 56 Drawing Sheets

Specification includes a Sequence Listing.

(51) Int. Cl.
   *C12Q 1/6883* (2018.01)
   *G01N 33/68* (2006.01)
(52) U.S. Cl.
   CPC . *C12Q 2600/106* (2013.01); *C12Q 2600/158* (2013.01); *C40B 30/04* (2013.01)

(56) References Cited

FOREIGN PATENT DOCUMENTS

| WO | 03/084388 A2 | 10/2003 |
|---|---|---|
| WO | 2010/049818 A1 | 5/2010 |
| WO | 2010/082004 A1 | 7/2010 |

OTHER PUBLICATIONS

"GeneChip Human Genome Arrays," Internet Citation, [Online] 2004, XP002384937.
Grisanti, L.A., et al., "Pro-inflammatory responses in human monocytes are b1-adrenergic receptor subtype dependent," Molecular Immunology, vol. 47, No. 6, 2010, pp. 1244-1254.
Malcolm, Kenneth, et al., "Microarray analysis of lipopolysaccharide-treated human neutrophils," American Journal of Physiology Lung Cellular and molecular physiology, vol. 284, No. 4, 2003, pp.L663-L670.
Keel, Marius, et al., "Interleukin-10 counterregulates proinflammatory cytokine-induced inhibition of neutrophil apoptosis during severe sepsis," Blood, vol. 90, No. 9, 1997, pp. 3356-3363.
Bozza, Fernando A., et al., "Cytokine profiles as markers of disease severity in sepsis: a multiplex analysis," Critical Care vol. 11, No. 2, 2007, pp. 1-8.
Heper, Y., et al., "Evaluation of serum C-reactive protein, procalcitonin, tumor necrosis factor alpha, and interleukin-10 levels as diagnostic and prognostic parameters in patients with community-acquired sepsis, severe sepsis, and septic shock," European Journal of Clinical Microbiology & Infectious Diseases, vol. 25, No. 8, 2006, pp. 481-491.
Monneret, G., et al., "The anti-inflammatory response dominates after septic shock: association of low monocyte HLA-DR expression and high interleukin-10 concentration," Immunology Letters, vol. 95, No. 2, 2004, pp. 193-198.
Lee, Keun-Wook, et al., "Direct role of NF-[kappa]B activation in Toll-like receptor-triggered HLA-DRA expression," European Jounal of Immunology, vol. 36, No. 5, 2006, pp. 1254-1266.
Caille, Vincent, et al., "Histocompatibility leukocyte antigen-D related expression is specifically altered and predicts mortality in septic shock but not in other causes of shock," Shock, vol. 22, No. 6, 2004, pp. 521-526.
Payen, Didier, et al., "Gene profiling in human blood leucocytes during recovery from septic shock," Intensive Care medicine, vol. 34, No. 8, 2008, pp. 1371-1376.
Van Zoelen, M. A. D., et al., "Expression and Role of Myeloid-related Protein-14 in Clinical and Experimental Sepsis," American Journal of Respiratory and Critical Care Medicine, vol. 180, No. 11, 2009, pp. 1098-1106.
Vogl, T., et al., "Mrp8 and Mrp14 are endogenous activators of Toll-like receptor 4, promoting lethal, endotoxin-induced shock," Nature Medicine, vol. 13, No. 9, Sep. 2007, pp. 1042-1049.
Le Tulzo, Y., et al., "Monocyte Human Leukocyte Antigen-DR Transcriptional Downregulation by Cortisol during Septic Shock," American Journal of Respiratory and Critical Care Medicine, vol. 169, No. 10, 2004, pp. 1144-1151.
Wolk, K., et al., "Multiple Mechanisms of Reduced Major Histocompatibility Complex Class II Expression in Endotoxin Tolerance," Journal of Biological Chemistry, vol. 278, No. 20, May 2003, pp. 18030-18036.
Divanovic, Senad, et al., "Negative regulation of Toll-like receptor 4 signaling by the the Toll-like receptor homolog RP105," Nature Immunology, vol. 6, No. 6, 2005, pp. 571-578.
Ogata Hirotaka, et al., "The toll-like receptor protein RP105 regulates lipopolysaccharide signaling in B cells," The Journal of Experimental Medicine, vol. 192, No. 1, Jul. 3, 2000, pp. 23-29.
Deng, J. C., et al., "Sepsis-induced suppression of lung innate immunity is mediated by IRAK-M," Journal of Clinical Investigation, Sep. 2006, vol. 116, No. 9, pp. 2532-2542.
Van'T Veer, Cornelis, et al., "Induction of IRAK-M is associated with lipopolysaccharide tolerance in a human endotoxemia model," Journal of Immunology, vol. 179, No. 10, 2007, pp. 7110-7120.
Verstrepen, Lynn, et al., "Expression of the NF-[kappa]B inhibitor ABIN-3 in response to TNF and toll-like receptor 4 stimulation is itslelf regulated by NG-[kappa]B," Journal of Cellular and Molecular Medicine, vol. 12, No. 1, 2008, pp. 316-329.
Wullaert A., et al., "LIND/ABIN-3 is a Novel Lipopolysaccharide-inducible inhibitor of NF-(kappa)B Activation," Journal of Biological Chemistry, vol. 282, No. 1, Jan. 5, 2007, pp. 81-90.
Cazalis Marie-Angelique, et al., "Early modulated mRNA expression of endotoxin tolerance genes is observed at the onset of septic shock," Inflammation Research, vol. 59, No. Suppl. 1, 2010, pp. S128-S129.
Lubeseder-Martellato, C., et al., "Guanylate-Binding protein-1 expression is selectively induced by inflammatory cytokines and is an activation marker of endothelial cells during inflammatory diseases," American Journal of Pathology, vol. 161, No. 5, 2002, pp. 1749-1759.
Vermont, Clementien L., et al., "CC and CXC chemokine levels in children with meningococcal sepsis accurately predict mortality and disease severity," Critical Care, vol. 10, No. 1, 2006, p. R33.
D'Ambrosio, D., et al., "Chemokine receptors in inflammation: an overview," Journal of Immunological Methods, vol. 273, No. 1-2, 2003, pp. 3-13.
Cummings, C.J., et al., "Expression and function of the chemokine receptors CXCR1 and CXCR2 in sepsis," Journal of Immunology, vol. 162, No. 4, 1999, pp. 2341-2346.
Nakamura et al., "Treatment with polymyxin B-immobilized fiber reduces platelet activation in septic shock patients: decrease in plasma levels of soluble P-selectin, platelet factor 4 and beta-thromboglobulin," Inflammation Research, vol. 48, No. 4, 1999, pp. 171-175.
Punyadeera, Chamindie, et al., "A biomarker panel to discriminate between systemic inflammatory response syndrome and sepsis and sepsis severity," Journal of Emergencies, Trauma, and Shock, vol. 3, No. 1, Jan. 2010, pp. 26-35.
Cheron, Aurelie, et al., "Lack of recovery in monocyte human leukocyte antigen-DR expression is independently associated with the development of sepsis after major trauma," Critical Care, 2010, vol. 14, No. 6, pp. 1-10.
Kricka, Larry J., "Nucleic acid detection technologies—labels, strategies, and formats," Clinical Chemistry, 1999, vol. 45, No. 4, pp. 453-458.
Bustin, S. A., "Quantification of mRNA using real-time reverse transcription PCR (RT-PCR): trends and problems," Journal of Molecular Endocrinology, 2002, 29, pp. 23-39.
Giulietti, Annapaula, et al., "An overview of real-time quantitative PCR: applications to quantify cytokine gene expression," Methods, 2001, 25, pp. 386-401.
Nisonoff, A., et al., "Properties of the major component of a peptic digest of rabbit antibody," Science, vol. 132, 1960, pp. 1770-1771.
Skerra, A, "Bacterial expression of immunoglobulin fragments," Current Opinion in Immunology, 1993, No. 5, pp. 256-262.
Huston, James S., et al., "Protein engineering of antibody binding sites: Recovery of specific activity in an anti-digoxin single-chain Fv analogue produced in *Escherichia coli*," Proc. Natl. Acad. Sci. USA, vol. 85, Aug. 1988, pp. 5879-5883.
Kawai et al., J. Infect. Chemother., 1998; 4: pp. 121-127.

* cited by examiner

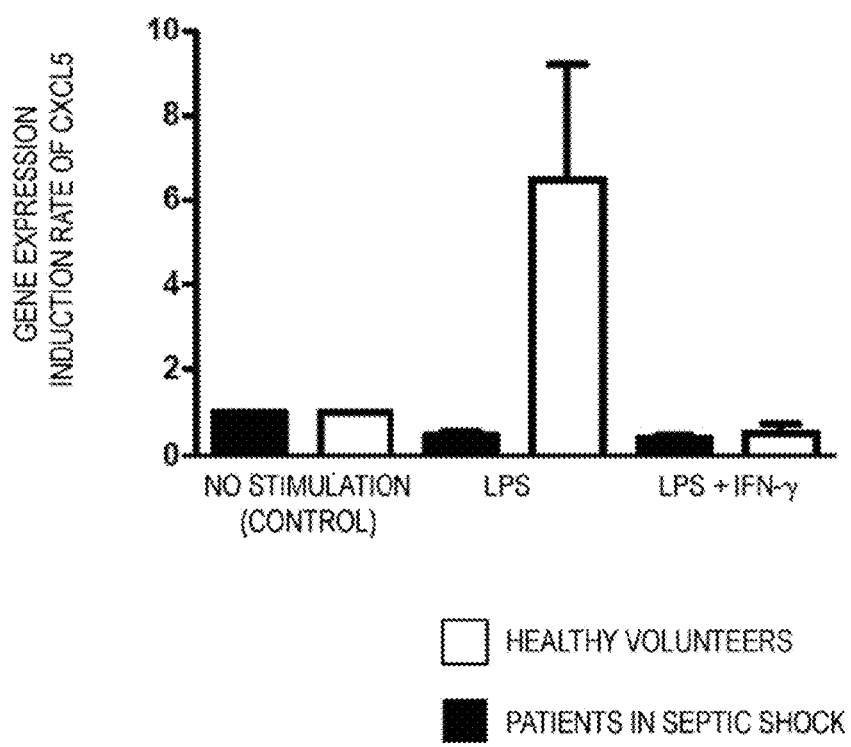

PROCESS AND KIT FOR DETERMINING IN VITRO THE IMMUNE STATUS OF AN INDIVIDUAL

This is a Continuation of application Ser. No. 13/978,827, filed Jul. 9, 2013, which in turn is a national stage of PCT/FR2012/050172, filed Jan. 27, 2012, which claims the benefit of FR 1150646, filed Jan. 27, 2011. The disclosure of the prior applications is hereby incorporated by reference herein in its entirety.

The present invention relates to a process and a kit for determining in vitro the immune status of an individual.

Septic syndromes represent one of the main causes of mortality in intensive care units. They can be the result of a bacterial, viral, mycotic or parasitic infection. Amongst septic syndromes, we can distinguish, in increasing level of severity, SIRS (Systemic Inflammatory Response Syndrome), sepsis, severe sepsis and septic shock.

SIRS is a systemic inflammatory response triggered by a variety of infectious or non-infectious causes. Amongst the SIRS states triggered by non-infectious causes, it is possible to cite trauma states, burns, pancreatitises and acute respiratory syndromes. A systemic inflammatory response manifests itself by at least two of the following signs: a) temperature greater than 38° C. or less than 36° C.; b) heartbeat greater than 90 beats per minute; c) respiratory rate greater than 20 respirations per minute; d) number of leukocytes greater than 12,000/mm$^3$ or less than 4,000/mm$^3$, sepsis is an systemic inflammatory response syndrome related to an infection, a severe sepsis is a sepsis associated with arterial hypotension and/or hypoperfusion and/or dysfunction of at least one organ, septic shock is a severe sepsis associated with a persistent hypotension and can be characterised by:

the presence of an identified site of infection, a persistent hypotension despite adequate fills and vasopressor treatment.

The signs of a sepsis, of a severe sepsis, and of a septic shock are generally similar, and the difference between these three situations lies principally in the degree of the disruption of all of the vital functions.

The septic syndromes have for a long time been considered exclusively as an unregulated inflammatory response which leads, in response to an initial dissemination of bacteria, to a multiple organ failure in the body. However, the failures of the therapeutic, mainly anti-inflammatory approaches trialed over these past years, as well as the inability to characterise the great heterogeneity of septic patients, have contributed to the essentially pro-inflammatory view of the physiopathology of septic syndromes being called into question.

At present, the immune response during septic shock is rather described in two successive phases. After a highly inflammatory brief initial phase, responsible for the shock symptomatology per se, a state of immunodepression sets in, induced by immunosuppressing mechanisms which are responsible for controlling the pro-inflammatory response. Therefore, this anti-inflammatory component of the reaction to infection, which was initially perceived as being purely compensatory, reveals itself predominantly in the majority of patients and is accompanied by an immunosuppression and marked cellular hyporeactivity. Furthermore, it would appear that death occurs remotely from the shock (or from the initial organ failure), in a context in which patients demonstrate biological signs of immunodepression. Consequently, two causes of death would therefore appear to be present during septic shock involving different therapies. The prevention of initial death due to organ dysfunctions must be implemented as early as possible after the diagnosis, and still constitutes to date the therapeutic priority in intensive care. The prevention of delayed death, potentially due to the state of leukocyte reprogramming, might require pro-inflammatory therapies which can stimulate the immune system.

Taking into account the heterogeneity of septic patients therefore becomes more and more vital when selecting a homogeneous population during clinical trials but also during the implementation of therapies which are more and more personalised. This is all the more important since certain proposed therapies generate totally opposite effects on the immune response, and can therefore be harmful to the patients if they do not present the immuno-inflammatory status suitable for the therapeutic choice. It is therefore important to have a process and a kit which make it possible to reliably establish the overall immune status of the patient when he enters an accident and emergency or intensive care unit, and which also make it possible to define the level of deregulation of each of the components of the immuno-inflammatory response in order to implement the best-targeted therapy according to the established immune response (innate and/or adaptive). The aforementioned process and kit are also able to be used to follow the evolution of the immune status of the patient in response to a therapeutic treatment.

The invention therefore relates to a process for determining in vitro the immune status of an individual according to which:

a. a blood sample from the individual is provided, b. at least two reagents specific to at least two products of expression of at least two target genes respectively chosen from at least one of the gene families identified below, or respectively chosen from two different gene families selected from those identified below are provided:

the family of markers expressed at the surface of the circulating cells, the family of alarmins, the family of regulating, activating or inhibiting molecules, of inflammatory intracellular signal channels, the family of transcription factors, the family of pro-inflammatory soluble markers, the family of anti-inflammatory soluble markers, the family of molecules with anti-infection activity, the family of chemokines, the family of cell cycle molecules, and the family of metabolism molecules, c. the expression of said at least two target genes is determined, d. the expression of said at least two target genes respectively is compared with a reference expression, with a change in the expression of said at least two target genes relative to their reference expression indicating a change in the immune status of the individual, and a correlation between the expression of said at least two target genes with their reference expression indicating that the individual's immune status is normal.

In step b, in some particular embodiments of the invention, there are provided:

either at least three reagents which are specific to at least three products of expression of at least three target genes respectively chosen from three different gene families chosen from those identified above, or at least four reagents which are specific to at least four products of expression of at least four target genes respectively chosen from four different gene families chosen from the gene families identified above:

or at least five reagents which are specific to at least five products of expression of five target genes respectively chosen from the ten different gene families chosen from those identified above.

The preferred target genes are those identified below: The clusters of differentiation (CD) and the major class II histocompatibility complexes, such as HLA-DR, in particular HLA-DR alpha, and other clusters of differentiation which belong to the family of cellular markers, S100A9 and S100A8 which belong to the family of alarmins, ABIN-3 (TNFAIP3 interacting protein 3), IRAK-M (Interleukin-1 receptor-associated kinase 3) and LY64 (also called CD180) which belong to the family of molecules which regulate the membrane or soluble receptors, CIITA which belongs to the family of transcription factors, TNF, in particular TNF-alpha, COX-2 (also called PTGS2), FCN1 and MMP7 which belong to the family of pro-inflammatory soluble markers, IL-10 which belongs to the family of anti-inflammatory soluble markers, GBP-1 which belongs to the family of molecules with anti-infection activity, CXCL-1, CXCL-5, CXCL-7 and CXCL-10 which belong to the family of chemokines, RHOU which belongs to the family of cell cycle molecules, and PID1 which belongs to the family of metabolism molecules. It should be noted that LY64 (also called CD180) has a regulating role, and thus is classed in the family of regulating molecules, but is also a cell surface receptor.

In an embodiment of the process of the invention, the blood sample is a sample taken from an individual who has undergone an immunomodulatory treatment. The term immunomodulator shall be defined in greater detail in the "Definitions" paragraph.

The process of the invention can also comprise an additional step according to which in step a, the peripheral blood mononuclear cells (PBMCs) are extracted from the blood sample and the subsequent steps b. to d. are carried out on said blood mononuclear cells, as described previously.

The reagents specific to the products of expression of the target genes described above comprise:
either at least one amplification primer specific to said target genes,
or at least one hybridisation probe specific to said target genes,
or at least one antibody.

The invention also pertains to a kit for determining in vitro the immune status of an individual, comprising at least two reagents specific to at least two products of expression of at least two target genes respectively chosen from at least one of the gene families identified below, or respectively chosen from two different gene families selected from those identified below:
the family of markers expressed at the surface of the circulating cells,
the family of alarmins,
the family of regulating, activating or inhibiting molecules, of inflammatory intracellular signal channels,
the family of transcription factors,
the family of pro-inflammatory soluble markers,
the family of anti-inflammatory soluble markers,
the family of molecules with anti-infection activity,
the family of chemokines,
the family of cell cycle molecules, and
the family of metabolism molecules.

In particular embodiments of the invention, the kit comprises:
either at least three reagents specific to at least three products of expression of three target genes belonging respectively to three different target gene families fitting the definitions above,
or at least four reagents specific to at least four products of expression of four target genes belonging respectively to four different target gene families as defined previously,
or at least five reagents specific to at least five products of expression of five target genes belonging respectively to five different target gene families as defined above.

The preferred target genes are those identified previously, namely:
HLA-DR, in particular HLA-DR alpha, and CD which belong to the family of cellular markers,
S100A9 and S100A8 which belong to the family of alarmins, ABIN-3, IRAK-M and LY64 (also called CD180) which belong to the family of the molecules which regulate the membrane or soluble receptors,
CIITA which belongs to the family of transcription factors, TNF, in particular TNF-alpha, COX-2 (also called PTGS2), FCN1 and MMP7 which belong to the family of pro-inflammatory soluble markers,
IL-10 which belongs to the family of anti-inflammatory soluble markers,
GBP-1 which belongs to the family of molecules with anti-infection activity,
CXCL-1, CXCL-5, CXCL-7 and CXCL-10 which belong to the family of chemokines,
RHOU which belongs to the family of cell cycle molecules, and PID1 which belongs to the family of metabolism molecules.

As stated above, the reagents specific to the products of expression of the target genes comprise:
either at least one amplification primer specific to said target genes,
or at least one hybridisation probe specific to said target genes,
or at least one antibody.

The invention also pertains to the use of at least two reagents specific to at least two products of expression of at least two target genes respectively chosen from at least one of the following gene families or respectively chosen from two of the following gene families:
the family of markers expressed at the surface of the circulating cells,
the family of alarmins,
the family of regulating, activating or inhibiting molecules, of inflammatory intracellular signal channels,
the family of transcription factors,
the family of pro-inflammatory soluble markers,
the family of anti-inflammatory soluble markers,
the family of molecules with anti-infection activity,
the family of chemokines,
the family of cell cycle molecules, and
the family of metabolism molecules.

In particular embodiments of the invention, we use:
either at least three reagents specific to at least three products of expression of three target genes belonging respectively to three different target gene families fitting the definitions above, or at least four reagents specific to at least four products of expression of four target genes belonging respectively to four different target gene families as defined previously, or at least five reagents specific to at least five products of expression of five target genes belonging respectively to the five different gene families defined above.

The preferred target genes and the specific reagents respectively fit the definitions given above for the method or the kit of the invention.

Definitions

Sample of blood or blood sample equally signify whole blood, serum or plasma.

Product of expression of a specific target gene is understood to be messenger RNA or an mRNA fragment, cDNA or a cDNA fragment, a protein or a protein fragment.

Specific reagent is understood to be a reagent which reacts with a biological material of the sample of blood or peripheral blood mononuclear cells (PBMCs) in order to reveal, directly or indirectly, the expression of a target gene, which can be determined by analysing the mRNAs from this gene or by analysing the protein encoded by this gene.

By way of indication, when it is desired to determine the expression of a target gene by analysing the protein encoded by this gene, this specific reagent comprises at least one antibody specific to the protein encoded by this target gene.

By way of indication, when it is desired to determine the expression of a target gene by analysing the mRNAs transcribed from this gene, this specific reagent comprises at least one amplification primer specific to the DNA which is complementary to this mRNA (then referred to as amplification primer specific to a target gene). The DNA complementary to an mRNA can be obtained according to a protocol well known to a person skilled in the art. For example, the total RNAs (comprising ribosomal RNAs, transfer RNAs, mRNAs) are extracted from the sample of blood or the PBMCs. A reverse transcription reaction is then performed by means of a reverse transcriptase enzyme, which makes it possible to obtain, from an RNA fragment, a complementary DNA fragment (cDNA). The execution of such a step is well known to the person skilled in the art. When it is more particularly desired to obtain only the DNAs complementary to the messenger RNAs, this enzymatic step is performed in the presence of nucleotide fragments comprising only thymine bases (polyT), which hybridize by complementarity on the polyA sequence of the various mRNAs in order to form a polyT-polyA complex, which then serves as the starting point for the reverse transcription reaction performed by the reverse transcriptase enzyme. Various DNAs that are complementary to the various messenger RNAs initially present in the blood sample or in the PBMCs are then obtained. In the following text, cDNA denotes a DNA complementary to a messenger RNA.

Amplification primer means a nucleotide fragment with from 5 to 100 nucleotide units, preferably from 15 to 25 nucleotide units, and possessing a hybridisation specificity under determined conditions in order to initiate enzymatic polymerization, for example in an enzymatic amplification reaction.

Enzymatic amplification reaction means a process generating multiple copies of a target nucleotide fragment by means of specific amplification primers by the action of at least one enzyme. Such amplification reactions are well known to the person skilled in the art, and in particular the following techniques may be cited: PCR (Polymerase Chain Reaction), LCR (Ligase Chain Reaction), RCR (Repair Chain Reaction), 3SR (Self Sustained Sequence Replication) with patent application WO-A-90/06995, NASBA (Nucleic Acid Sequence-Based Amplification), and TMA (Transcription Mediated Amplification) with the patent U.S. Pat. No. 5,399,491.

The term amplicons designates the polynucleotides generated by an enzymatic amplification technique. Preferably, when the enzymatic amplification is a PCR, the specific reagent comprises at least 2 specific amplification primers in order to amplify a particular region of the complementary DNA of the mRNA from the target gene. When the enzymatic amplification is a PCR performed after a reverse transcription reaction, it is called RT-PCR.

Hybridisation probe means a nucleotide fragment comprising from 5 to 100 nucleotide units, preferably from 6 to 35 nucleotide units, possessing a hybridisation specificity under determined conditions to form a hybridisation complex with a target nucleotide fragment. In the present invention, the target nucleotide fragment can be a nucleotide sequence contained in a messenger RNA, or a nucleotide sequence contained in a complementary DNA obtained by reverse transcription of said messenger RNA.

Hybridisation means the process during which, in suitable conditions, two nucleotide fragments, such as for example a hybridisation probe and a target nucleotide fragment, having sufficiently complementary sequences, are able to form a double strand with stable and specific hydrogen bonds. A nucleotide fragment "capable of hybridizing" with a polynucleotide is a fragment that can hybridize with said polynucleotide in hybridisation conditions, which can be determined in each case in a known manner. The hybridisation conditions are determined by the stringency, i.e. the rigor of the operating conditions. Hybridisation becomes increasingly specific as its stringency increases. Stringency is defined notably as a function of the base composition of a probe/target duplex, as well as by the degree of mismatch between two nucleic acids. Stringency can also be a function of the reaction parameters, such as the concentration and the type of ionic species present in the hybridisation solution, the nature and the concentration of denaturing agents and/or the hybridisation temperature. The stringency of the conditions in which a hybridisation reaction must be performed will principally depend on the hybridisation probes used. All of these data are well known and the appropriate conditions can be determined by the person skilled in the art. In general, depending on the length of the hybridisation probes used, the temperature for the hybridisation reaction is between about 20 and 70° C., in particular between 35 and 65° C. in a saline solution at a concentration of about 0.5 to 1 M. A hybridisation reaction detection step is then performed.

Detection means either direct detection by a physical method, or a method of detection by means of a label. There are numerous detection methods for detecting nucleic acids [1, 2].

Label means a tracer capable of producing a signal. A non-limiting list of these tracers comprises the enzymes that produce a signal detectable for example by colorimetry, fluorescence or luminescence, such as horseradish peroxidase, alkaline phosphatase, β-galactosidase, glucose-6-phosphate dehydrogenase; chromophores such as fluorescent, luminescent or staining compounds; electron density groups detectable by electron microscopy or by their electrical properties such as conductivity, by amperometry or voltammetry methods, or by impedance measurements; groups detectable by optical methods such as diffraction, surface plasmon resonance, variation of contact angle or by physical methods such as atomic force spectroscopy, tunnel effect, etc.; radioactive molecules such as $^{32}P$, $^{35}S$ or $^{125}I$. Thus, the polynucleotide can be labelled during the enzymatic amplification step, for example by using a triphosphate nucleotide labelled for the amplification reaction. The labelled nucleotide will be a deoxyribonucleotide in amplification systems generating a DNA, such as PCR, or a ribonucleotide in amplification techniques generating an RNA, such as the TMA or NASBA techniques. The polynucleotide can also be labelled after the amplification step, for example by hybridising a probe labelled according to the sandwich hybridisation technique described in document WO-A-91/19812.

In the terms of the present invention, the hybridisation probe can be a so-called capture probe. In this case, the target nucleotide fragment can be labelled beforehand by means of a label. The so-called capture probe is immobilised or able to be immobilised on a solid support by any suitable means, i.e. directly or indirectly, for example by covalence or adsorption. A hybridisation reaction is then performed between said detection probe and the labelled target nucleotide fragment.

The hybridisation probe can also be a so-called detection probe. In this case, the hybridisation probe can be labelled by means of a label. A hybridisation reaction is then performed between said detection probe and the target nucleotide fragment.

Whether a so-called capture probe or a so-called detection probe is used, the hybridisation reaction can be performed on a solid support, which includes all materials on which a nucleic acid can be immobilized. Synthetic materials or natural materials, possibly chemically modified, can be used as the solid support, notably polysaccharides such as cellulose-based materials, for example paper, cellulose derivatives such as cellulose acetate and nitrocellulose or dextran, polymers, copolymers, notably based on styrene-type monomers, natural fibres such as cotton, and synthetic fibres such as nylon; mineral materials such as silica, quartz, glasses, ceramics; latexes; magnetic particles; metal derivatives, gels etc. The solid support can be in the form of a microtitration plate, a membrane as described in application WO-A-94/12670, a particle or a biochip.

In the present invention, the determination of the expression of a target gene can be analyzed by the expression of the mRNAs which are transcribed at a given time. In this case, the biological material is a nucleic acid, and the specific reagent can equally be an amplification primer or a hybridisation probe as defined previously.

The expression of a target gene can be determined as follows:

1) after extracting the total RNAs from a sample of blood or PBMCs, a reverse transcription step is performed, such as described previously, in order to obtain the various DNAs complementary to the various messenger RNAs initially present in the blood sample or in the PBMCs (or cDNA)

2) the cDNAs are amplified specifically. In this case, the specific reagent used comprises at least one amplification primer specific to the target gene, as defined previously. This step can notably be performed by an amplification reaction such as PCR, or by any other suitable amplification technique 3) the expression of the target gene is determined by quantifying the cDNAs. The cDNAs can be quantified notably by using a quantification range obtained by an amplification reaction carried out to saturation. In order to take into account the variability in enzymatic efficiency that may be observed during the various steps (reverse transcription, quantitative PCR, etc.), the expression of the target gene of the different groups of patients can be standardized by simultaneous determination of the expression of a so-called housekeeping gene, whose expression is similar in the different groups of patients. By finding the ratio of the expression of the target gene to the expression of the housekeeping gene, any variability between the different trials is thus corrected. The person skilled in the art can notably refer to the following publications: [3-4] Bustin S A *Journal of molecular endocrinology,* 2002, 29: 23-39; Giulietti A *Methods,* 2001, 25: 386-401

The expression of a target gene can also be determined as follows:

1) after extracting the total RNAs from a sample of blood or PBMCs, a reverse transcription step is performed, such as described previously, in order to obtain the various DNAs complementary to the various messenger RNAs initially present in the sample or the PBMCs (or cDNA)

2) the cDNAs are immobilised on a membrane 3) the expression of the target gene is determined by hybridizing the cDNAs with previously labelled hybridisation probes specific to the target gene. Such hybridisation reactions are well known to the person skilled in the art, and it is possible to cite in particular the Northern blot technique. This hybridisation reaction can be performed after a stage of specific amplification of the DNAs complementary to the messenger RNAs of a target gene, notably when the gene is weakly expressed The expression of a target gene can also be analyzed by the expression of the proteins encoded by the target gene. In this case, the biological material is a protein and several detection techniques with or without a ligand can be used. Mass spectrometry can be used as the technique for detection without a ligand. The specific reagent can be an antibody specific to the protein encoded by the target gene for a detection system with a ligand.

Recombinant antibodies specific to the protein translated from the target gene can be obtained according to conventional methods known by a person skilled in the art, from prokaryotic organisms, such as bacteria, or from eukaryotic organisms, such as yeasts, cells of mammals, of plants, of insects or of animals, or by extracellular production systems.

Monoclonal antibodies can be prepared according to conventional techniques known to the person skilled in the art such as the hybridoma technique, the general principle of which is recalled hereunder.

Firstly, an animal, generally a mouse (or cells in culture in the case of in vitro immunizations) is immunized with a target antigen of interest, its B lymphocytes then being capable of producing antibodies against said antigen. These antibody-producing lymphocytes are then fused with "immortal" myeloma cells (murine in the example) to give rise to hybridomas. From the heterogeneous mixture of cells thus obtained, cells are then selected that are capable of producing a particular antibody and of reproducing indefinitely. Each hybridoma is reproduced in the form of a clone, each leading to the production of a monoclonal antibody, whose recognition properties with respect to the antigen of interest will be able to be tested for example by ELISA, by immunotransfer in one or two dimensions, by immunofluorescence, or by means of a biosensor. The monoclonal antibodies thus selected are then purified as follows, notably in accordance with the affinity chromatography technique.

Antibody fragments can for example be obtained by proteolysis. Thus, they can be obtained by enzymatic digestion, resulting in Fab-type fragments (papain treatment [5]) or F(ab)'2-type fragments (pepsin treatment [6]). They can also be prepared by recombination [7]. Another antibody fragment that is suitable for the purposes of the invention comprises an Fv fragment, which is a dimer constituted of the non-covalent association of the variable light domain (VL) and the variable heavy domain (VH) of the Fab fragment, and therefore of an association of two polypeptide chains. In order to improve the stability of the Fv fragment due to the dissociation of the two polypeptide chains, this Fv fragment can be modified by genetic engineering by inserting a suitable peptide bond between the VL domain and the VH domain [8]. This is then called a scFv fragment ("single chain Fragment variable"), as it is constituted of a single polypeptide chain. The use of a peptide bond preferably composed of 15 to 25 amino acids makes it possible to connect the C-terminal end of a domain to the N-terminal end of the other domain, thus forming a monomeric molecule endowed with binding properties similar to those of the antibody in its complete form. The two orientations of the VL and VH domains are suitable (VL-bond-VH and VH-bond-VL) because they have identical functional properties. Of course, any fragment known to the person skilled in the art and having the immunological characteristics defined above is suitable for the purposes of the invention.

When the biological material is a protein resulting from the expression of a gene, the expression of the latter can be determined by detecting and/or quantifying said protein by Western Blotting or ELISA, or any other method known to the person skilled in the art, such as a method of chemiluminescence based on the biological material.

The ELISA ("Enzyme Linked Immuno Sorbent Assay") technique is an immunoenzymatic assay on a solid support. This test comes within the more general scope of EIAs ("Enzyme Immunoassays"), in which the assay is coupled to an enzyme-catalyzed reaction. The technique uses one or two antibodies. The antibody for detecting the formation of immune complexes (antigen/antibody) is coupled to the enzyme and can generate the emission of a signal by a chromogenic or fluorogenic substrate.

The Western Blot technique is a test for detecting a specific protein in a sample by means of an antibody specific to this protein, comprising the following steps as described hereunder.

The first step is a gel electrophoresis, which makes it possible to separate the sample proteins according to their size.

The proteins in the gel are then transferred onto a membrane (nitrocellulose, PVDF etc.) by pressure or by application of an electric current, the proteins becoming fixed on the membrane through hydrophobic and ionic interactions.

After saturation of the sites of non-specific interaction, a first antibody specific to the protein to be studied (primary antibody) is incubated with the membrane.

The membrane is then rinsed to remove the unbound primary antibodies, then incubated with so-called secondary antibodies, which will bind to the primary antibodies. This secondary antibody is usually bound to an enzyme that makes it possible to visually identify the protein studied on the membrane. The addition of a substrate labelled with the enzyme produces a coloured reaction which is visible on the membrane.

Immunomodulating products are understood to be immunostimulants and immunosuppressors.

Immunostimulation is much in demand for example in the case of immunosuppression (septic syndrome), immunodeficiency (AIDS), in the case of chronic infections and in the case of cancers. Cytokines can be immunostimulating molecules. The term "cytokines" designates a heterogeneous group of proteins produced by the white line cells. They have an essential role in the regulation of the immune system and of hematopoiesis. The main molecule families used therapeutically as immunostimulants are:
- the family of interleukins, such as IL-2, IL-7 and IL-15,
- the family of growth factors, such as G-CSF (Granulocyte Colony Stimulating Factor), GM-CSF (Granulocyte Macrophage Colony Stimulating Factor) and FLT3-L (Fms-Like Tyrosine kinase 3 Ligand),
- the family of interferons such as the α, β and γ . . . ) interferons,
- the family of Toll agonists,
- the family of blocking antibodies (anti-IL-10, anti-CTLA4, anti-PD-1 . . . ),
- the family of transferrins, such as lactoferrin and talactoferrin,
- the family of apoptosis-blocking molecules, such as protease inhibitors, caspase inhibitors, Fas/FasL inhibitors, Bcl-2 inductors.

Immunosuppression is sought in order to inhibit or prevent activity of the immune system. Immunosuppressors are used to limit the immune dysfunctions produced by an exacerbated pro-inflammatory response in the case of a septic syndrome, prevent organ and transplant graft rejection, to treat auto-immune illnesses or illnesses likely to be auto-immune in origin. The immunosuppressors are generally divided into several families:
- the family of glucocorticoids,
- the family of cytostatics,
- the family of blocking antibodies (anti-TNF),
- the family of molecules which act on immunophilins and,
- other molecules, in particular cytokines which can be immunosuppressive molecules, such as IL-10, IL-3, TGF-β, IL-1 RA.

219093_at for PID1 and (T) 223168_at for RHOU. The black histograms show the negative controls (without stimulation). The white histograms correspond to the cells stimulated just once with 100 ng/mL of LPS, and the grey histograms show the cells subjected to two stimulations by LPS (2 ng/ml then 100 ng/m1). The data are represented as mean+/−standard deviation. A matched-pair t-test was performed for the statistical analysis of the results: *, signifies that p<0.05 vs. cells stimulated once with LPS.

Figure 3A:
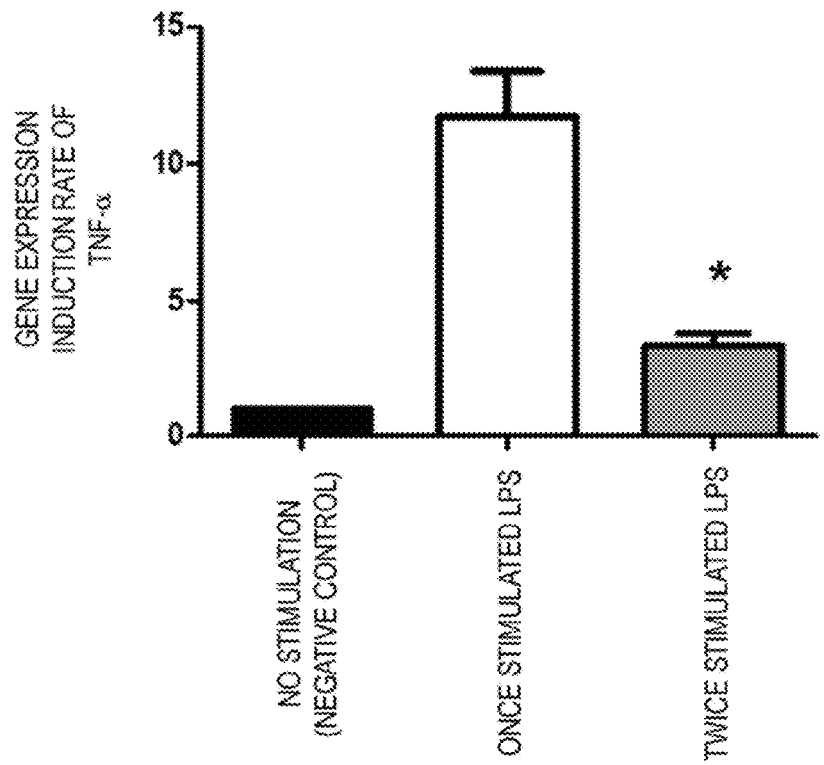
Figure 3B:
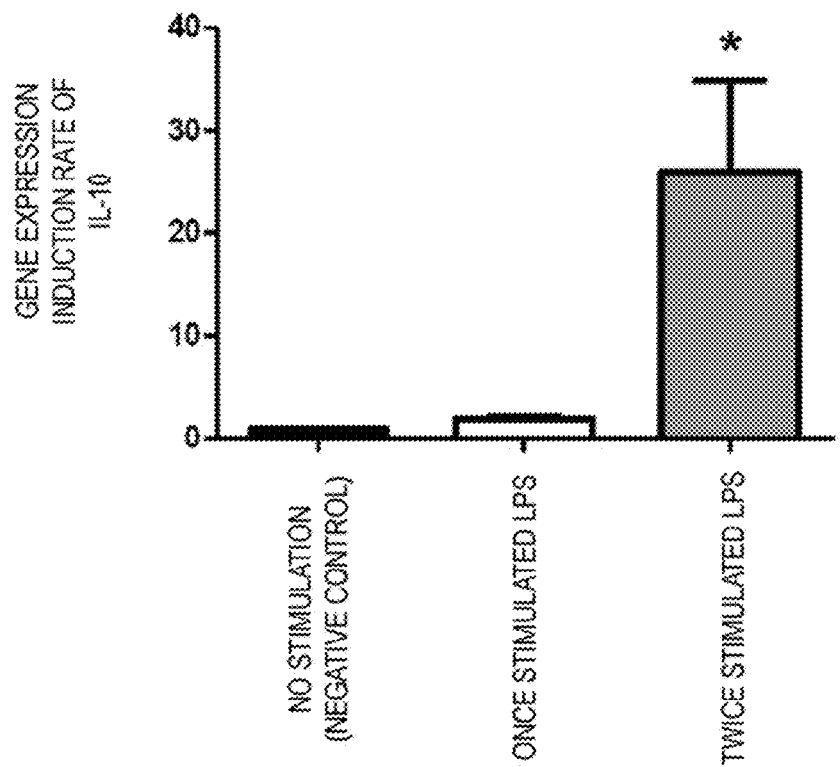
Figure 3C:
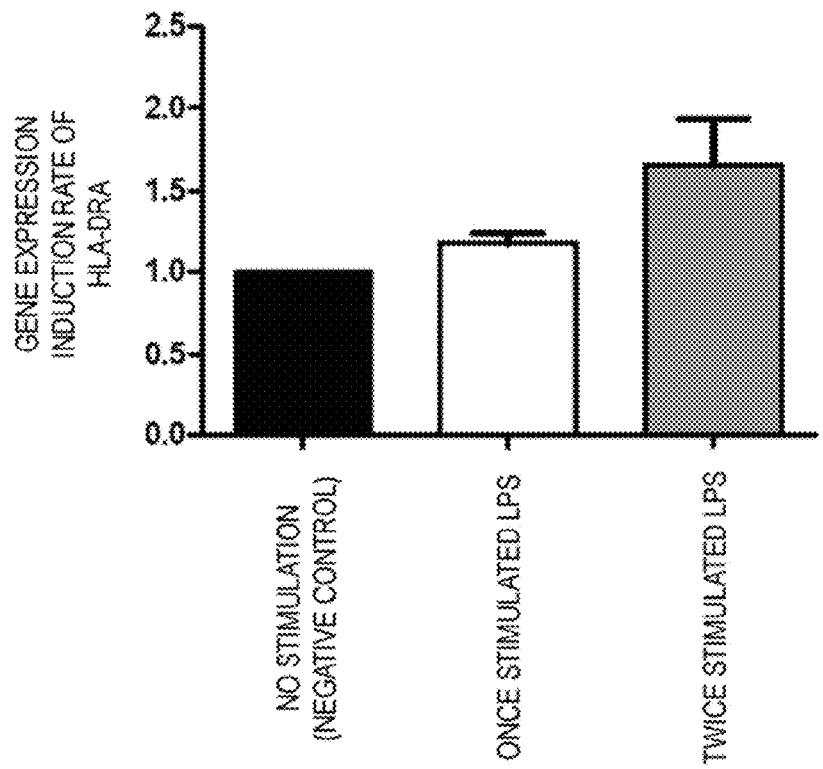
Figure 3D:
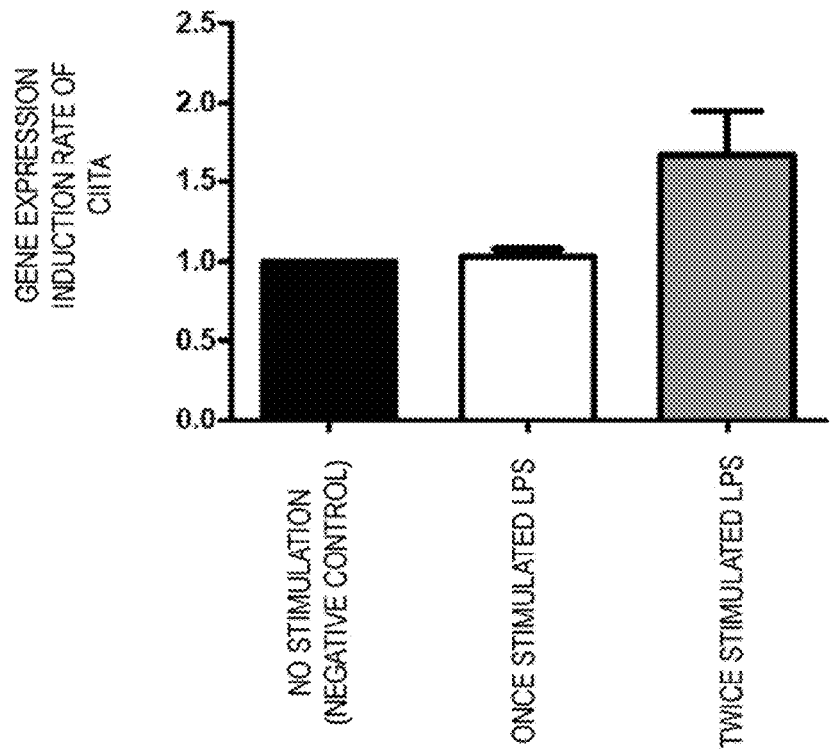
Figure 3E:
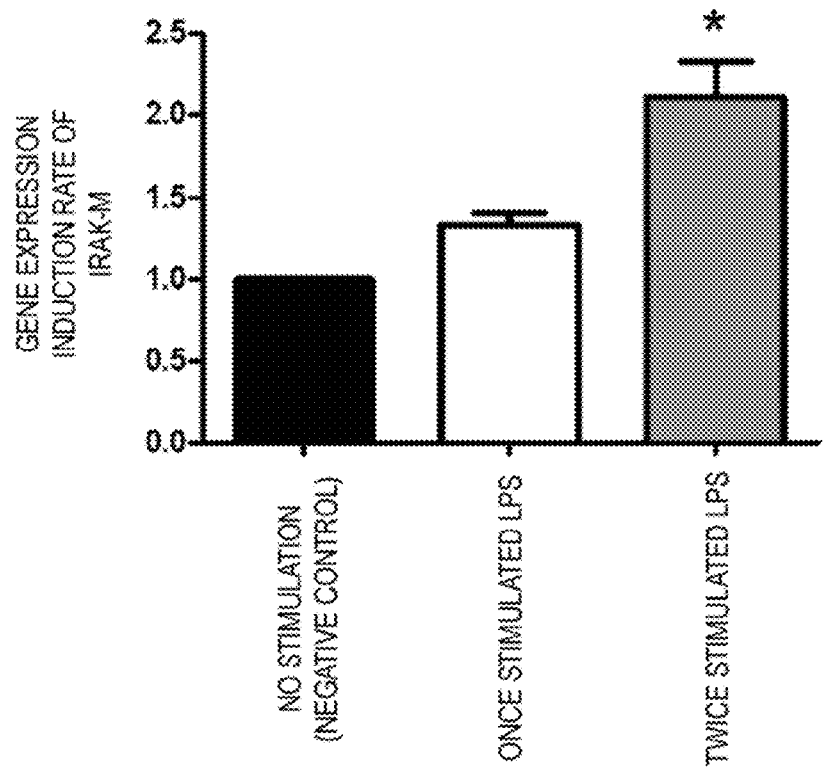
Figure 3F:
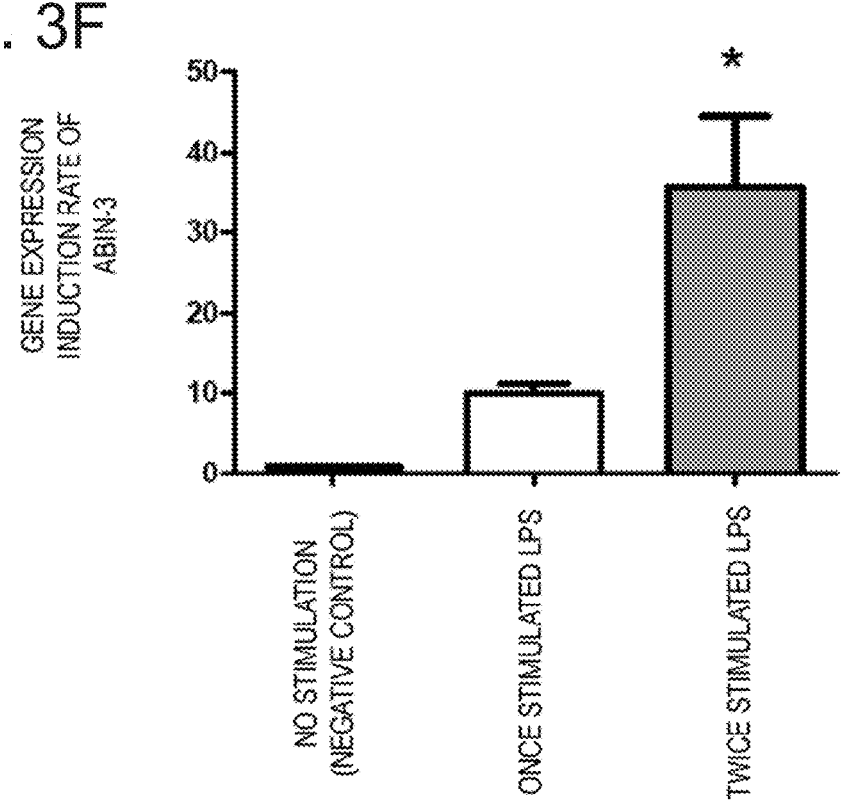
Figure 3G:
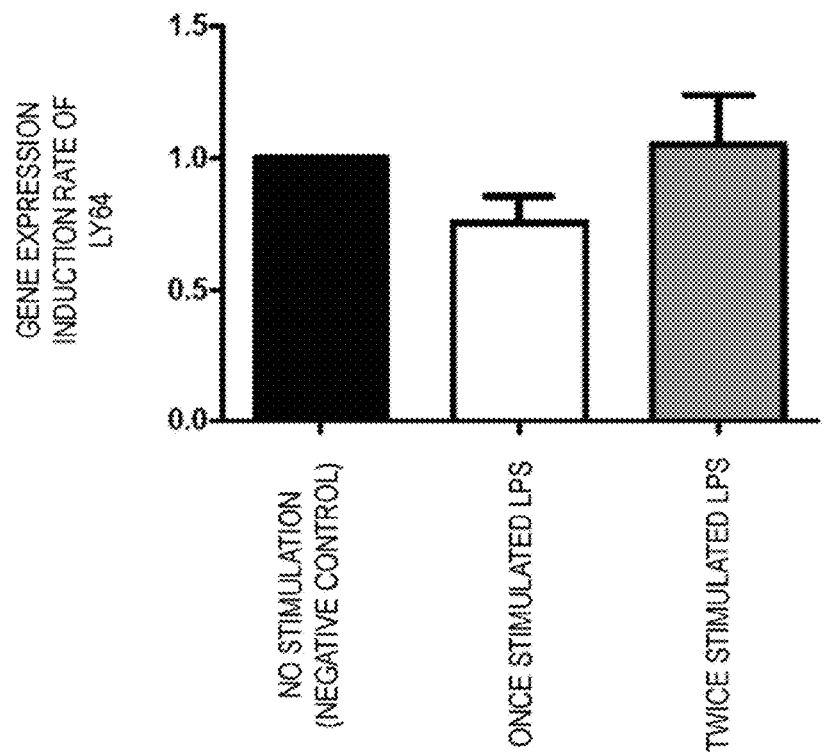
Figure 3H:
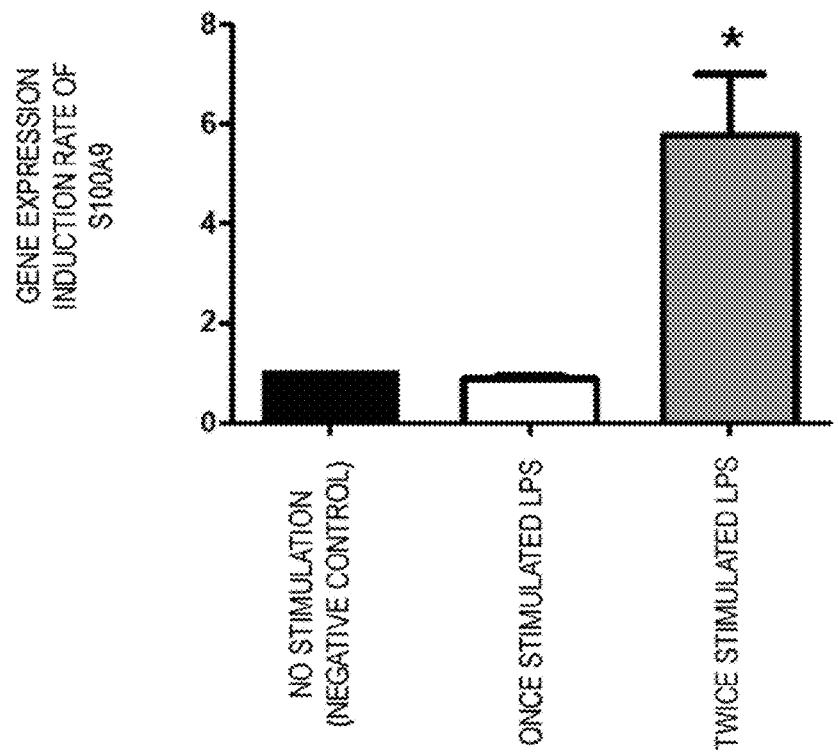
Figure 3I:
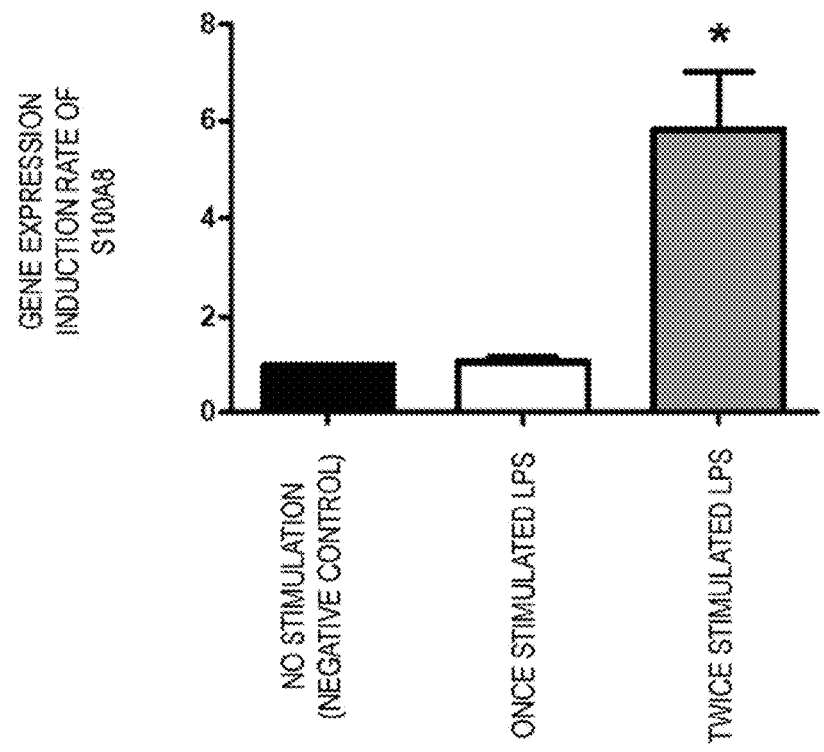
Figure 3J:
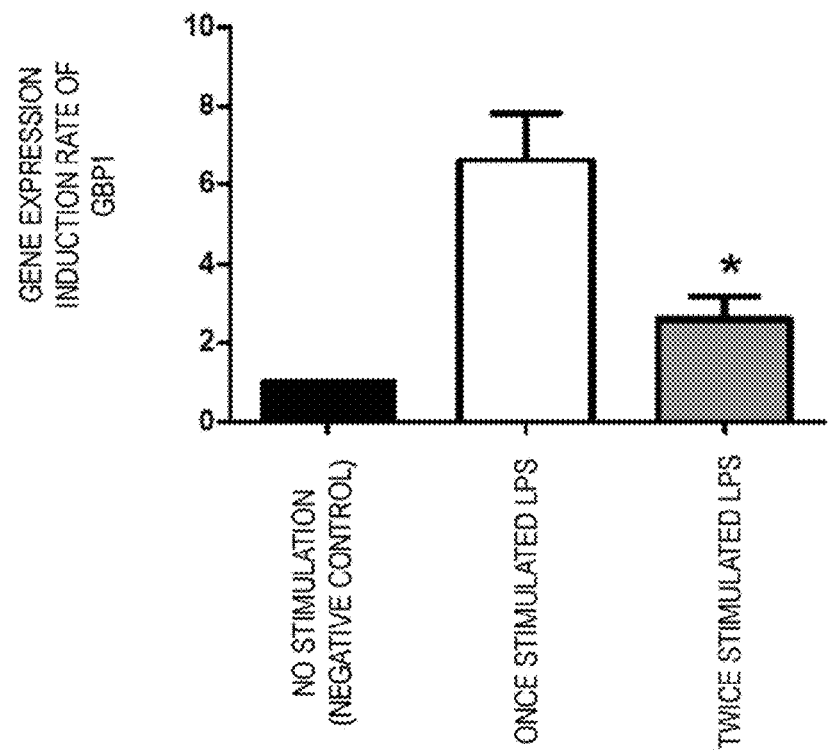
Figure 3K:
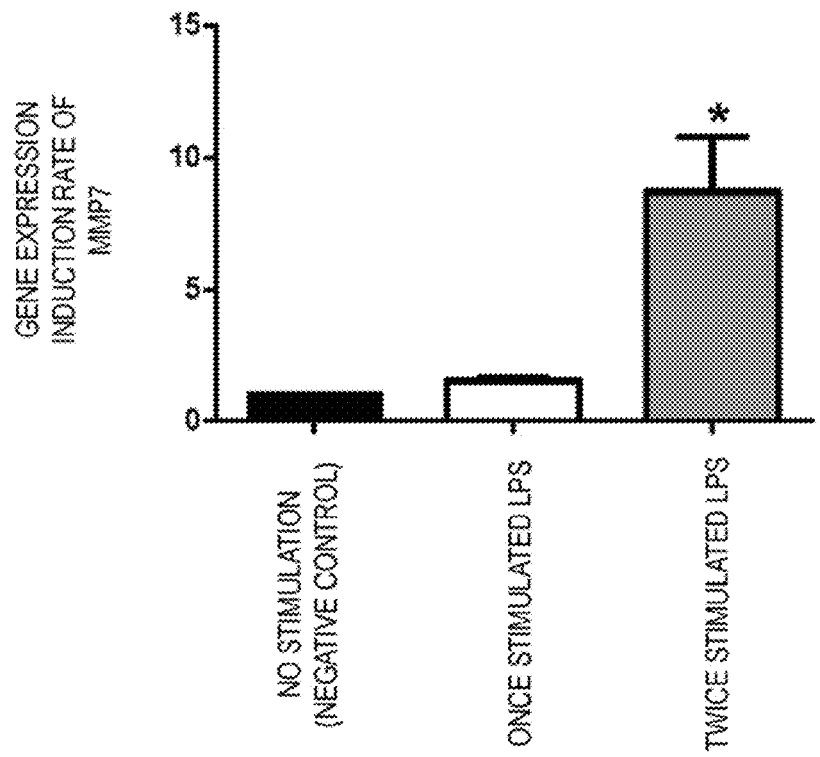
Figure 3L:
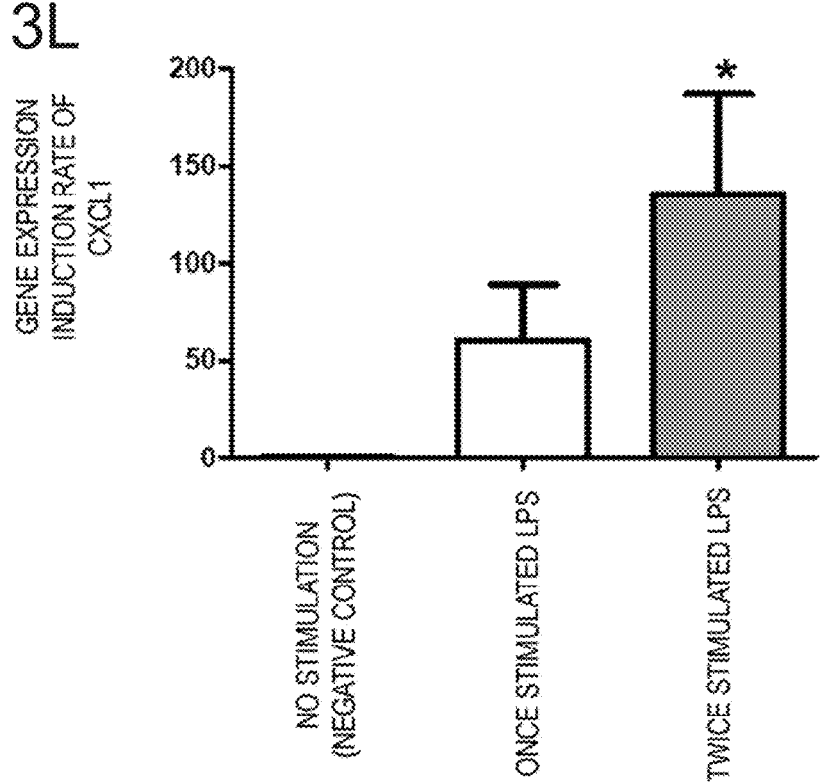
Figure 3M:
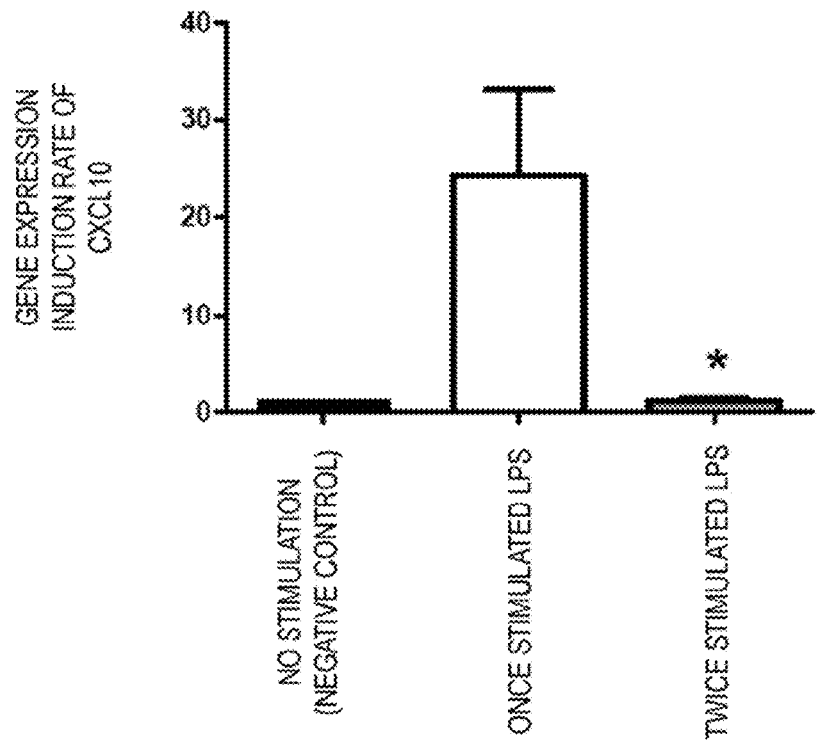
Figure 3N:
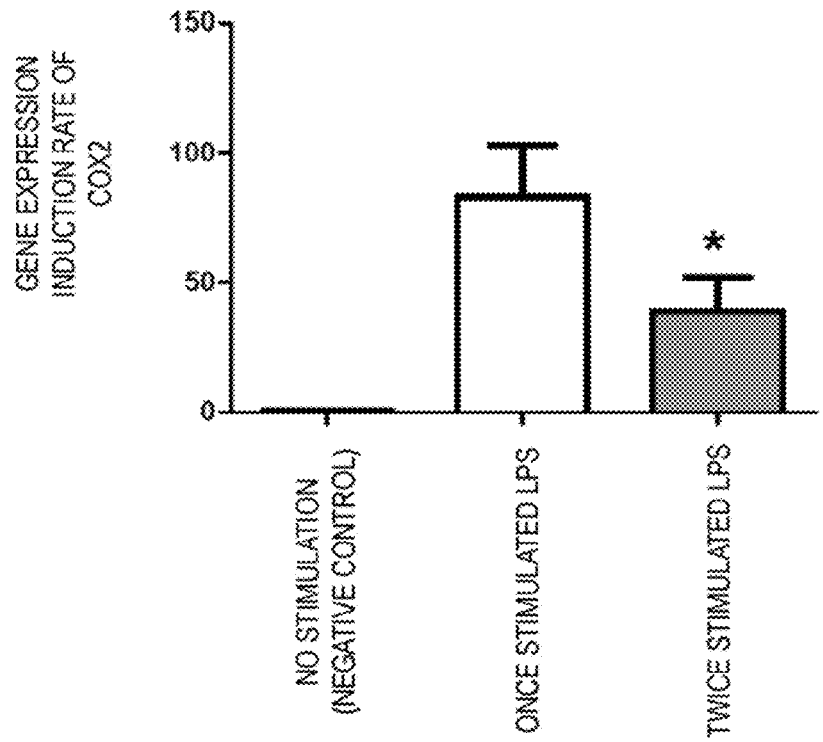
Figure 3O:
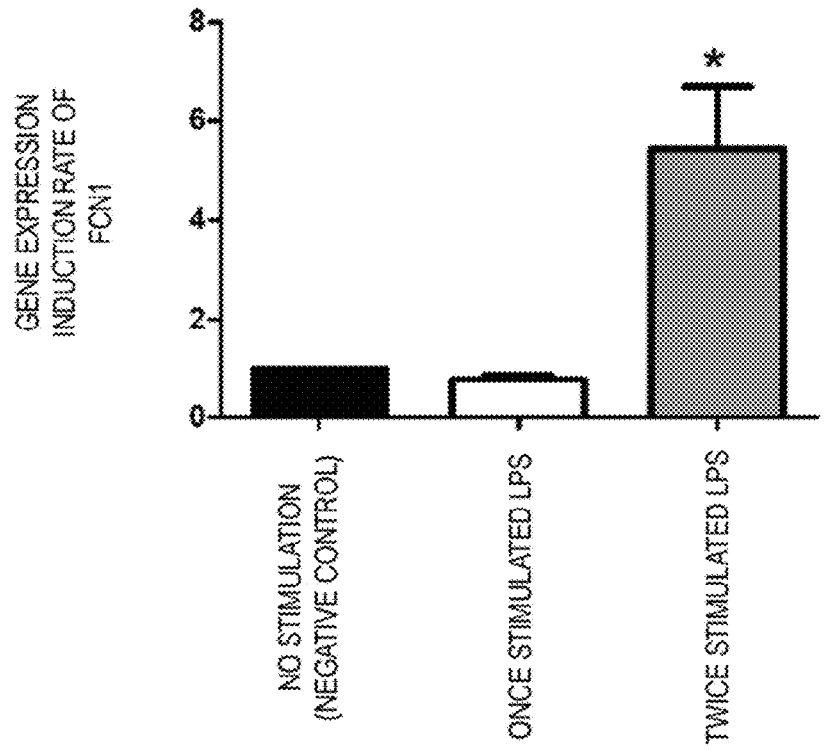
Figure 3P:
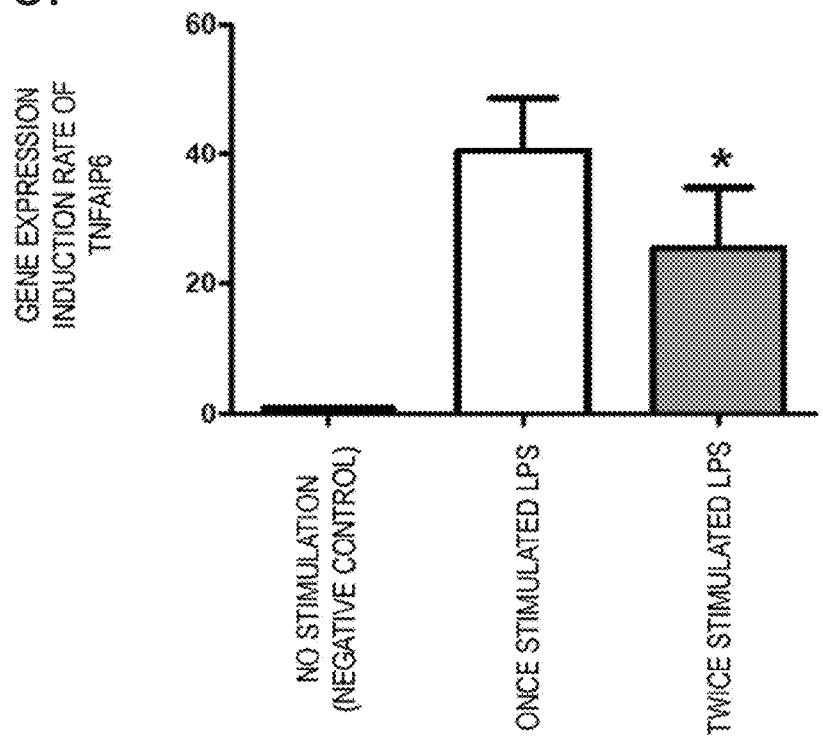
Figure 3Q:
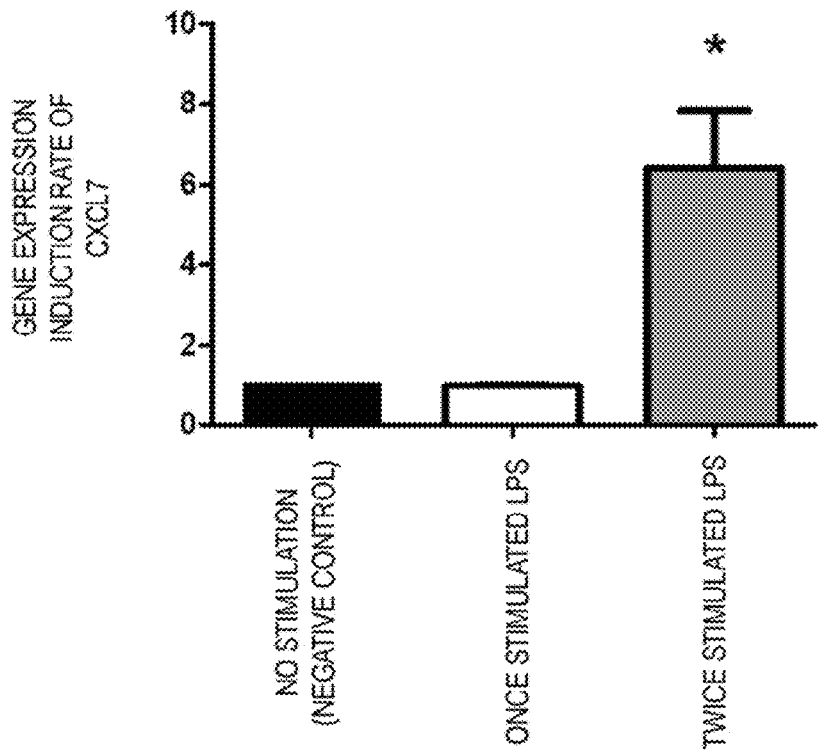
Figure 3R:
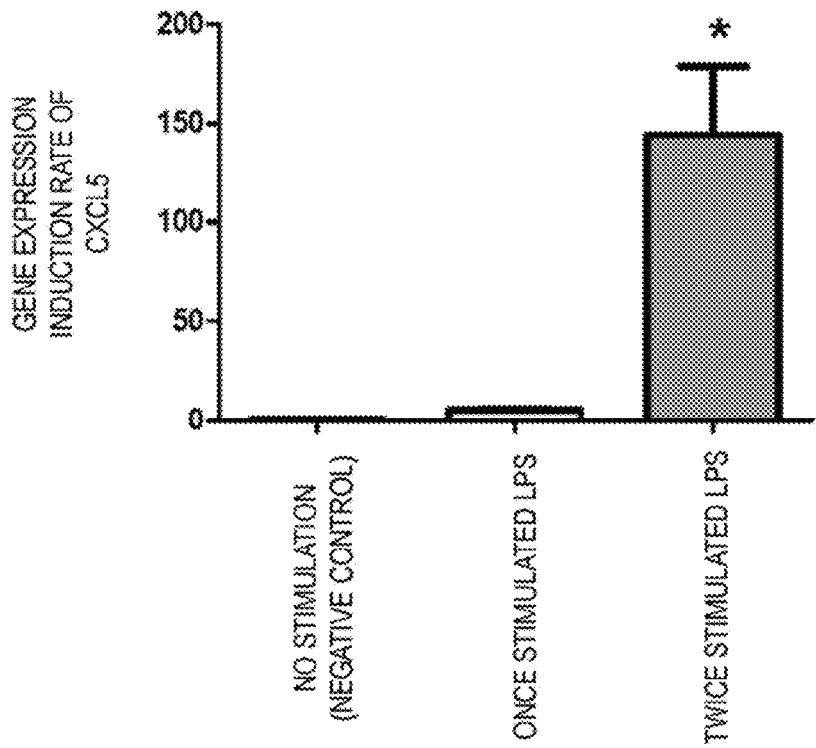
Figure 3S:
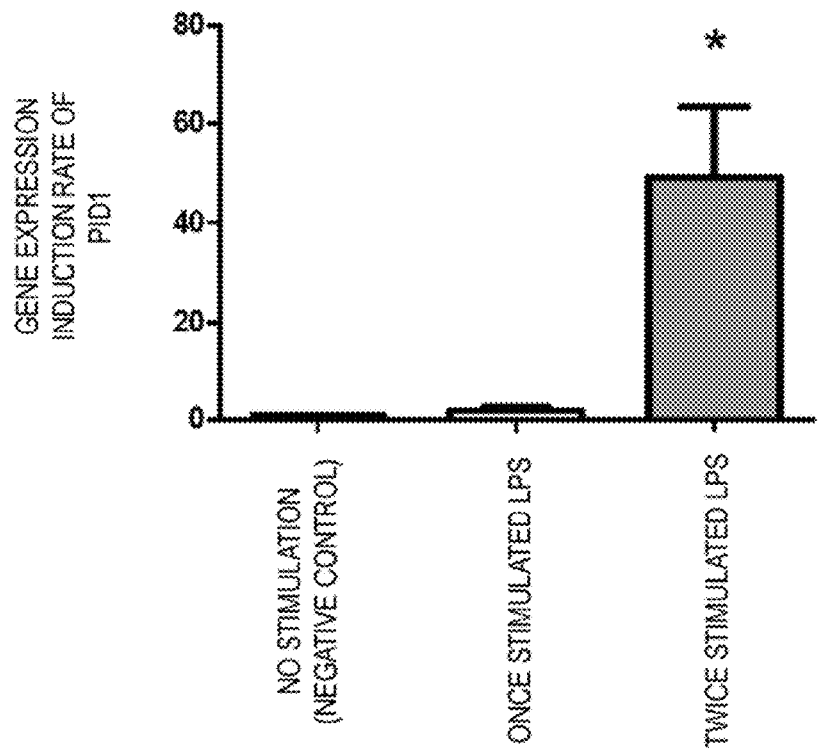
Figure 3T:
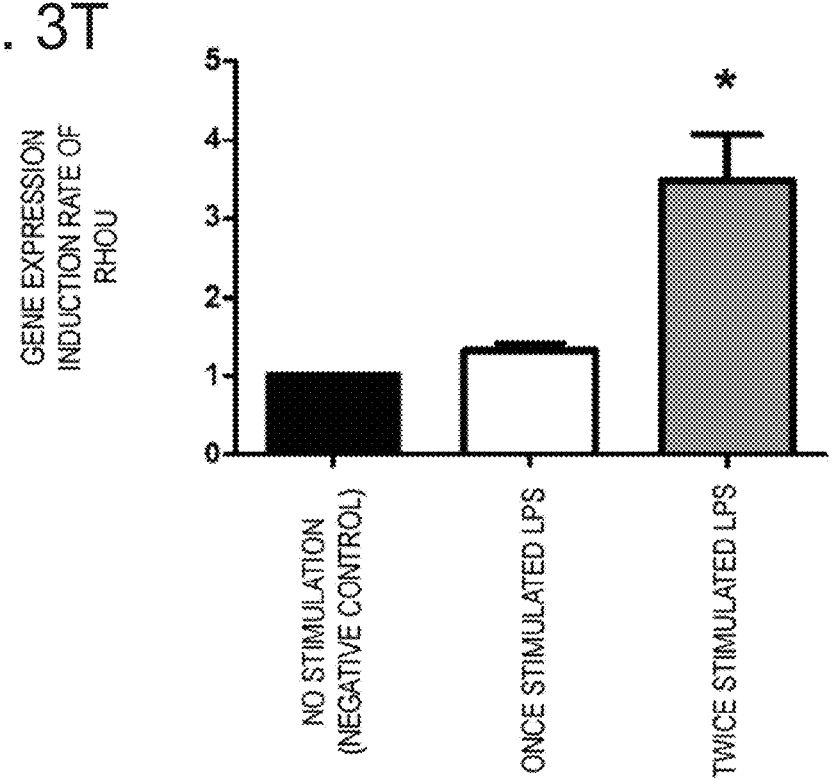

FIGS. 3A-3T respectively show the expression of the TNF alpha (A), IL-10 (B), HLA-DRA (C), CIITA (D), IRAK-M (E), ABIN-3 (F), LY64 (G), S100A9 (H), S100A8 (I), GBP1 (J), MMP7 (K), CXCL1 (L), CXCL10 (M), COX2 (N), FCN1 (O), TNFAIP6 (P), CXCL7 (Q), CXCL5 (R), PID1 (S) and RHOU (T) genes by PBMCs, which come from 7 healthy volunteers, stimulated by LPS and quantified by qRT-PCR after 45 hours. The y axis represents the gene expression induction rates cited above. The black histograms show the negative controls (without stimulation). The white histograms correspond to the cells stimulated just once with 100 ng/mL of LPS, and the grey histograms show the cells subjected to two stimulations by LPS (2 ng/ml then 100 ng/m1). The data are represented as mean+/−standard deviation. A Wilcoxon matched-pair test was performed for the statistical analysis of the results: *, signifies that p<0.05 vs. cells stimulated once with LPS.

Figure 4A:
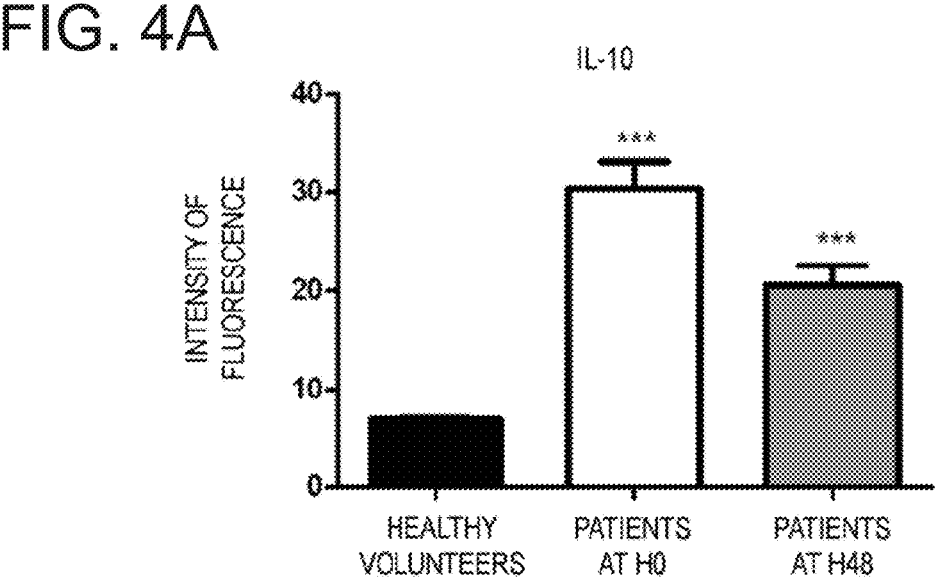
Figure 4B:
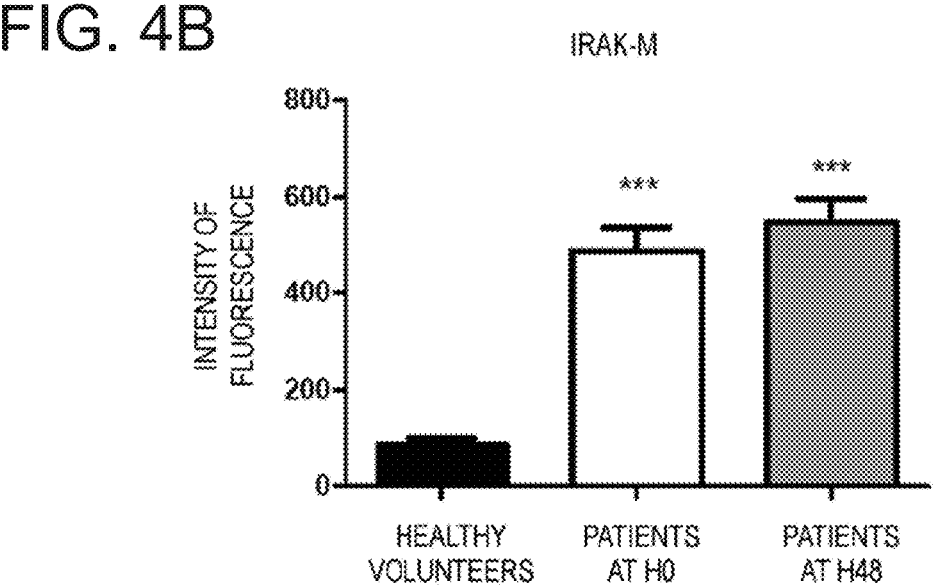
Figure 4C:
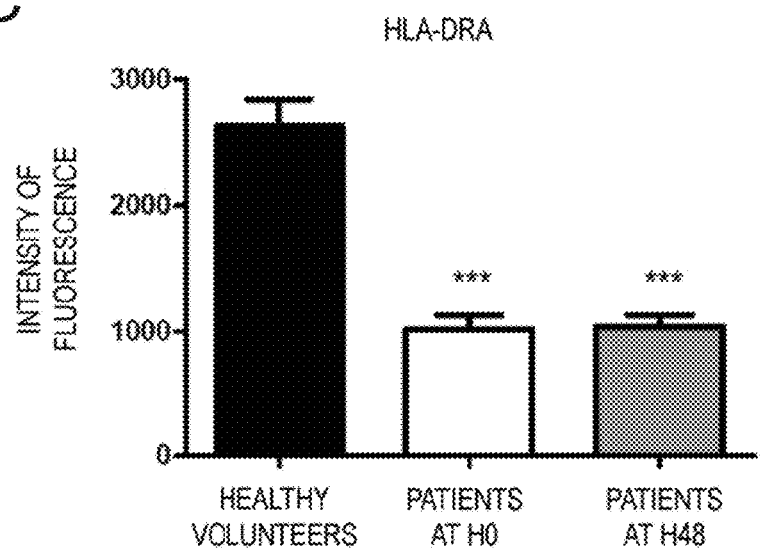
Figure 4D:
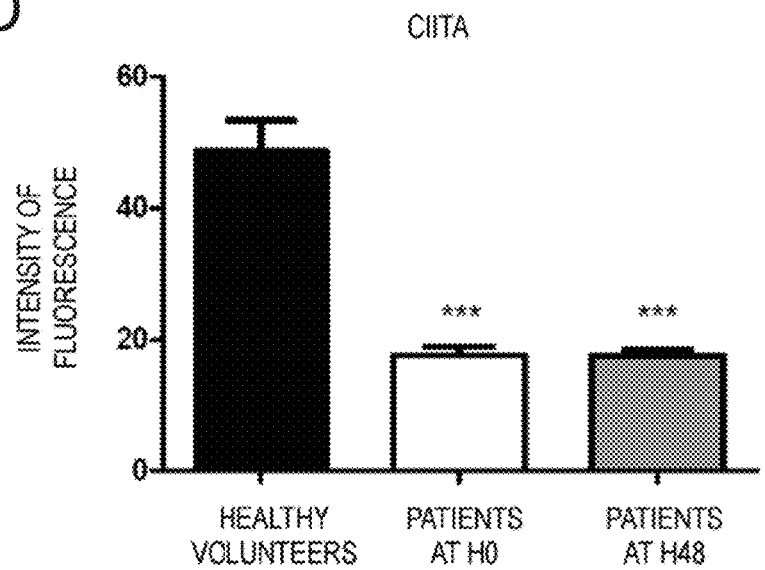
Figure 4E:
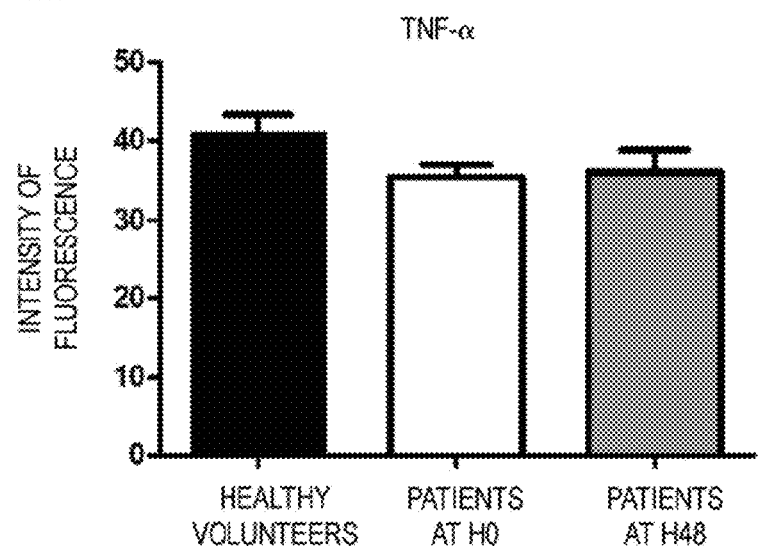
Figure 4F:
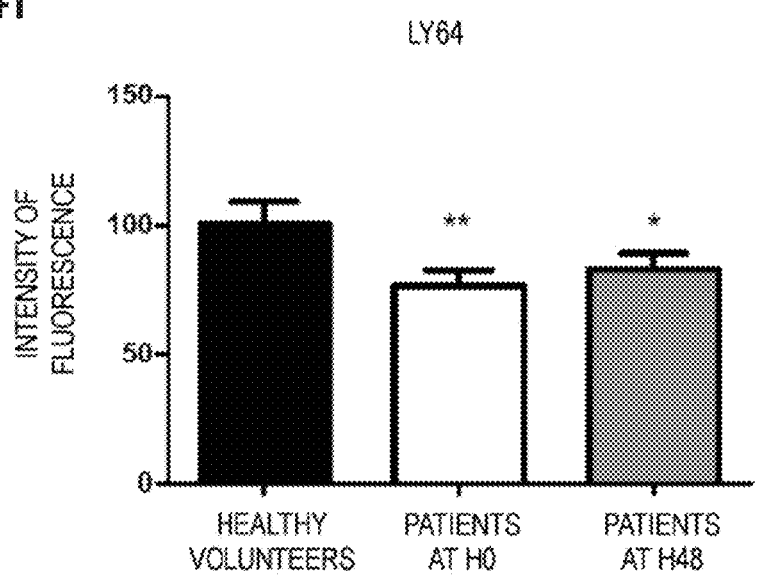
Figure 4G:
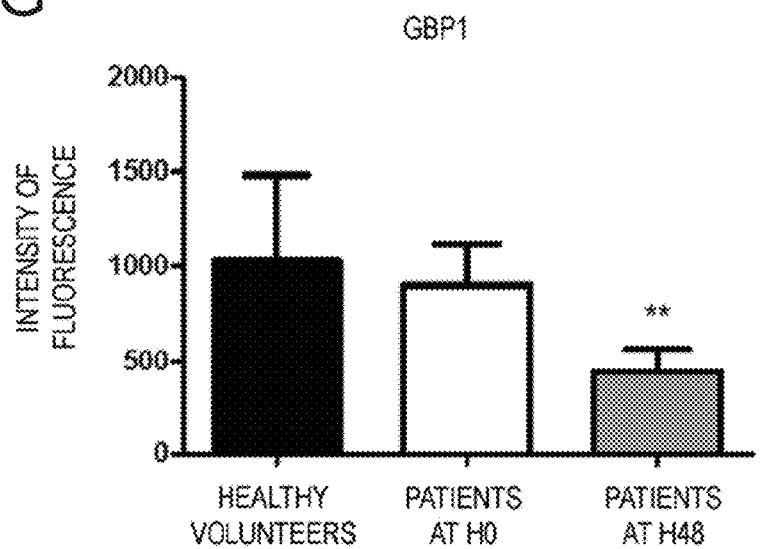
Figure 4H:
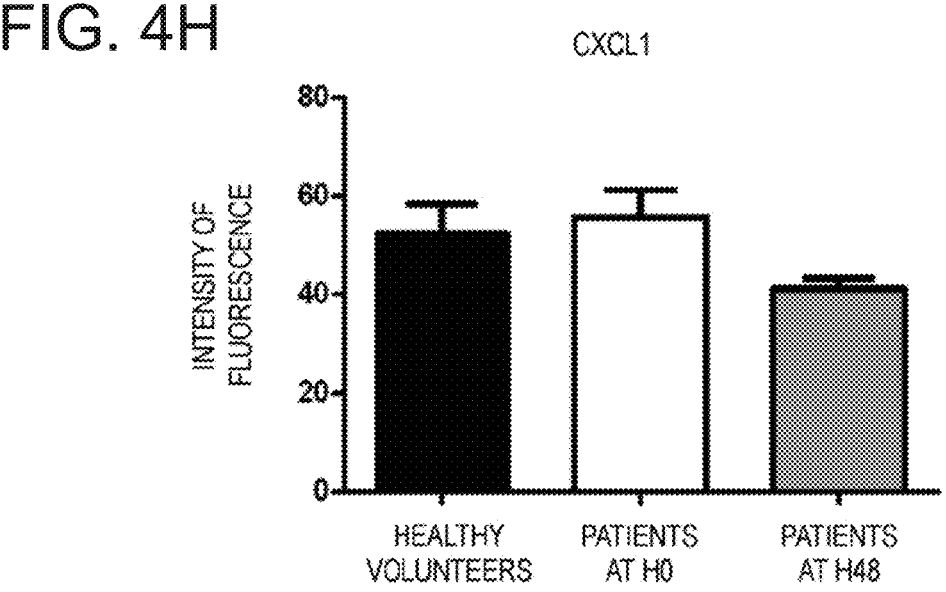
Figure 4I:
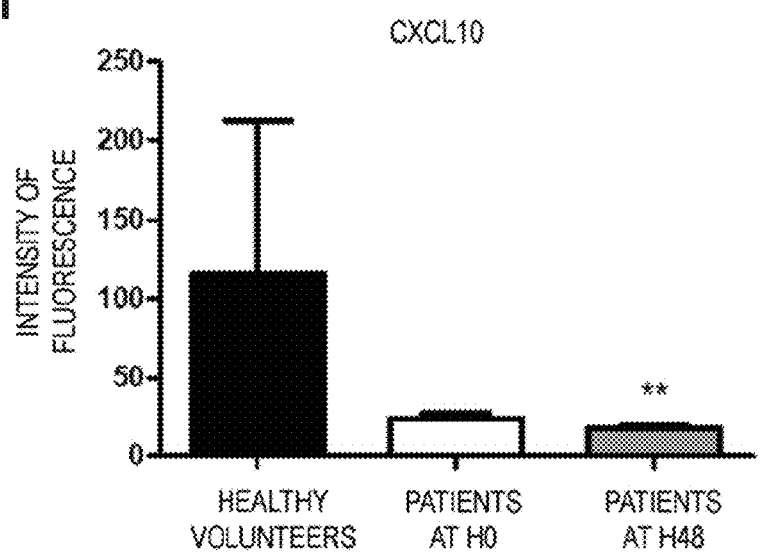
Figure 4J:
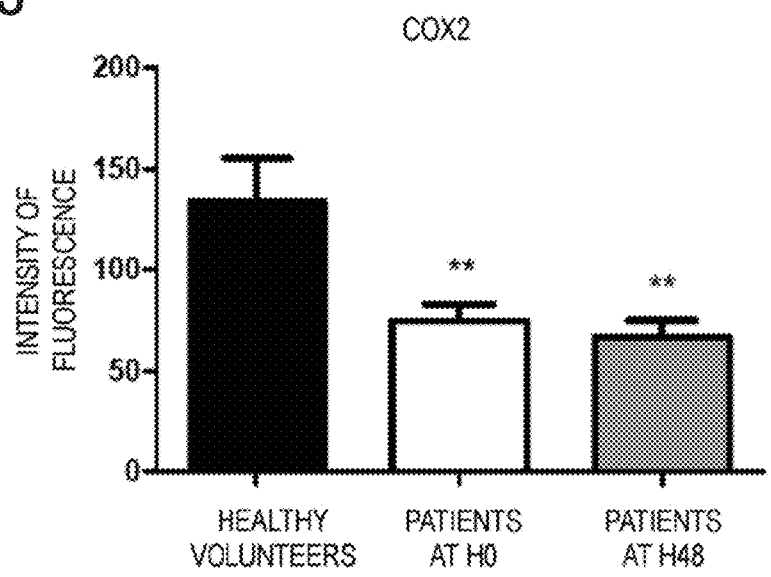
Figure 4K:
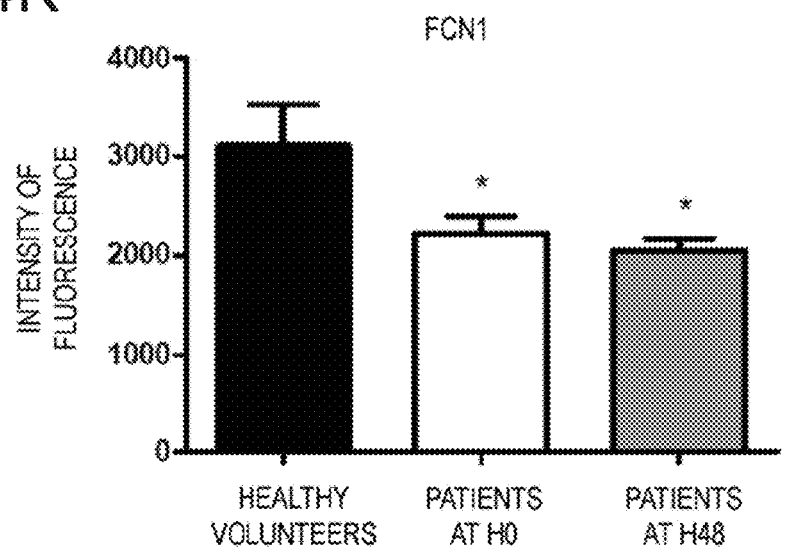
Figure 4L:
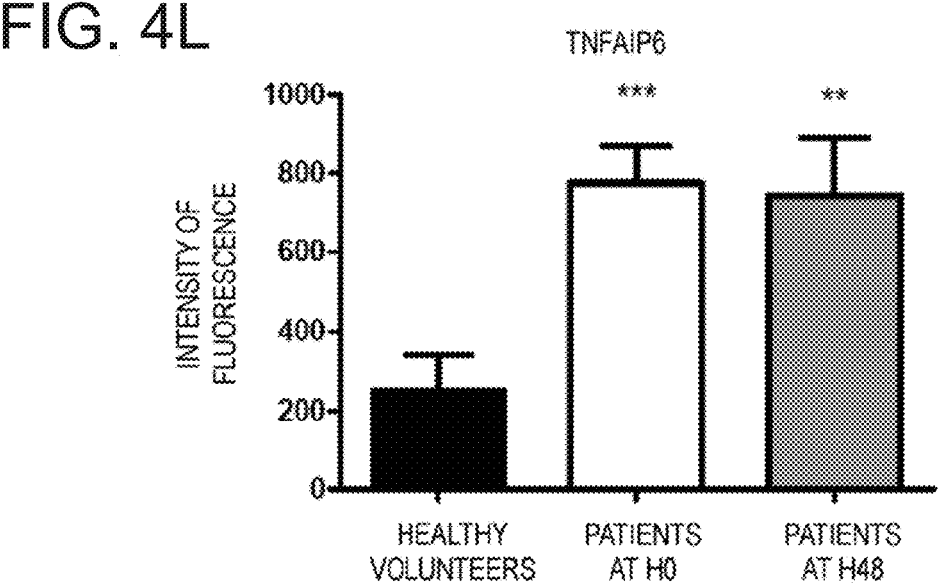
Figure 4M:
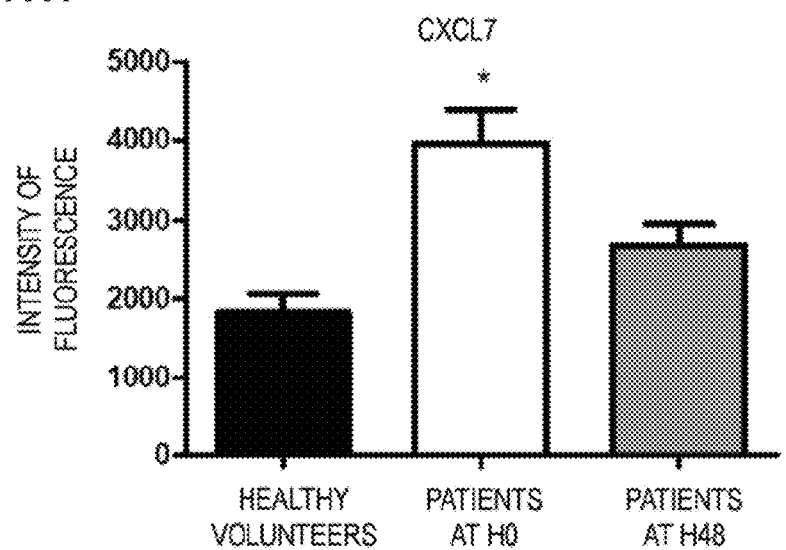
Figure 4N:
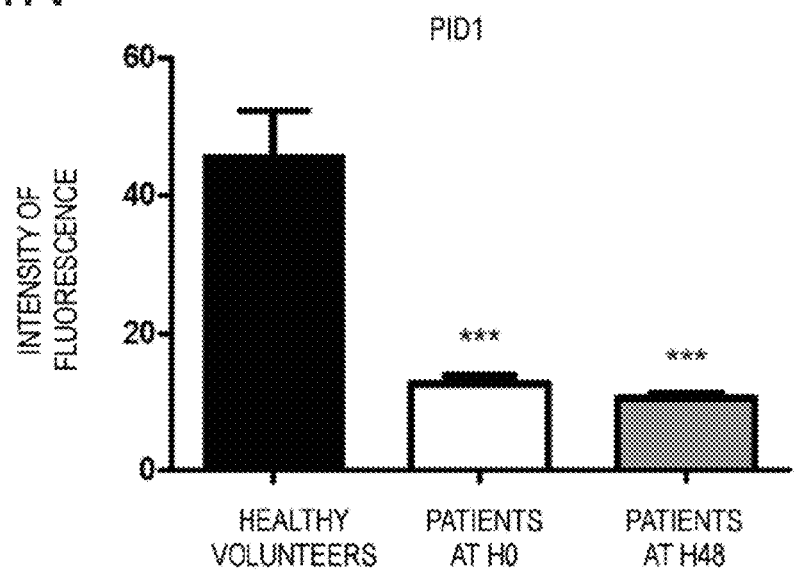
Figure 4O:
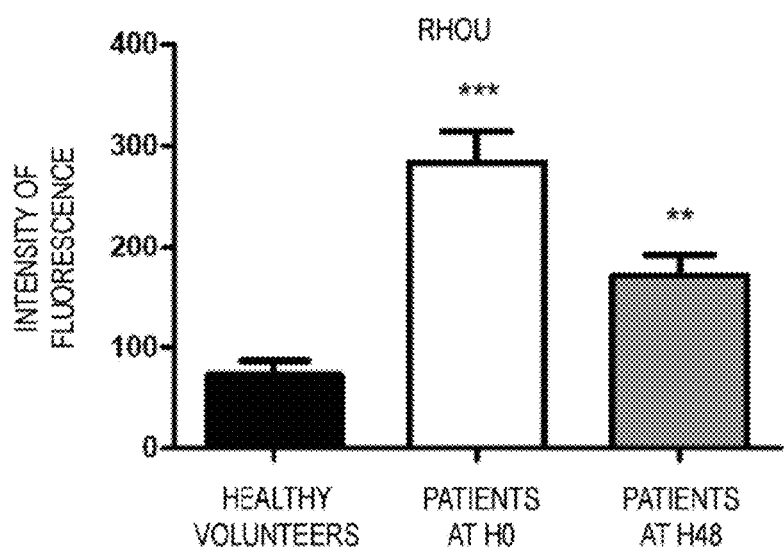

FIGS. 4A-4O respectively represent the expression of the IL-10 (A), IRAK-M (B), HLA-DRA (C), CIITA (D), TNF-α (E), LY64 (F), GBP1 (G), CXCL1 (H), CXCL10 (I), COX2 (J), FCN1 (K), TNFAIP6 (L), CXCL7 (M), PID1 (N) and RHOU (O) genes quantified by biochips from whole blood from 19 patients in septic shock, upon diagnosis of shock (HO) and 48 hours after (H48), or from blood from 9 healthy volunteers. The y axis represents the intensity of fluorescence of each of the hybridisation probes: (A) 207433_at for IL-10; (B) 213817_at for IRAK-M (C) 208894_at for HLA-DRA; (D) 205101_at for CIITA; (E) 207113_s_at for TNF-α; (F) 206206_at for LY64; (G) 202269_x_at for GBP1; (H) 204470_at for CXCL1; (I) 204533_at for CXCL10 (J); 204748_at for COX2 (K); 205237_at for FCN1 (L); 206026_s_at for TNFAIP6 (M); 214146_s_at for CXCL7 (N); 219093_at for PID1 and (O) 223168_at for RHOU. The black histograms represent the healthy volunteers, the white histograms correspond to patients at HO and the grey histograms represent the patients at H48. The data are represented as mean+/−standard deviation. The comparison between the healthy volunteers and the patients was performed by a Mann Whitney test (*, signifies that p<0.05; , signifies that p<0.01 and *, signifies that p<0.001).

Figure 5A:
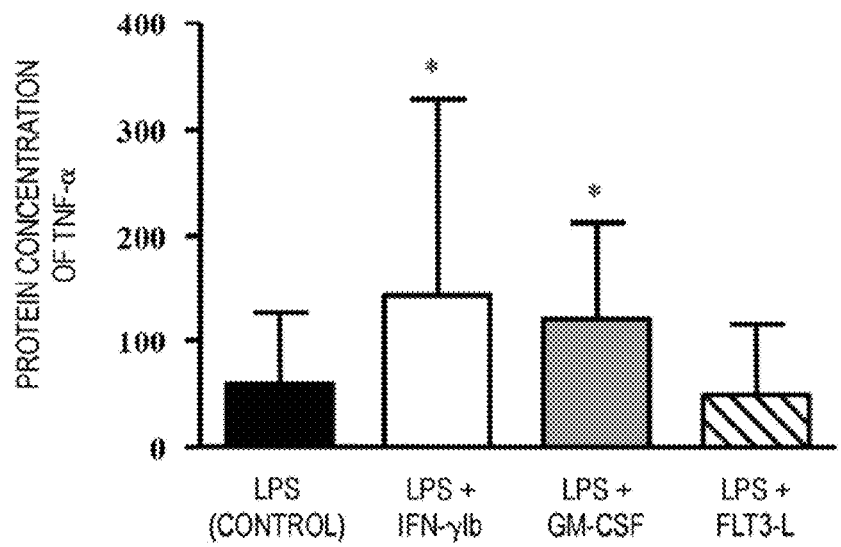
Figure 5B:
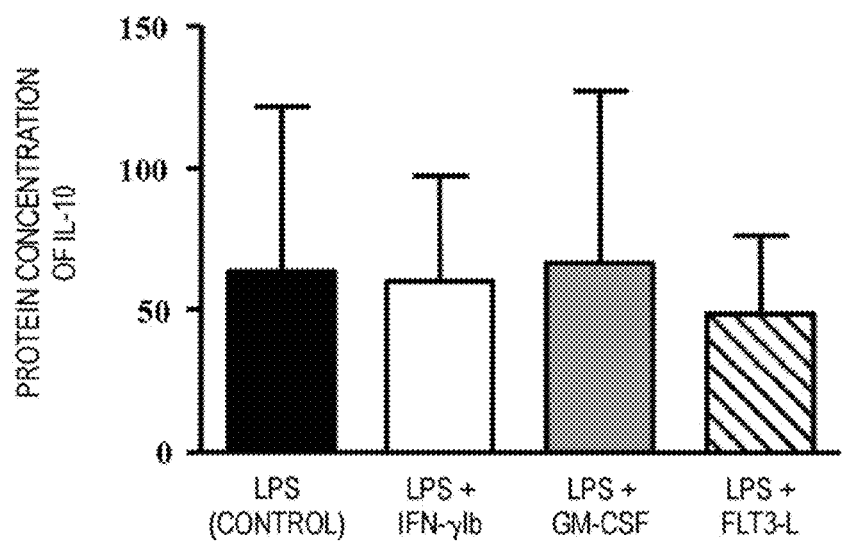

FIGS. 5A and 5B represent respectively the concentrations of TNF-α and IL-10 produced by PBMCs, from 10 healthy volunteers, stimulated twice by LPS (2 ng/ml then 100 ng/m1) in the presence of immunostimulants, or not. The assay was performed by an ELISA test on the culture supernatants obtained after 45 hours. The y axis represents the protein concentrations (pg/m1) of TNF α (FIG. 4A) and IL-10 (FIG. 4B). The black histograms represent the cells stimulated twice by LPS without drugs (control). The white histograms correspond to the cells stimulated twice by LPS in the presence of IFN-γ1b (Imukin™, Boehringer, Ingelheim, Austria) at 100 ng/ml, the grey histograms in the presence of 100 ng/ml of GM-CSF (Sigma-Aldrich, Deisenhofen, Germany) and the striped histograms in the presence of 100 ng/ml of FLT3-L (Sigma-Aldrich, Deisenhofen, Germany). The data are represented as mean+/−standard deviation. A Wilcoxon matched-pair test was performed for the statistical analysis of the results by correcting by the number of tests performed: *, signifies that p<0.017 vs. cells stimulated twice with LPS without drugs.

Figure 6A:
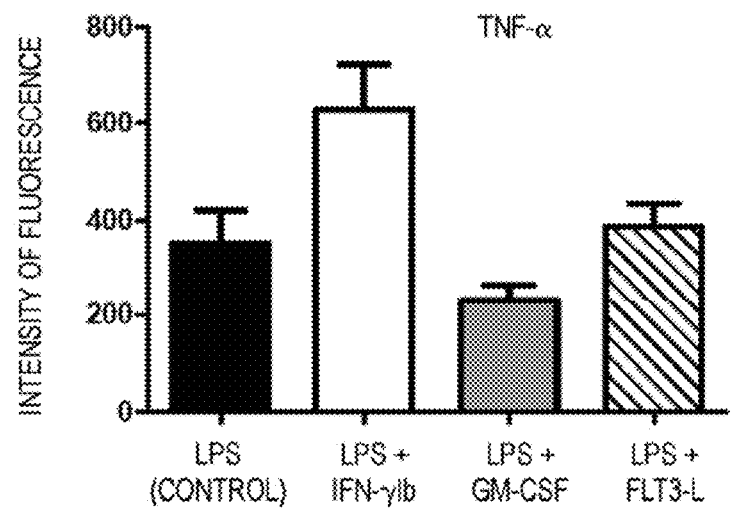
Figure 6B:
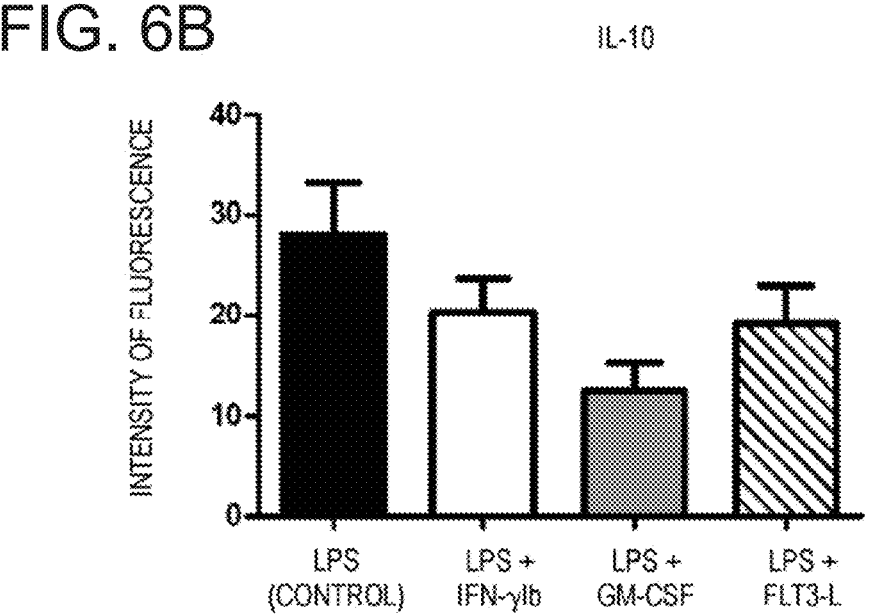
Figure 6C:
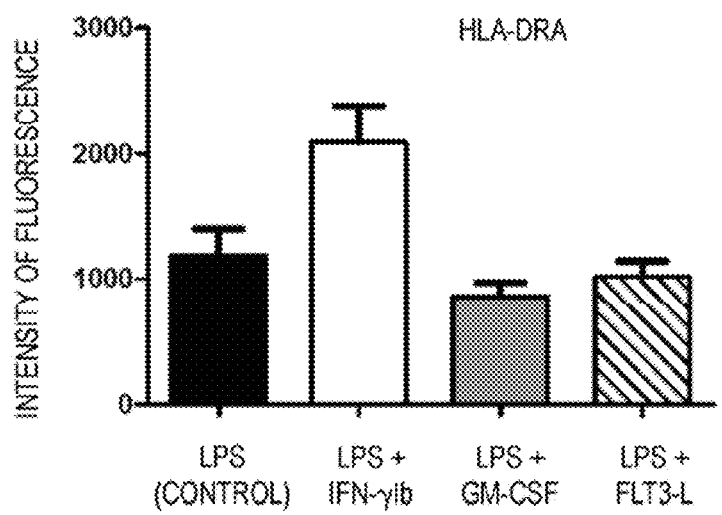
Figure 6D:
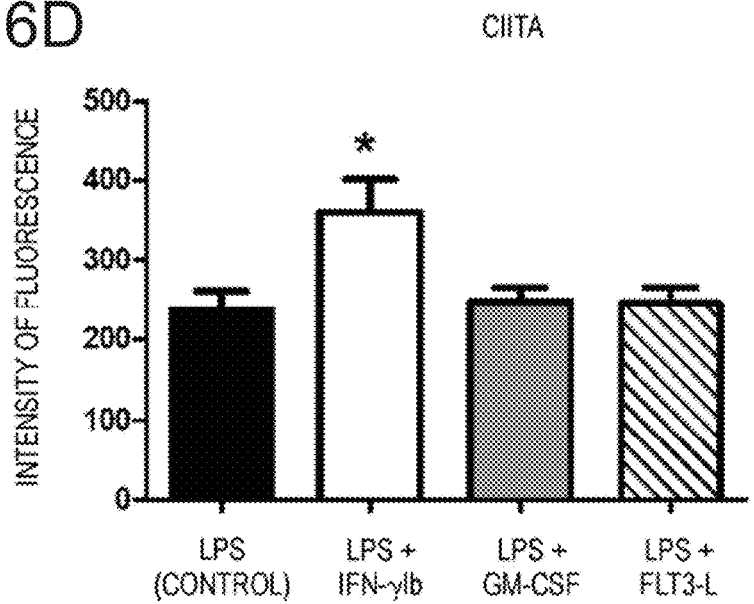
Figure 6E:
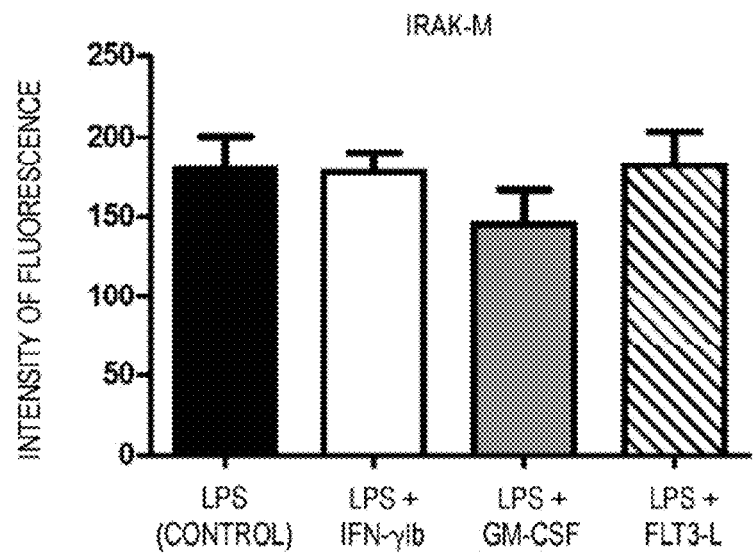
Figure 6F:
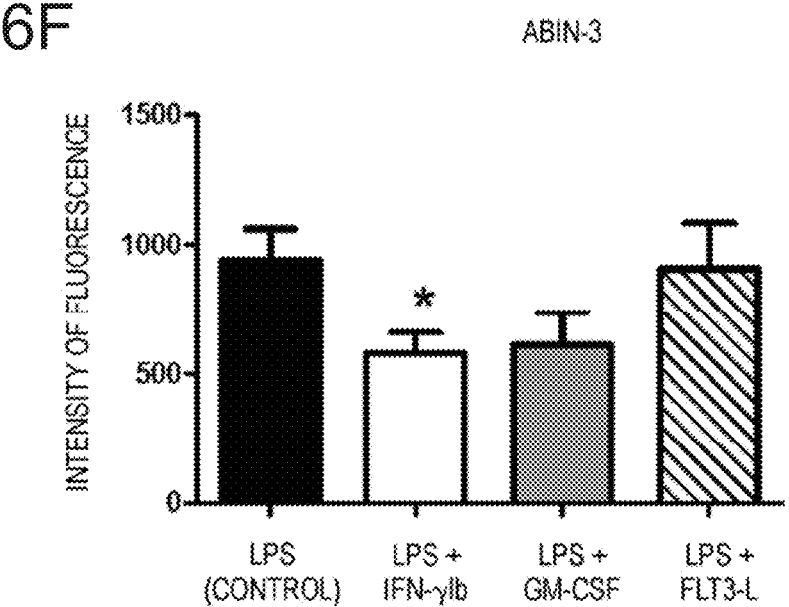
Figure 6G:
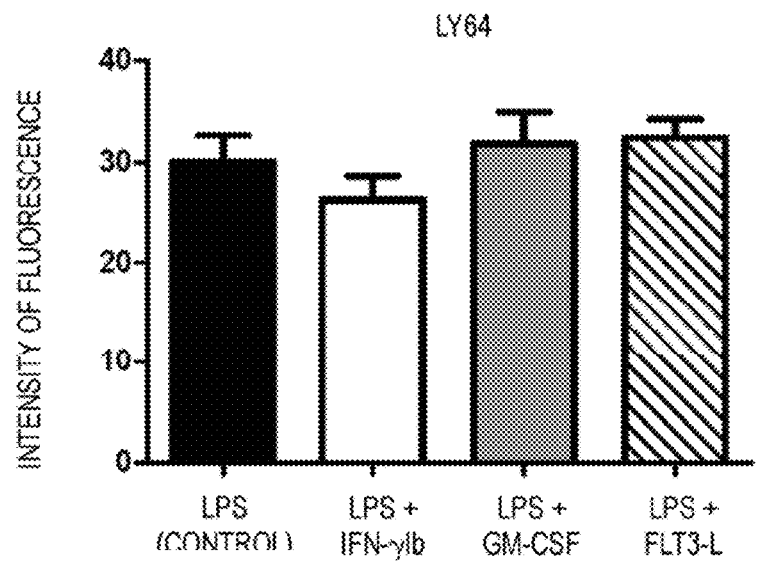
Figure 6H:
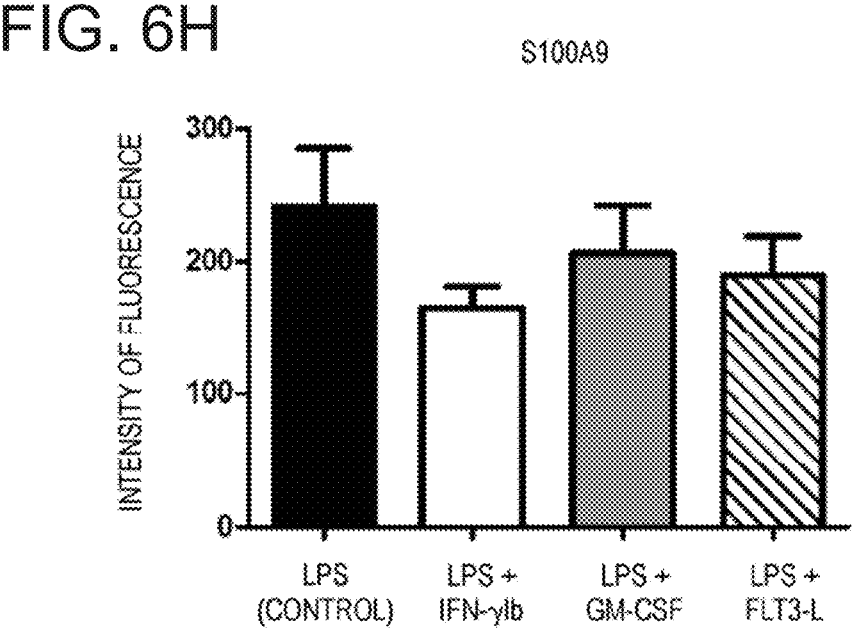
Figure 6I:
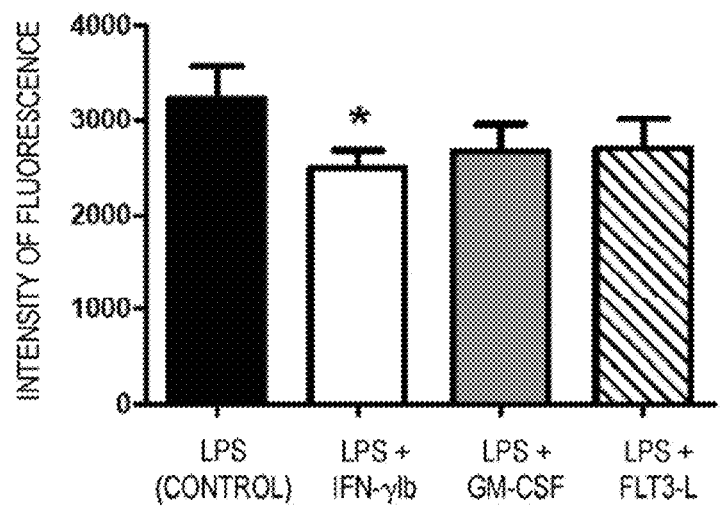
Figure 6J:
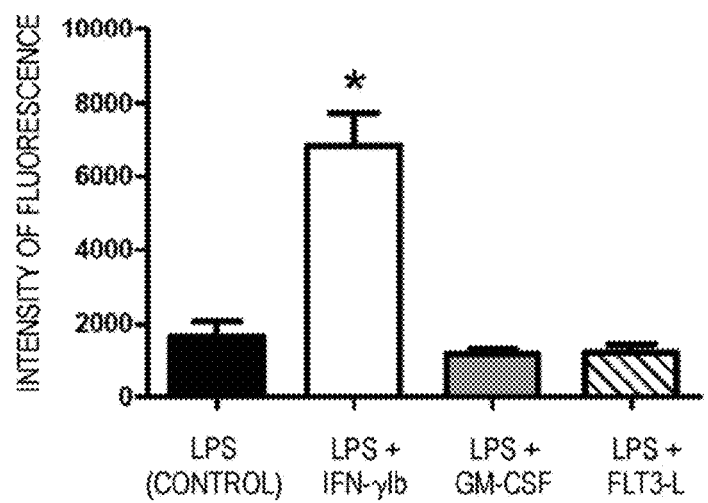
Figure 6K:
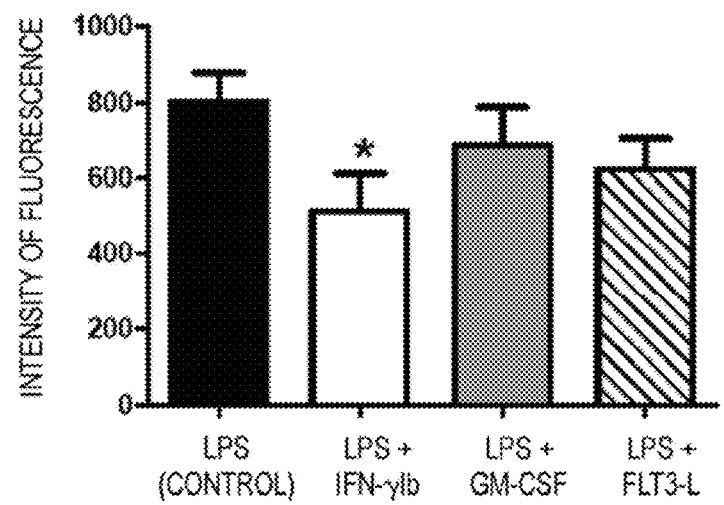
Figure 6L:
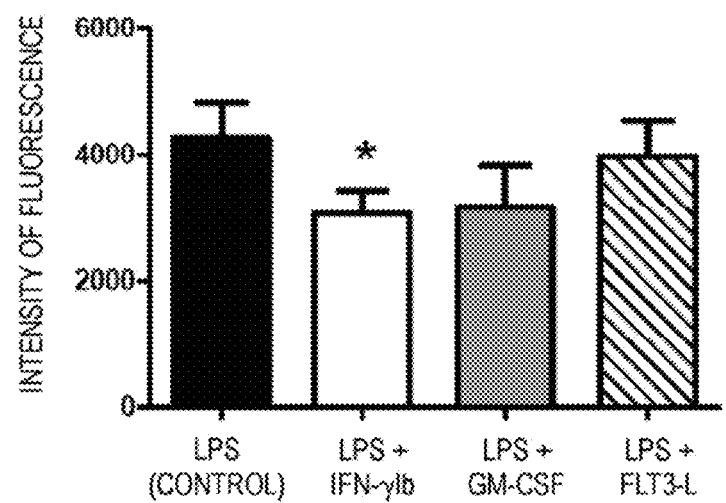
Figure 6M:
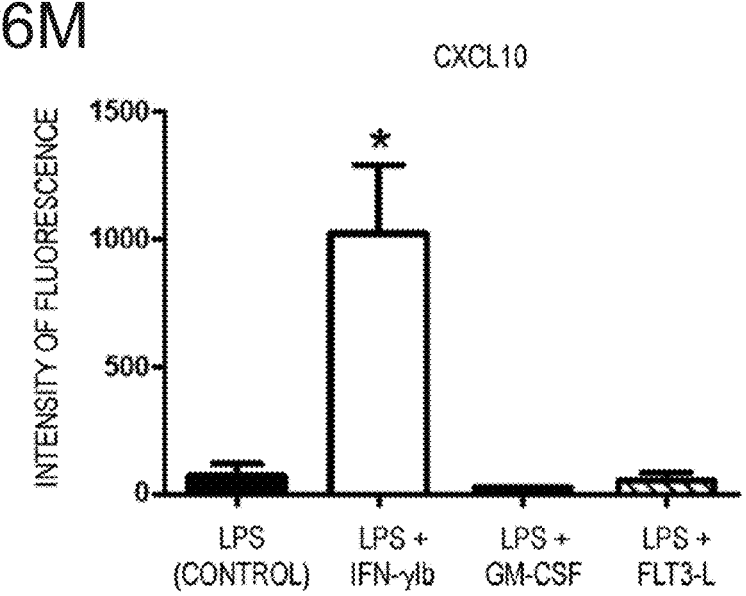
Figure 6N:
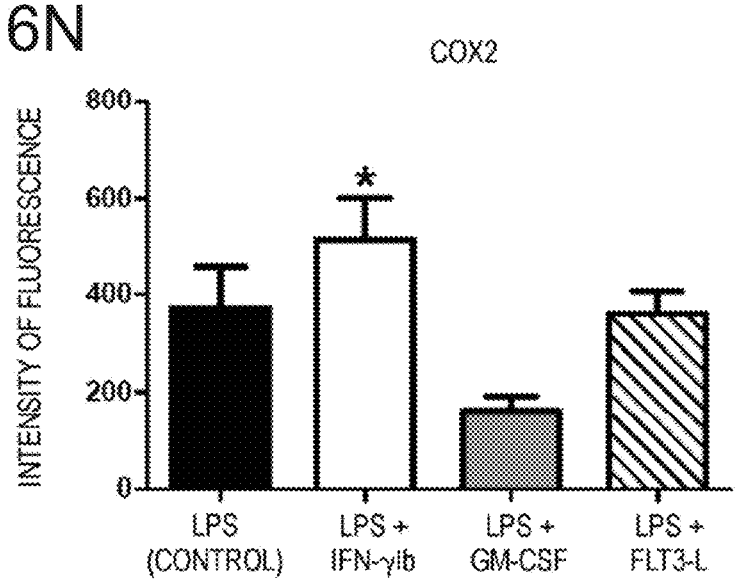
Figure 6O:
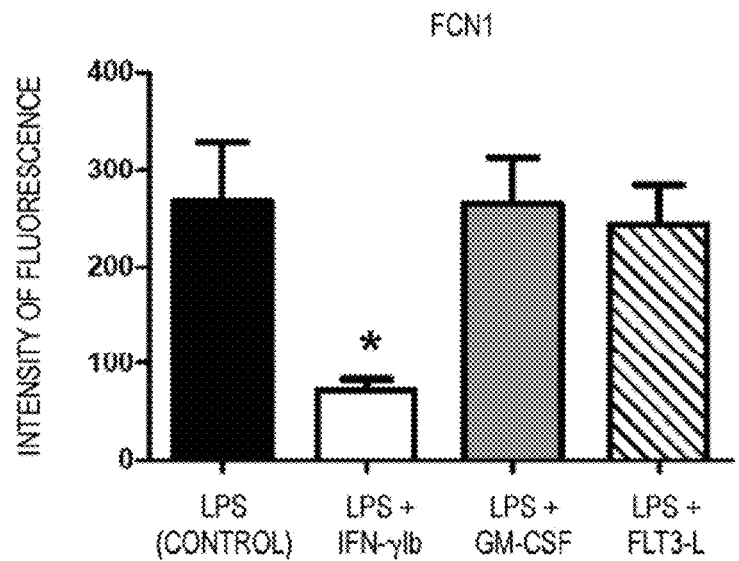
Figure 6P:
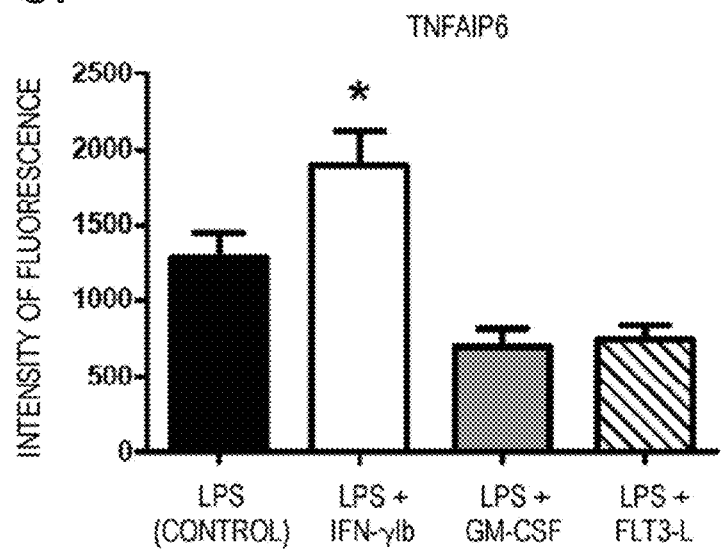
Figure 6Q:
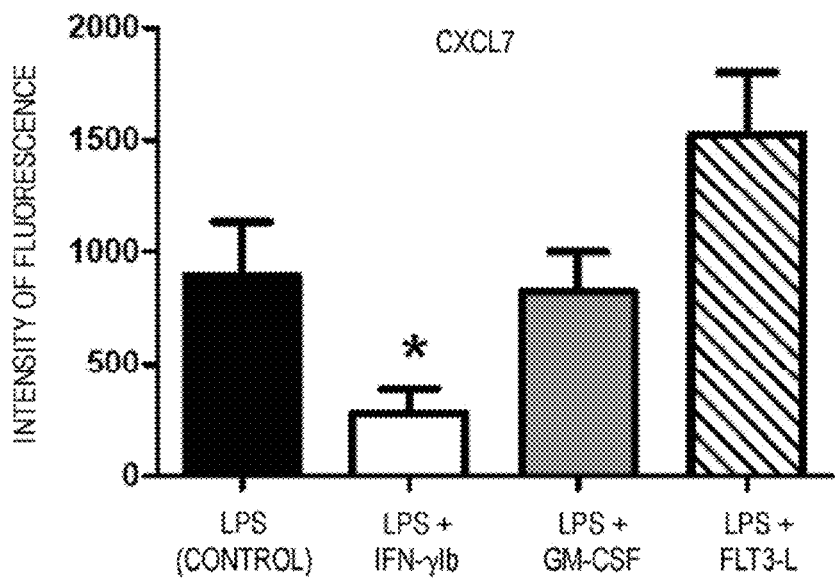
Figure 6R:
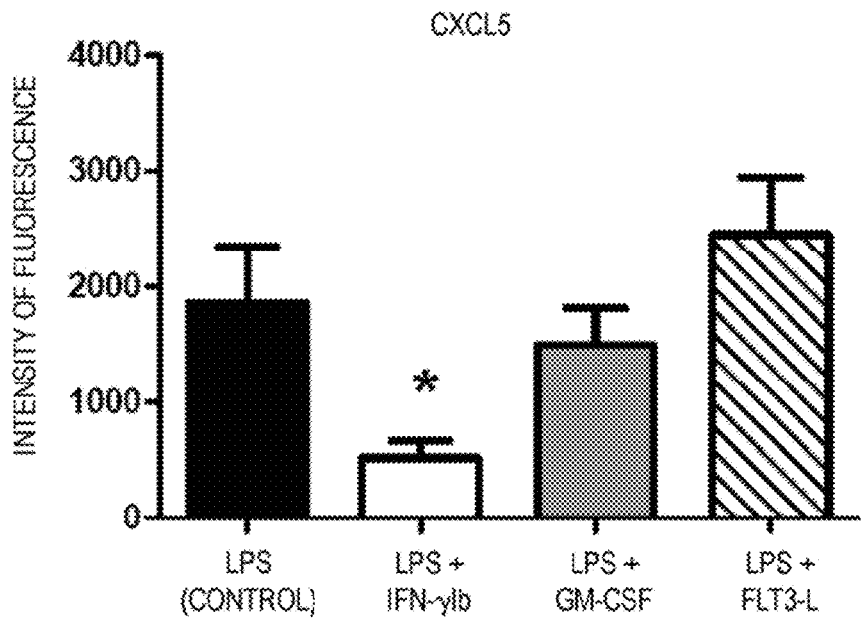
Figure 6S:
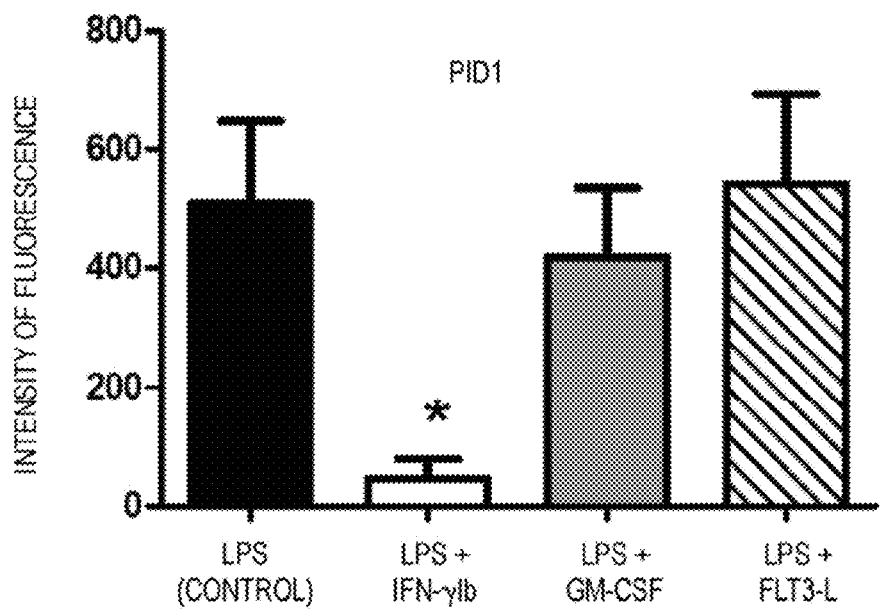
Figure 6T:
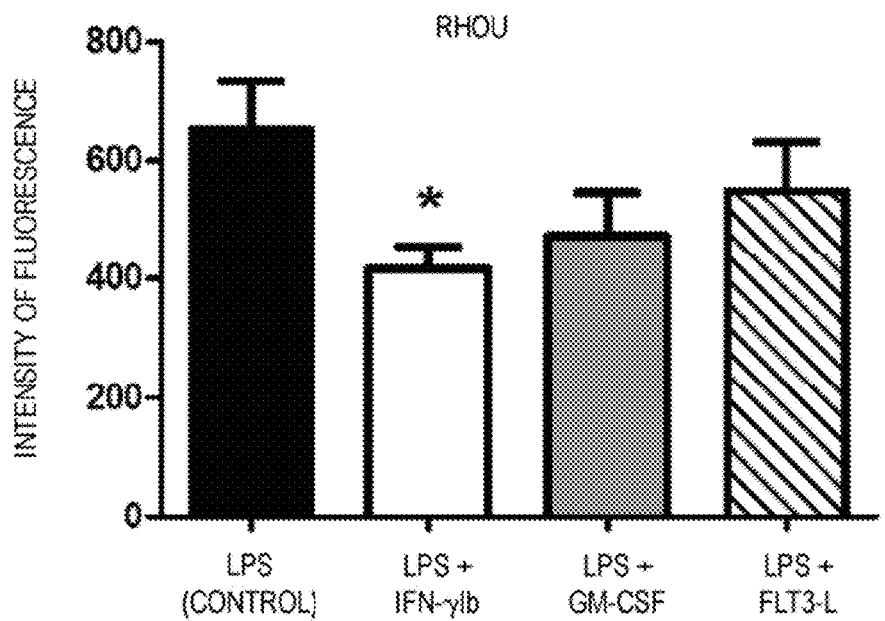

FIGS. 6A-6T respectively show the expression of the TNF alpha (A), IL-10 (B), HLA-DRA (C), CIITA (D), IRAK-M (E), ABIN-3 (F), LY64 (G), S100A9 (H), S100A8 (I), GBP1 (J), MMP7 (K), CXCL1 (L), CXCL10 (M), COX2 (N), FCN1 (O), TNFAIP6 (P), CXCL7 (Q), CXCL5 (R), PID1 (S) and RHOU (T) genes by PBMCs, which come from 7 healthy volunteers, stimulated twice by LPS (2 ng/ml and then 100 ng/m1) in the presence, or not, of drugs, and quantified by biochips after 45 hours. The y axis represents the intensity of fluorescence of each of the hybridisation probes: (A) 207113_s_at for the TNFa; (B) 207433_at for IL-10; (C) 208894_at for HLA-DRA; (D) 205101_at for CIITA; (E) 213817_at for IRAK-M; (F) 220655_at for ABIN-3; (G) 206206_at for LY64; (H) 203535_at for S100A9; (I) 202917_s_at for S100A8; (J) 202269_x_at for GBP1; (K) 204259_at for MMP7; (L) 204470_at for CXCL1; (M) 204533_at for CXCL10; (N) 204748_at for COX2; (O) 205237_at for FCN1; (P) 206026_s_at for TNFAIP6; (Q) 214146_s_at for CXCL7; (R) 215101_s_at for CXCL5; (S) 219093_at for PID1 and (T) 223168_at for RHOU. The black histograms represent the cells stimulated twice by LPS without drugs (control). The white histograms correspond to cells stimulated twice by LPS in the presence of IFN-γ1b at 100 ng/ml, the grey histograms in the presence of 100 ng/ml of GM-CSF and the striped histograms in the presence of 100 ng/ml of FLT3-L. The data are represented as mean+/−standard deviation. A matched-pair t-test was performed for the statistical analysis of the results by correcting by the number of tests performed: *, signifies that p<0.05 vs. cells stimulated twice with LPS without immunostimulants.

Figure 7A:
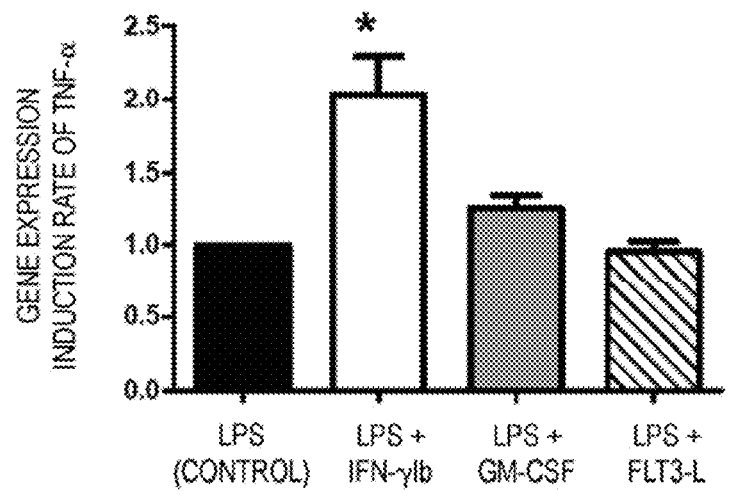
Figure 7B:
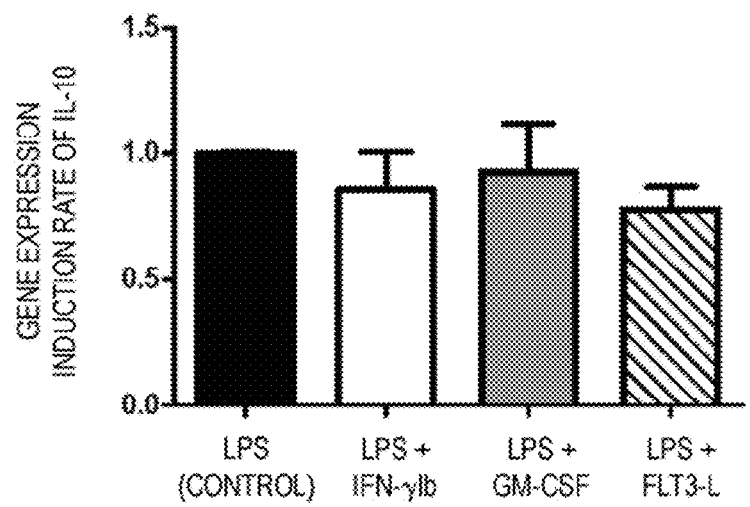
Figure 7C:
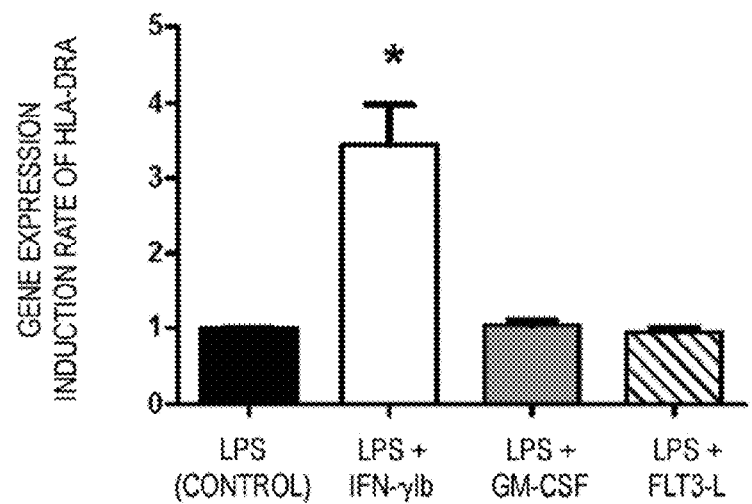
Figure 7D:
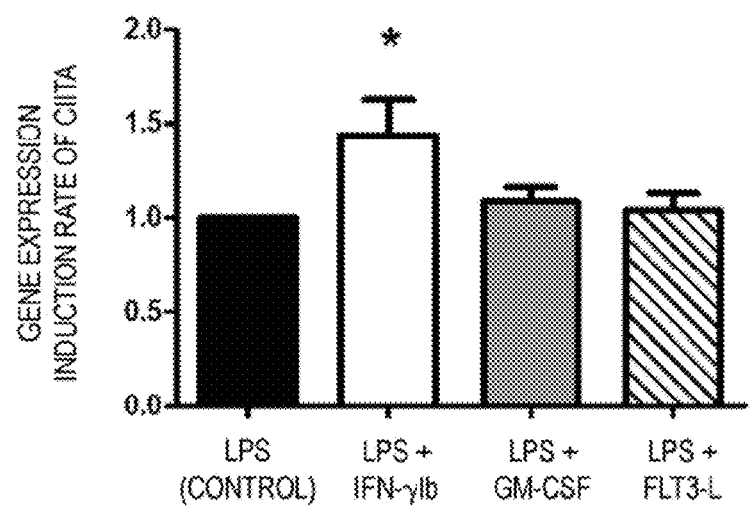
Figure 7E:
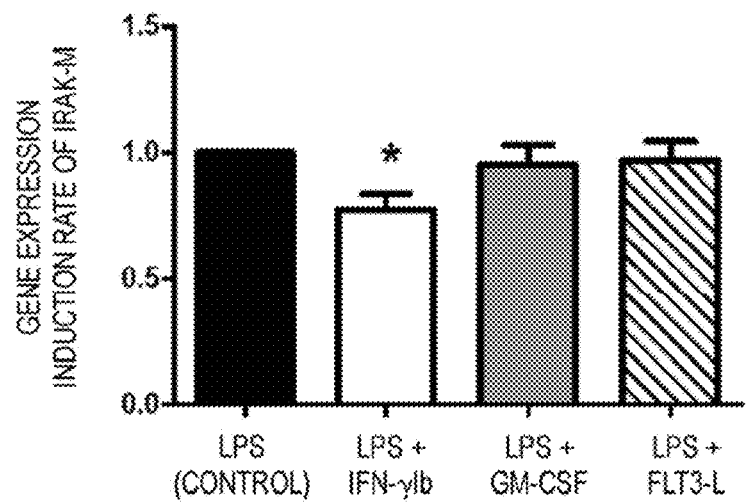
Figure 7F:
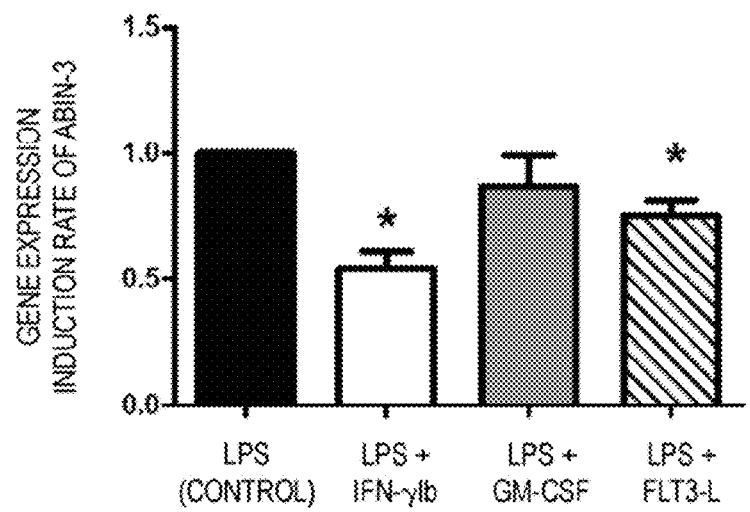
Figure 7G:
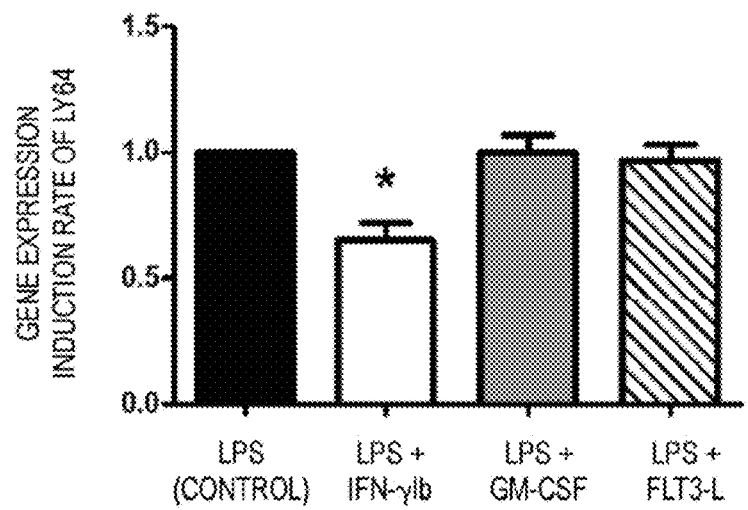
Figure 7H:
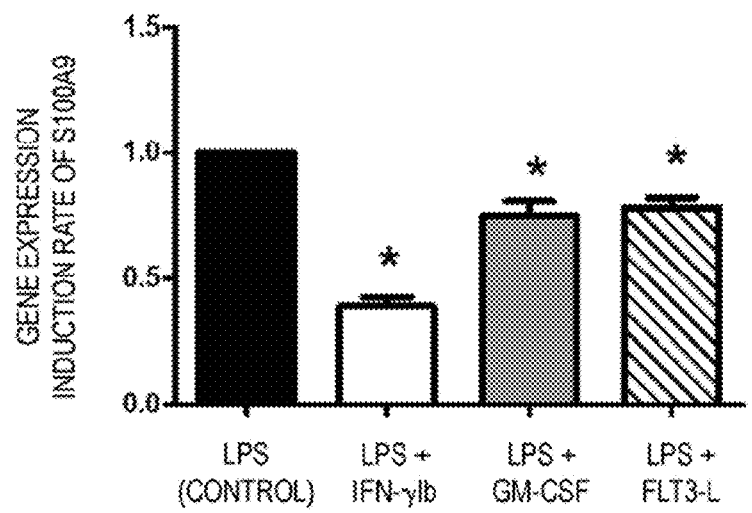
Figure 7I:
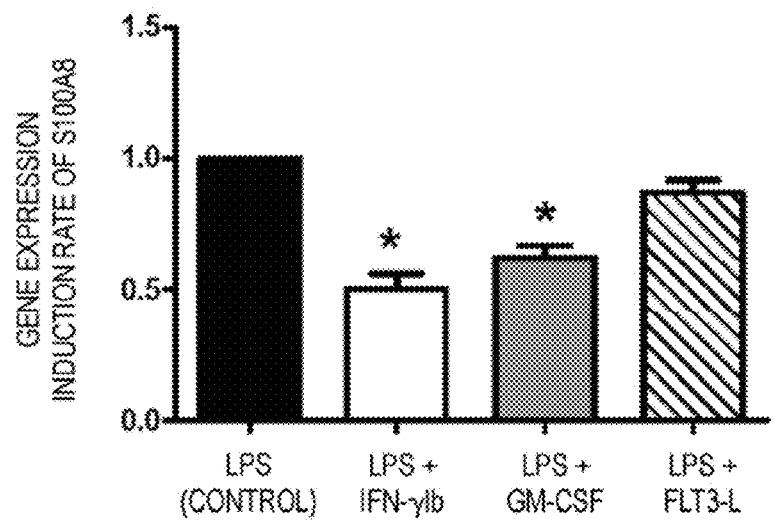
Figure 7J:
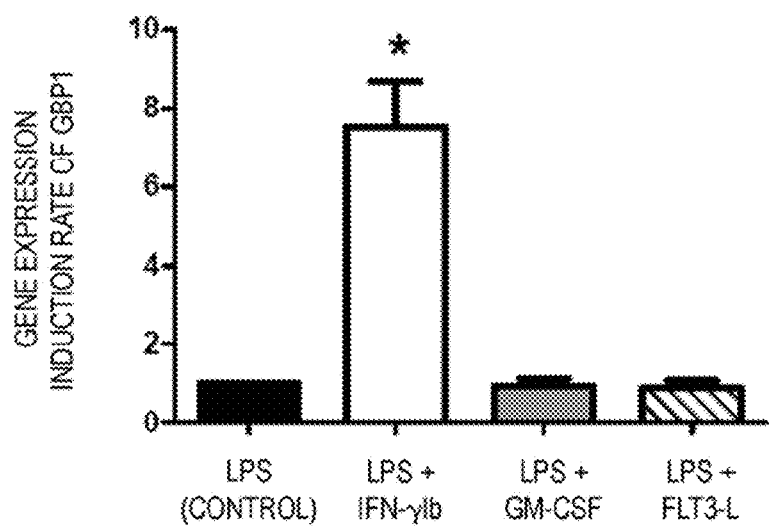
Figure 7K:
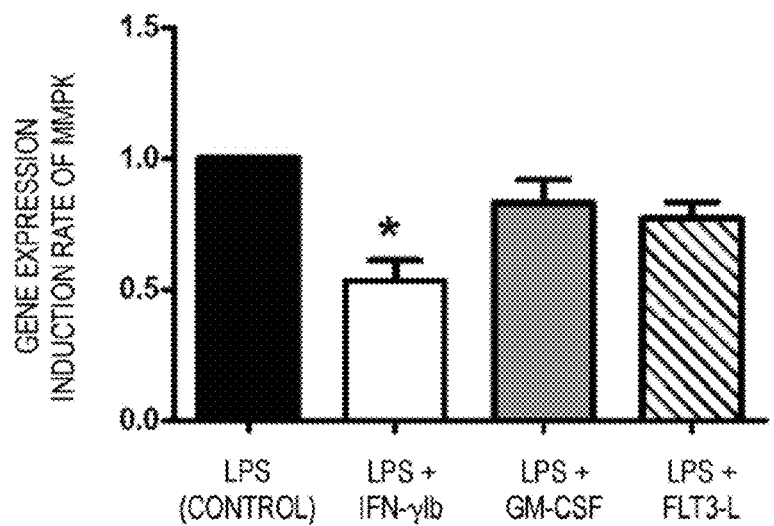
Figure 7L:
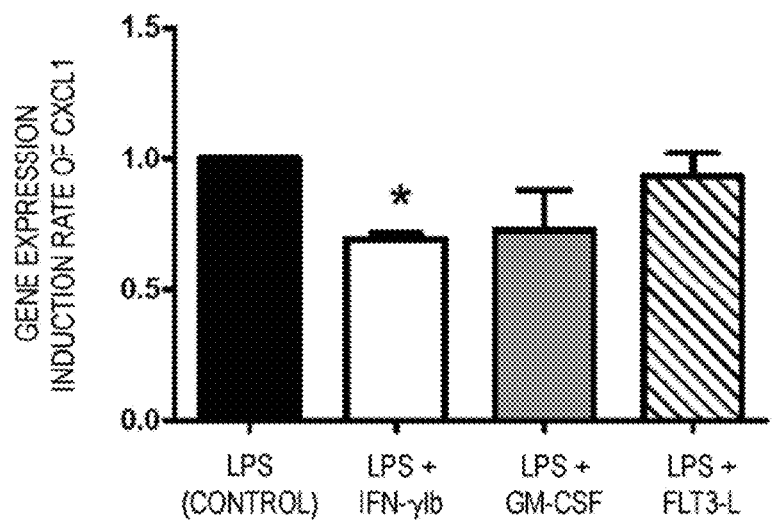
Figure 7M:
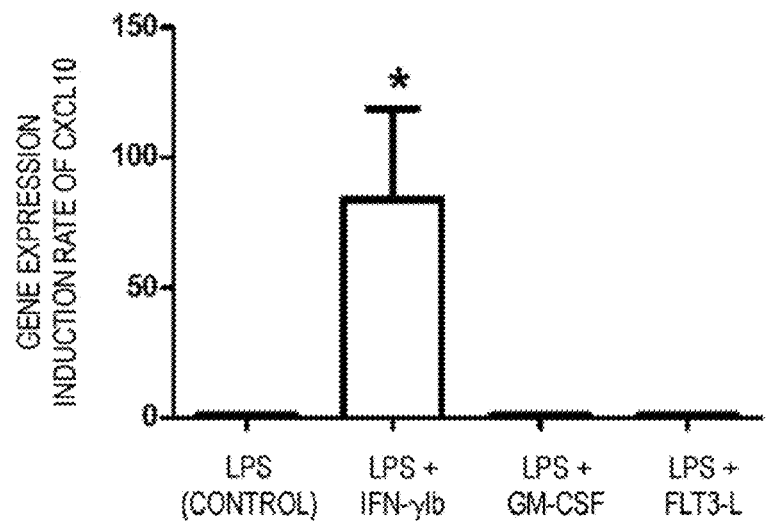
Figure 7N:
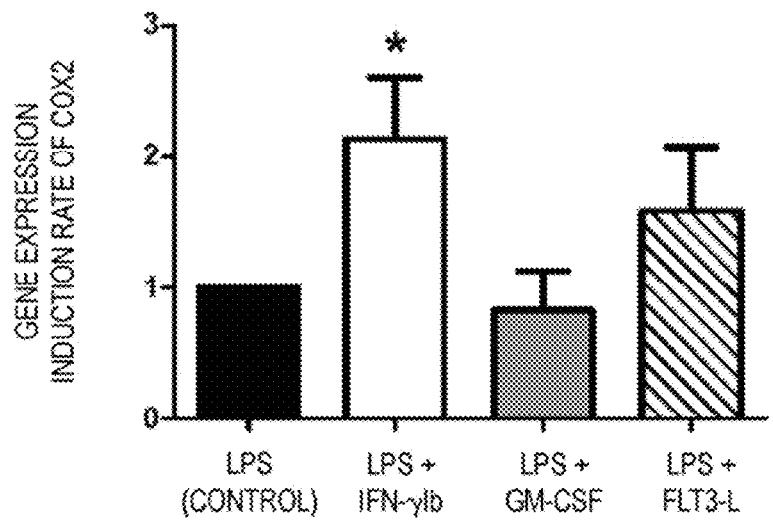
Figure 7O:
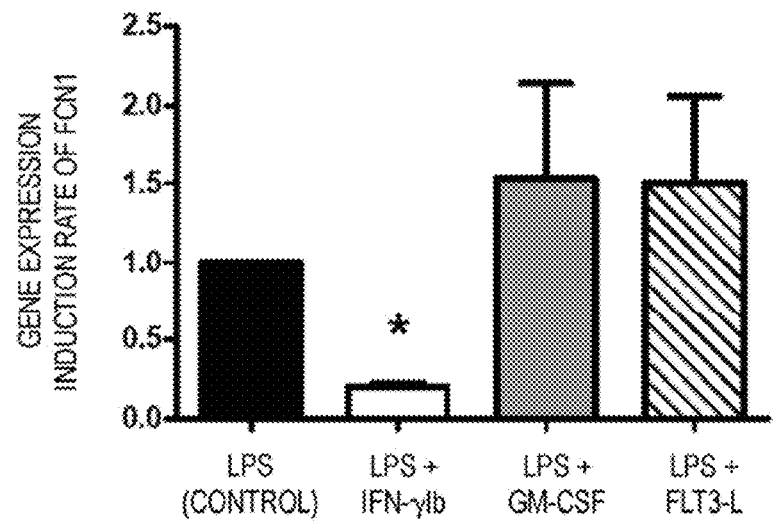
Figure 7P:
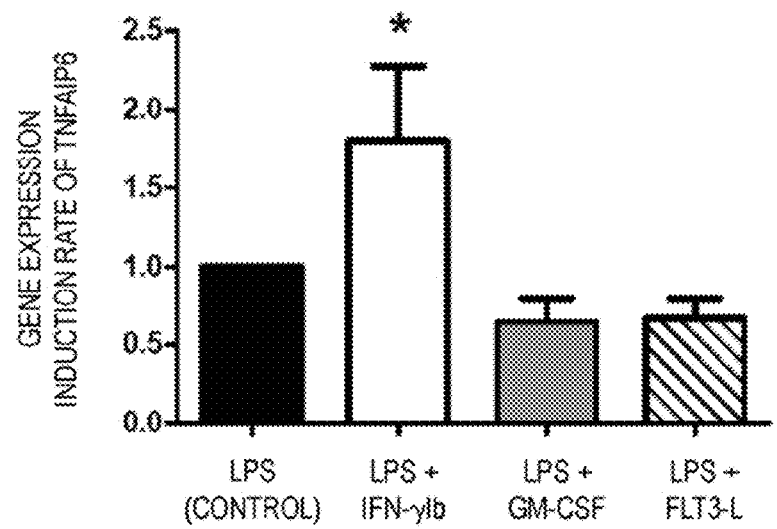
Figure 7Q:
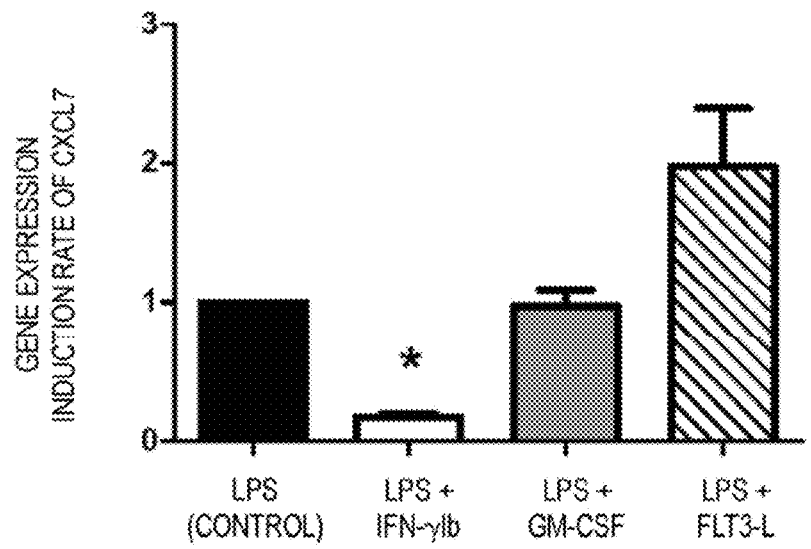
Figure 7R:
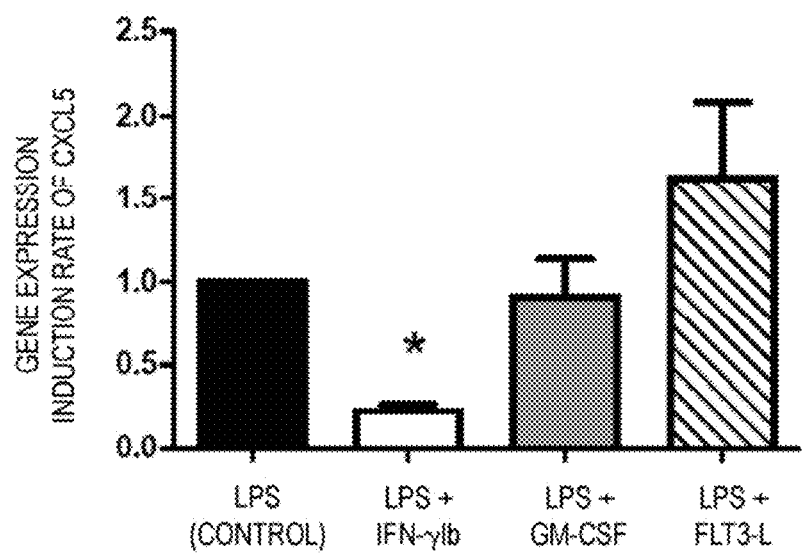
Figure 7S:
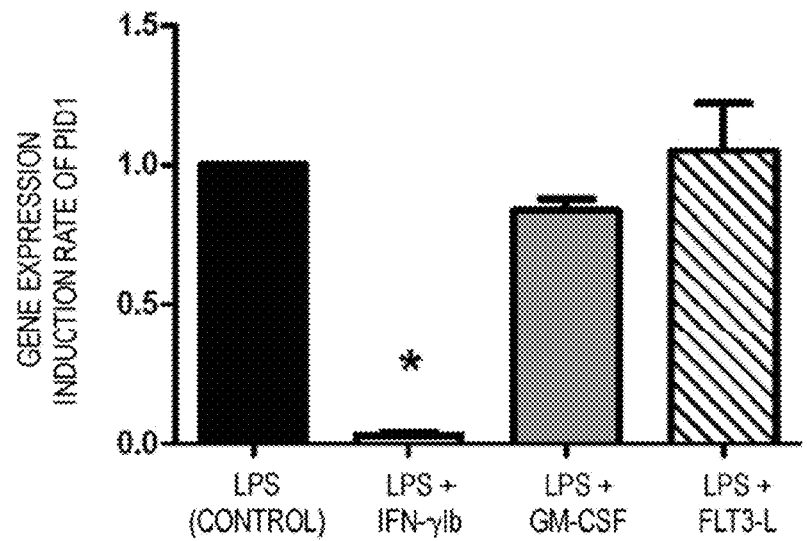
Figure 7T:
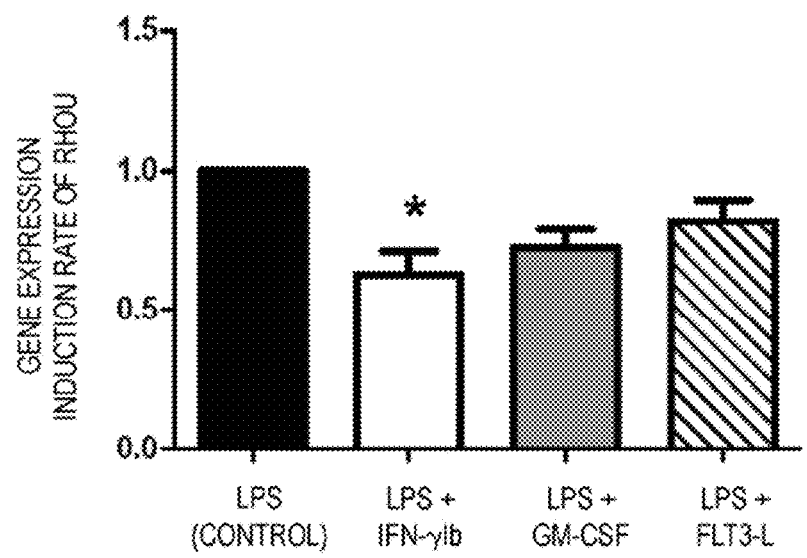

FIGS. 7A-7T respectively show the expression of the TNFa (A), IL-10 (B), HLA-DRA (C), CIITA (D), IRAK-M (E), ABIN-3 (F), LY64 (G), S100A9 (H), S100A8 (I), GBP1 (J), MMP7 (K), CXCL1 (L), CXCL10 (M), COX2 (N), FCN1 (O), TNFAIP6 (P), CXCL7 (Q), CXCL5(R), PID1 (S) and RHOU (T) genes by PBMCs, which come from 7 healthy volunteers, stimulated twice by LPS (2 ng/ml and then 100 ng/m1) in the presence, or not, of drugs, and quantified by qRT-PCR after 45 hours. The y axis represents the gene expression induction rates cited above. The black histograms represent the cells stimulated twice by LPS without drugs (control). The white histograms correspond to cells stimulated twice by LPS in the presence of IFN-γ1b at 100 ng/ml, the grey histograms in the presence of 100 ng/ml of GM-CSF and the striped histograms in the presence of 100 ng/ml of FLT3-L. The data are represented as mean+/−standard deviation. A Wilcoxon matched-pair test was performed for the statistical analysis of the results by correcting by the number of tests performed: *, signifies that p<0.05 vs. cells stimulated twice with LPS without immunostimulants.

Figure 8A:
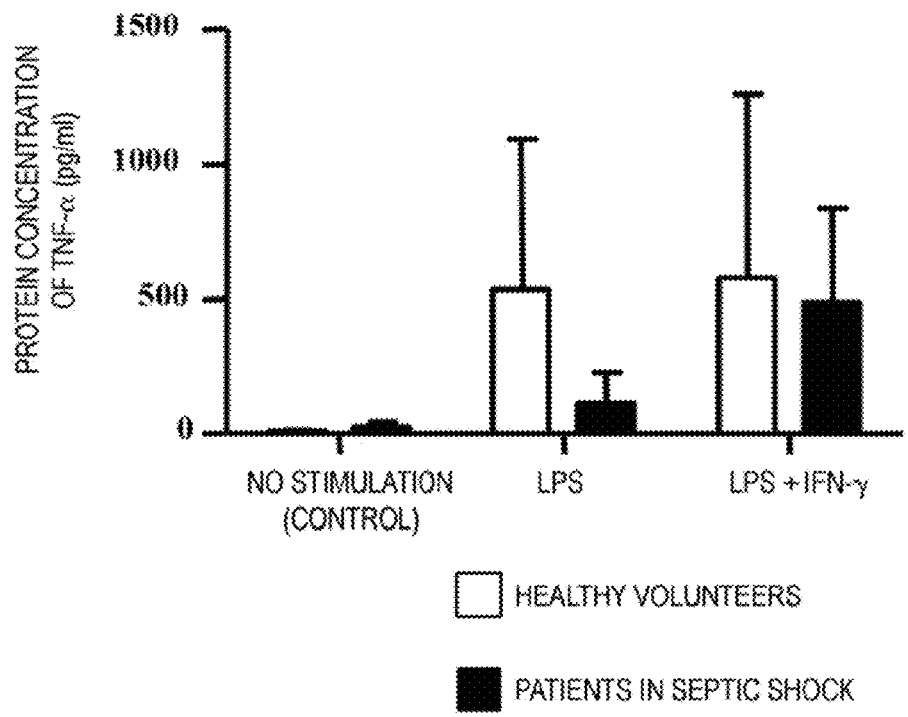
Figure 8B:
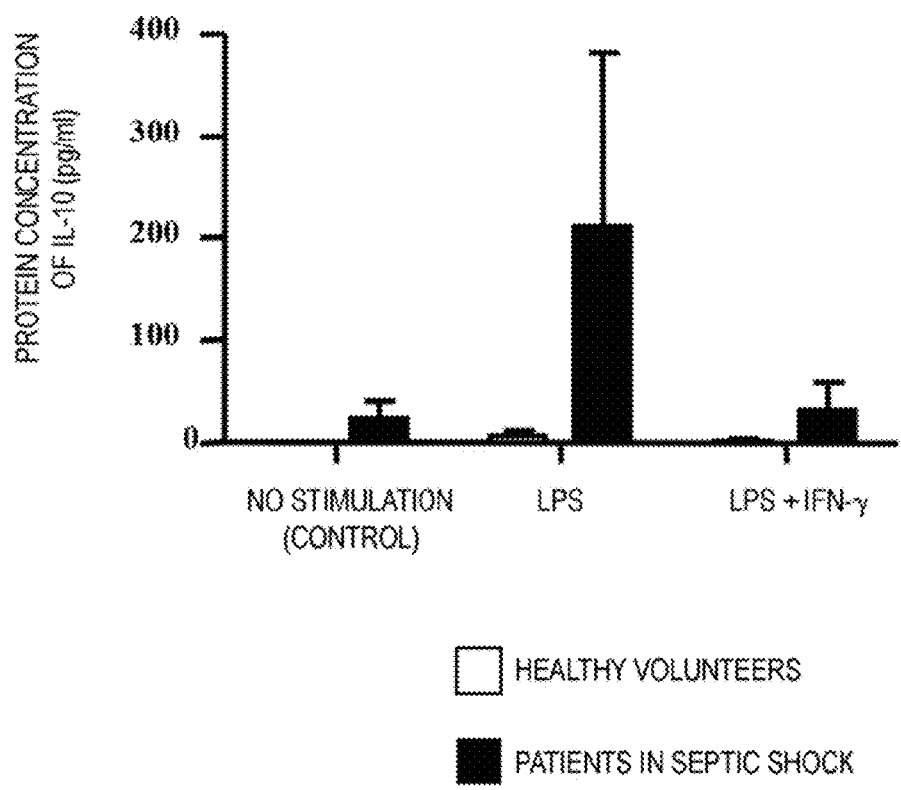

FIGS. 8A and 8B respectively represent the concentrations of TNF-α and IL-10 produced by whole blood cells, from 5 patients in septic shock sampled between D1 and D3 and 5 healthy volunteers, stimulated or not (control) by LPS at 100 ng/ml+/−100 ng/ml of IFN-γ1b. The protein assays were performed by an ELISA test on the culture supernatants obtained after 15 hours. The y axis represents the protein concentrations (pg/m1) of TNF-α (FIG. 6A) and IL-10 (FIG. 6B). The black histograms represent the patients in septic shock and the white histograms represent the healthy volunteers. The data are represented as mean+/− standard deviation.

FIGS. 9A-9I respectively represent the expression of the TNF-α (A), IL-10 (B), HLA-DRA (C), CIITA (D), GBP1 (E), CXCL10 (F), COX2 (G), TNFAIP6 (H) and CXCL5 (I) genes by whole blood cells, coming from 5 patients in septic shock sampled between D1 and D3 and 5 healthy volunteers, stimulated or not (controls) by LPS at 100 ng/ml+/−100 ng/ml of IFN-γ1b. The quantification of these genes was performed by qRT-PCR on the cell pellets obtained after 15 hours. The y axis represents the gene expression induction rates cited above. The black histograms represent the patients in septic shock and the white histograms represent the healthy volunteers.

EXAMPLES

The following examples are given by way of illustration and are in no way limiting. They will allow the invention to be better understood.

Materials and Methods

Preparation of the PBMCs and Experimental Parameters of the Endotoxin Tolerance (ET) Model The PBMCs from different healthy volunteers were isolated from sampled blood in pouches treated with citrate by Ficoll gradient (Amersham Biosciences, Björkgatan, Sweden), then washed with PBS while the remaining erythrocytes were lysed. The cells were cultured in 24-well plates at $2.10^6$ cells/ml in X-Vivo 20 medium (Lonza, Verviers, Belgium). In order to induce a first exposure to LPS, the PBMCs were cultured in the presence or in the absence (control group) of 2 ng/ml of a mixture of LPS from Escherichia coli 055:B5, 0127:B8 and 0111:B4 (Sigma-Aldrich, Deisenhofen, Germany) and incubated for one night (15 hours) at 37° C. and 5% $CO_2$. After washing, the cells were incubated for 24 more hours in the presence or in the absence (control group stimulated with LPS, or not) of IFN-γ1b (Imukin™, Boehringer, Ingelheim, Austria), of GM-CSF or of Flt3-L (Sigma-Aldrich). Finally, the cells were restimulated by a second dose of LPS at 100 ng/ml for 6 hours. The proteins TNF-α and IL-10 were assayed in these supernatants while the mRNA expression was quantified from cell pellets. In each condition, the supernatants and the cell pellets were recovered and kept at −80° C. for the ELISA assaying of the TNF-α and IL-10 proteins, and at −20° C. for the RNA extraction and the quantification by qRT-PCR.

Functional Test by ELISA

The concentrations of TNF-α and IL-10 in the culture supernatants of PBMCs was detected via the ELISA kits marketed by the company R&D Systems (Minneapolis, USA).

RNA Extraction

The total RNAs were extracted from the PBMCs using the RNeasy Plus Mini™ kit (Qiagen, Hilden, Germany) or from whole blood using the QIAamp RNA Blood Mini™ kit (Qiagen), in accordance with the manufacturer's instructions. For each RNA extraction, the residual genomic DNA was digested on the gDNA Eliminator (Qiagen)™ columns, and then the RNAs were eluted in 30 µl of an elution buffer. The RNA concentrations were measured for each sample with the aid of Qubit™ (Invitrogen, Carlsbad, Calif., USA), in accordance with the manufacturer's instructions.

Analysis by Biochip

The expression of the genes was analysed using 50 ng of RNA amplified with the WT-Ovation RNA Amplification System kit from Nugen (NuGEN Technologies, Inc., San Carlos, Calif., USA). The amplified RNA was hybridised on Affymetrix® HG-U133Plus 2.0 chips following the manufacturer's instructions (Affymetrix®, Santa Clara, Calif., USA). The analysis of the Affymetrix data commences with the capture of the image of the biochip by the GeneChip® 3000 scanner from Affymetrix. The data were then standardised by RMA (Robust Multiple-Array Average) (Irizarry RA, Biostatistics 2003). All of the data based on the signal intensity were used after standardisation.

Synthesis of the cDNA by Reverse Transcription (RT) and Analysis by Quantitative PCR (qPCR)

The expression of the messenger RNAs (mRNA) was quantified with the aid of qPCR. In brief, the cDNA were synthesised from 100 ng of whole RNA by means of a reverse transcription step by using the SuperScript® VILO™ system (Invitrogen). The PCR reactions were then performed on the LightCycler® 480 device using either the fluorescent label, SYBR Green I Master Mix, according to the manufacturer's instructions (Roche Molecular Biochemicals, Indianapolis, Ind., USA), or the Probes master mix, according to the manufacturer's instructions (Roche Molecular Biochemicals, Indianapolis, Ind., USA). For the amplification, the reaction volume was 20 µl, and the cycles comprised an initial denaturation step at 95° C. for 5 minutes (1 cycle), followed by 45 amplification cycles (20 seconds at 95° C., 15 seconds of hybridisation at 68-58° C. and 15 seconds of extension at 72° C.), a fusion curve at 95° C. for 1 second, 60° C. for 10 seconds and 95° C. for 5 minutes, and finally a cooling to 40° C. for 30 seconds. Twenty genes were quantified in this study: TNF-α, l'IL-10, HLA-DRA, CIITA, CX3CR1, IRAK-M, ABIN-3, LY64, S100A9, S100A8, GBP1, MMP7, CXCL1, CXCL10, COX2, FCN1, TNFAIP6, CXCL7, CXCL5, PID1 and RHOU. The primers and/or probes used were either optimised by the company Search-LC (Search-LC, Heidelberg, Germany), for the housekeeping gene PPIB, encoding for cyclophilin B and TNF-α, or by the company Applied Biosystems (Life Technologies Corporation, Carlsbad, Calif., USA) for the genes GBP1 (reference Hs00977005_m1), MMP7 (ref.: Hs01042796_m1), CXCL1 (ref.: Hs00236937_m1), CXCL10 ref.: Hs00171042_m1), COX2 (ref.: Hs00153133_m1), FCN1 (ref.: Hs00157572_m1), TNFAIP6 (ref.: Hs01113602_ml, CXCL7 (ref.: Hs00234077_m1), CXCL5 (ref.: Hs00171085_m1), PID1 (ref.: Hs00952182_m1) and RHOU (ref.: Hs00221873_m1) and for the housekeeping gene PPIB (ref.: Hs00165719_m1), or, internally, for the other genes studied (IL-10, HLA-DRA, CIITA, CD180 (LY64), IRAK-M, ABIN-3, S100A9 and S100A8) (see the table below). Several cDNA dilutions were prepared in quadruplicate to generate the standard ranges. The results were standardised relative to the reference gene (PPIB) as well as an internal calibrator in order to minimise the impact of the manipulator and the efficiency of the different enzymes. The results were expressed as standardised ratio "fold change" and were only included in the analysis when the mRNA values were within the standard range of each of the genes studied.

TABLE

| Gene | GenBank Accession No. | Primers: | | SEQ ID NOs |
|---|---|---|---|---|
| IL-10 | NM_000572.2 | 5'-AATAAGGTTTCTCAAGGGGCT-3' | sense | 1 |
| | | 5'-AGAACCAAGACCCAGACATCAA-3' | anti-sense | 2 |
| HLA-DRA | NM_019111.4 | 5'-GCCAACCTGGAAATCATGACA-3' | sense | 3 |
| | | 5'-AGGGCTGTTCGTGAGCACA-3' | anti-sense | 4 |
| CIITA | NM_000246.3 | 5'-GCTGGGATTCCTACACAATGC-3' | sense | 5 |
| | | 5'-CGGGTTCTGAGTAGAGCTCAATCT-3' | anti-sense | 6 |
| IRAK-M | NM_007199.2 | 5'-TTTGAATGCAGCCAGTCTGA-3' | sense | 7 |
| | NM_001142523.1 | 5'-AGGGCTGTTCGTGAGCACA-3' | anti-sense | 8 |
| ABIN-3 | NM_024873.4 | 5'-GAATTCCCAGATAAAAGCTTGT-3' | sense | 9 |
| | NM_001128843.1 | 5'-GACAGTCTGGTGGGTGCTC-3' | anti-sense | 10 |
| S100A9 | NM_002965.3 | 5'-TCAAAGAGCTGGTGCGAAAA-3' | sense | 11 |
| | | 5'-AACTCCTCGAAGCTCAGCTG-3' | anti-sense | 12 |
| S100A8 | NM_002964.4 | 5'-ATTTCCATGCCGTCTACAGG-3' | sense | 13 |
| | | 5'-CACCAGAATGAGGAACTCCT-3' | anti-sense | 14 |
| LY64 | NM_005582.2 | 5'-GCATTGAGAAAGAAGCCAACAA-3' | sense | 15 |
| | | 5'-GAAAAGTGTCTTCATGTATCC-3' | anti-sense | 16 |

Transcriptional approach on biochip in patients in septic shock

Several blood samples collected directly in PAXgene™ tubes (PreAnalytiX a Qiagen/BD Company) were obtained from 19 patients in septic shock at the moment of the diagnosis of shock (i.e. in the 2 hours following the start of the vasopressor treatment) and 48 hours after, as described previously [9]. The whole RNA was extracted with the aid of the PAXgene Blood RNA Kit™ (PreAnalytix). A digestion step with DNAse (Qiagen) was performed during the extraction in order to eliminate all traces of DNA. The integrity and the quality of the RNAs were verified by capillary electrophoresis on the 2100 Agilent™ (Agilent) bioanalyser. The biochips were implemented according to the manufacturer's instructions (Affymetrix®). The reverse transcription reaction of the mRNAs was performed with the Affymetrix protocol using 3 µg of whole RNA. An oligonucleotide polyT primer was used to target solely the mRNA contained in the solution of whole RNAs during the reverse transcription. All of the steps were performed with the Affymetrix-GeneChip® One-Cycle Target Labeling and Control Reagents kit. The products of the reverse transcription (cDNA) were then used for the synthesis of biotin-labelled RNA for 16 hours at 37° C. After the cRNA purification step for removing the unincorporated dNTP, the cRNAs were quantified and fragmented. The fragmentation is controlled by capillary electrophoresis (Agilent). The hybridisation of the cRNA is performed with the GeneChi-pHuman Genome U133 Plus 2 biochip before the signal amplification step by incubation with the SAPE mixture containing Streptavidin Phycoerythrin, then the anti-streptavidin goat IgG antibody mixed with the biotinylated anti-goat IgG antibody. This last step uses the Fluidic FS450 platform. The analysis of the Affymetrix data commences with the image capture from the biochip by the GeneChip® 3000 scanner by Affymetrix. The data were then standardised by RMA (Robust Multiple-Array Average) (Irizarry RA, Biostatistics 2003). All of the data based on the signal intensity were used after standardisation.

Effect of IFN-γ in a Model of Whole Blood of Patients in Septic Shock

The blood of 5 patients in septic shock was collected in an EDTA tube, between D1 and D3 following the start of the shock, as well as from 5 healthy volunteers. After centrifuging and withdrawal of the plasma, 3 ml of blood were diluted by ½ in 3 ml of RPMI 1640 medium (Eurobio, Courtaboeuf, FRANCE) then cultured in the presence or in the absence (control group) of 100 ng/ml of LPS+/−100 ng/ml of IFN-γ1b (Imukin) for one night at 37° C. and 5% $CO_2$ (15 hours). In each condition, the supernatants and the cell pellets were recovered and kept at −80° C. for the ELISA assaying of TNF-α and IL-10, and at −20° C. for the RNA extraction and the quantification by qRT-PCR, as described previously.

Statistical Analyses

The results are expressed as mean±standard deviation (SD). The statistical analysis was performed by the Wilcoxon matched-pair test.

Results

Description of the ET Model

Figure 1A:
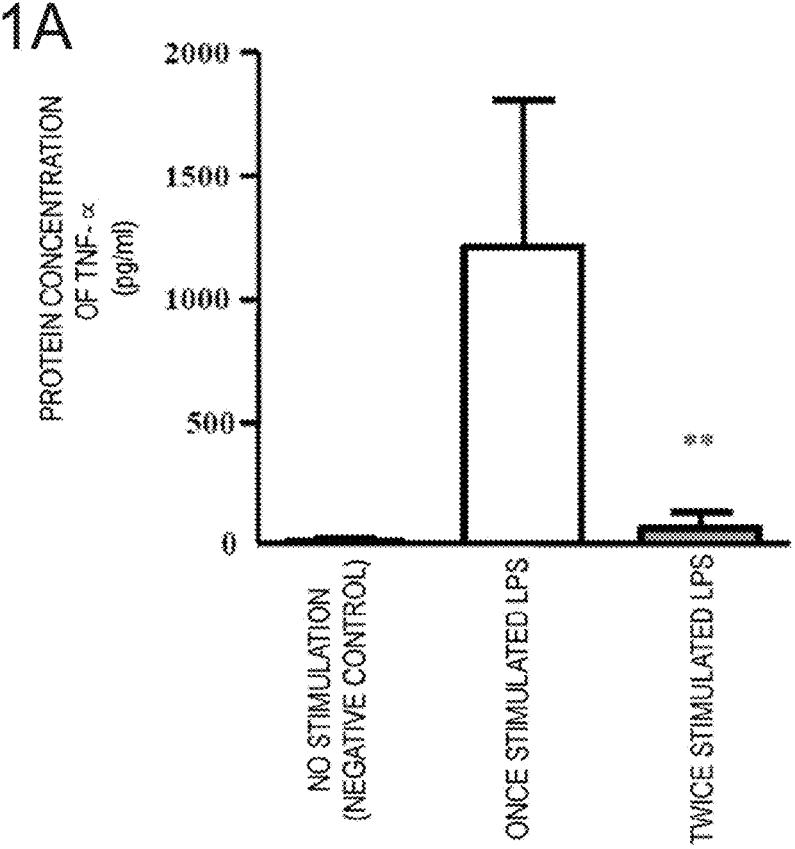
FIGS. 1A and 1B respectively represent the concentrations of TNF-α and IL-10 produced by PBMCs, coming from 10 healthy volunteers, stimulated by LPS. The assay was performed by an ELISA test on the culture supernatants obtained at 45 hours. The y axis represents the protein concentrations (pg/ml) of TNF-α (FIG. 1A) and IL-10 (FIG. 1B). The black histograms show the negative controls (without stimulation). The white histograms correspond to the cells stimulated just once with 100 ng/mL of LPS, and the grey histograms show the cells subjected to two stimulations by LPS (2 ng/ml then 100 ng/m1). The data are represented as mean+/−standard deviation. A Wilcoxon matched-pair test was performed for the statistical analysis of the results: **, signifies that p<0.005 vs. cells stimulated once with LPS.
Figure 1B:
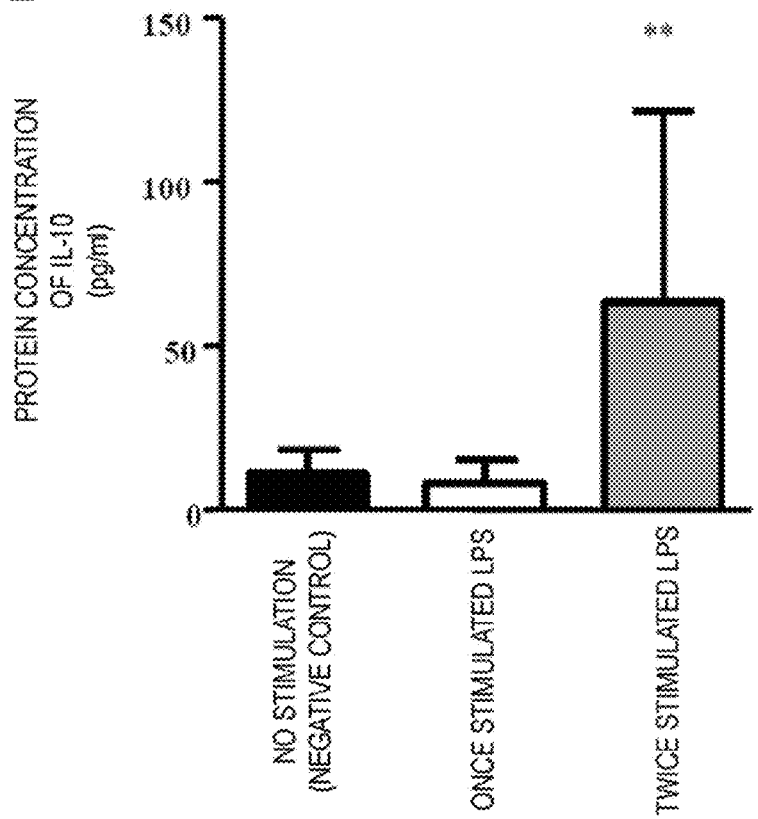
Figure 2A:
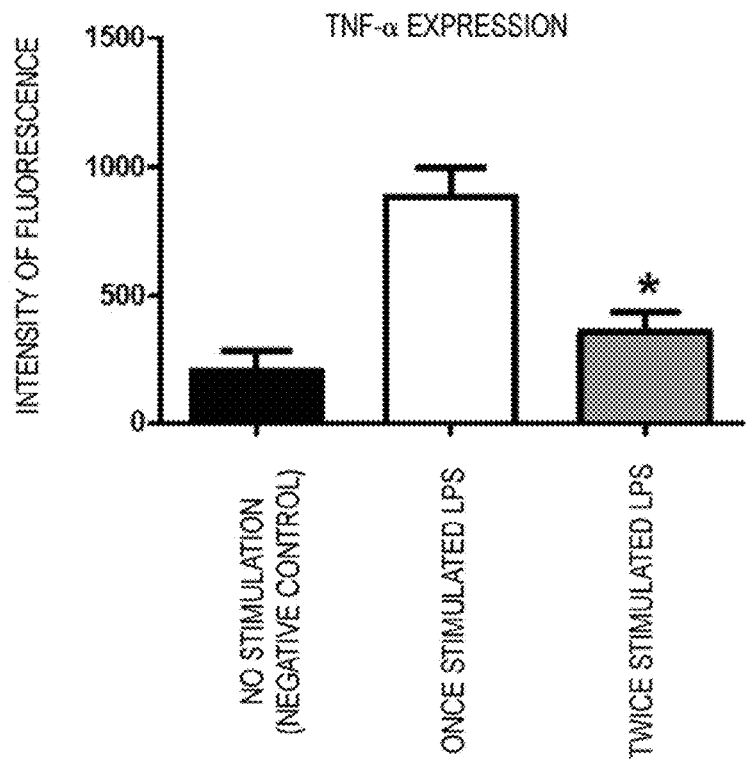
FIGS. 2A-2T respectively show the expression of the TNF alpha (A), IL-10 (B), HLA-DRA (C), CIITA (D), IRAK-M (E), ABIN-3 (F), LY64 (G), S100A9 (H), S100A8 (I), GBP1 (J), MMP7 (K), CXCL1 (L), CXCL10 (M), COX2 (N), FCN1 (O), TNFAIP6 (P), CXCL7 (Q), CXCL5 (R), PID1 (S) and RHOU (T) genes by PBMCs, which come from 6 healthy volunteers, stimulated by LPS and quantified by biochips after 45 hours. The y axis represents the intensity of fluorescence of each of the hybridisation probes: (A) 207113_s_at for TNF alpha; (B) 207433_at for IL-10; (C) 208894_at for HLA-DRA; (D) 205101_at for CIITA; (E) 213817_at for IRAK-M; (F) 220655_at for ABIN-3; (G) 206206_at for LY64; (H) 203535_at for S100A9; (I) 202917_s_at for S100A8; (J) 202269_x_at for GBP1; (K) 204259_at for MMP7; (L) 204470_at for CXCL1; (M) 204533_at for CXCL10; (N) 204748_at for COX2; (O) 205237_at for FCN1; (P) 206026_s_at for TNFAIP6; (Q) 214146_s_at for CXCL7; (R) 215101_s_at for CXCL5; (S)
Figure 2B:
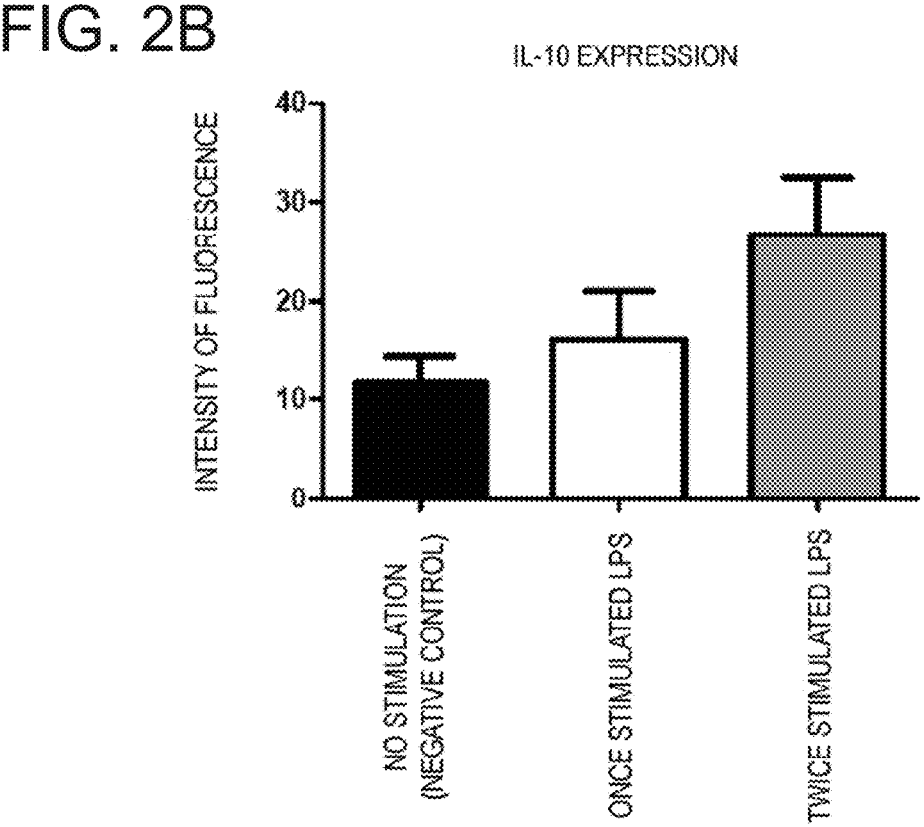
Figure 2C:
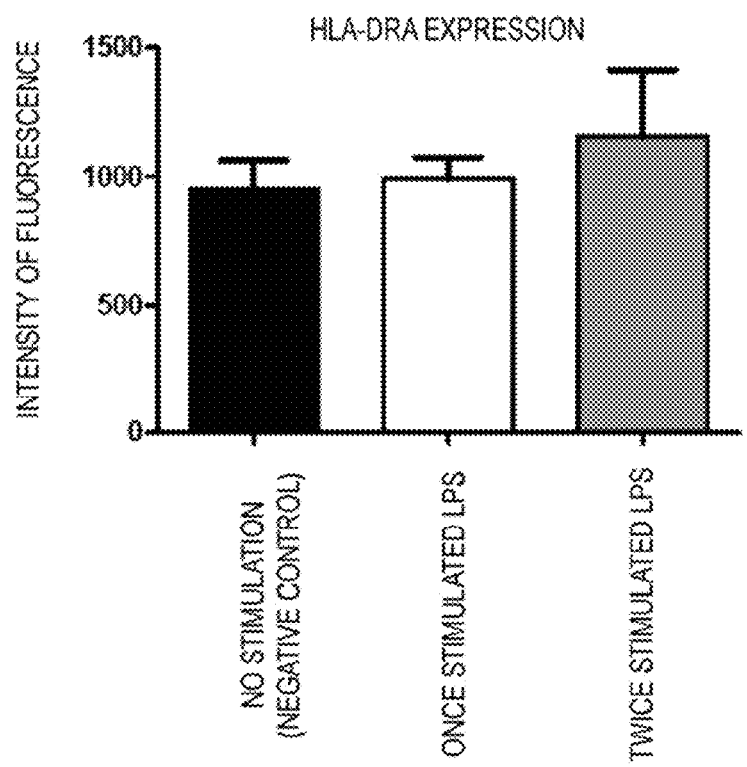
Figure 2D:
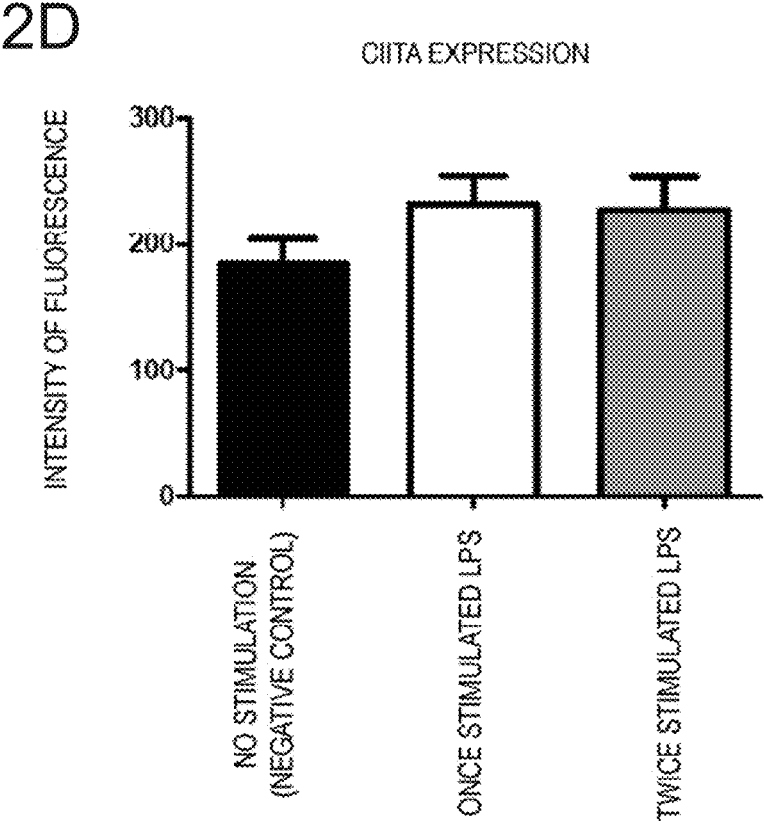
Figure 2E:
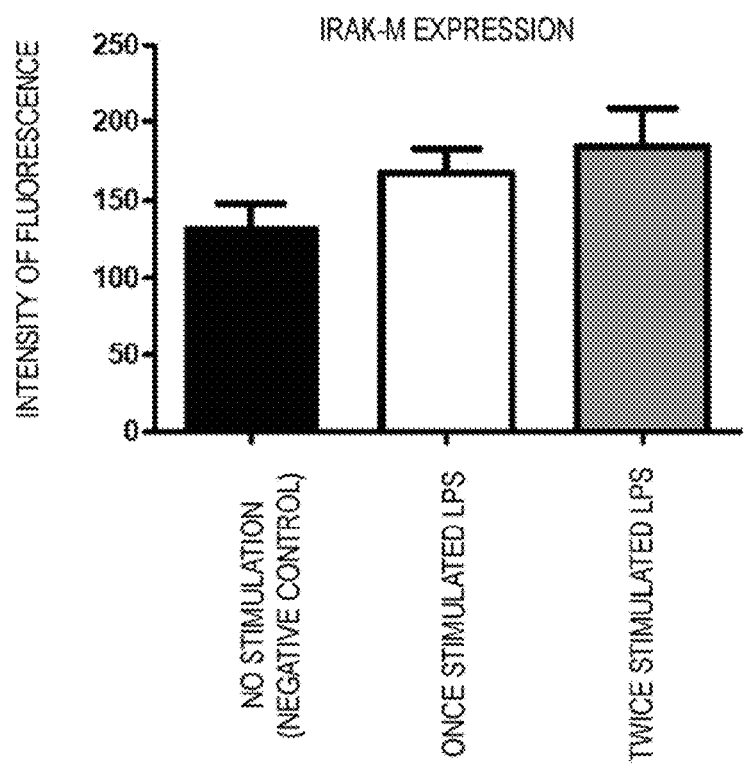
Figure 2F:
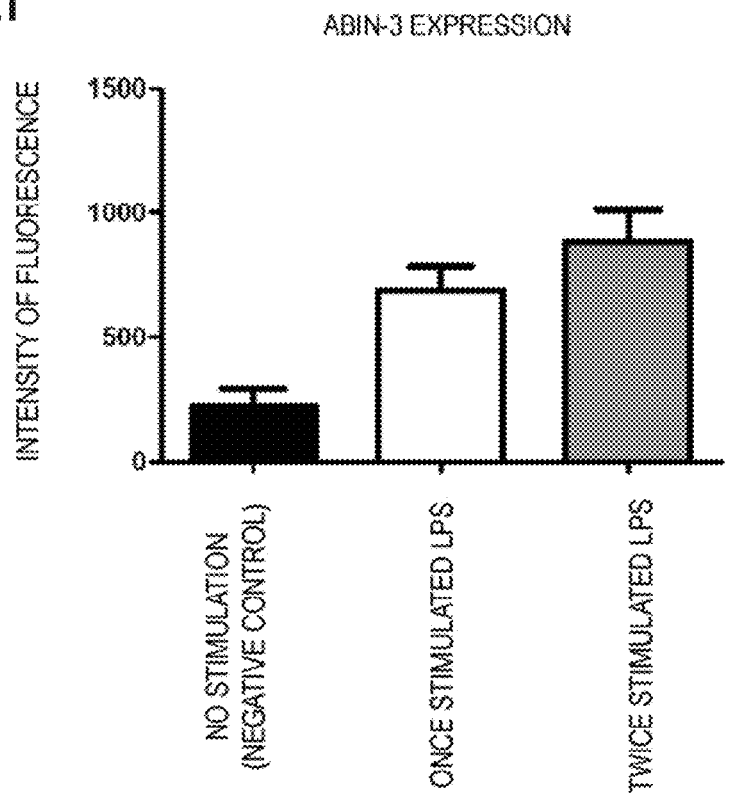
Figure 2G:
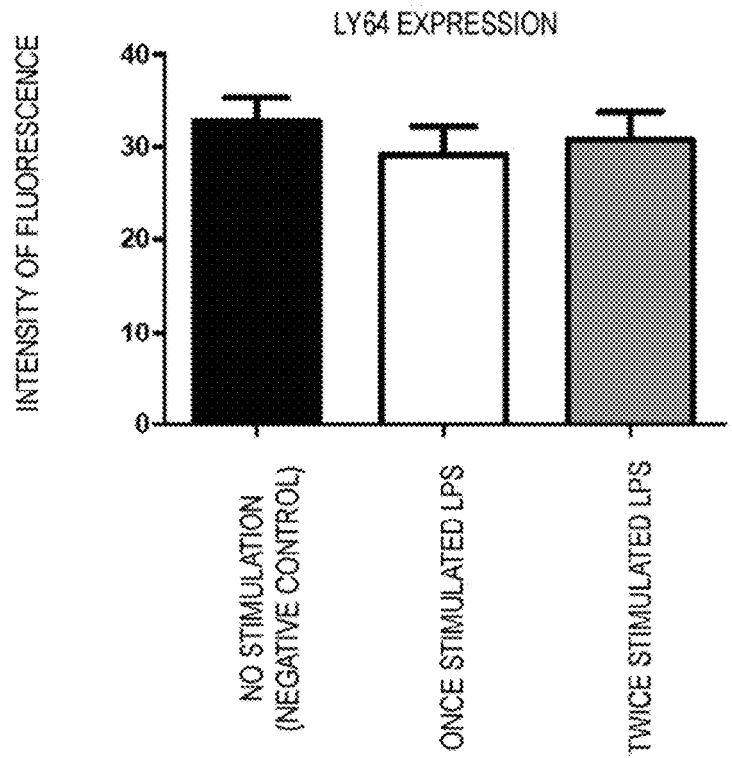
Figure 2H:
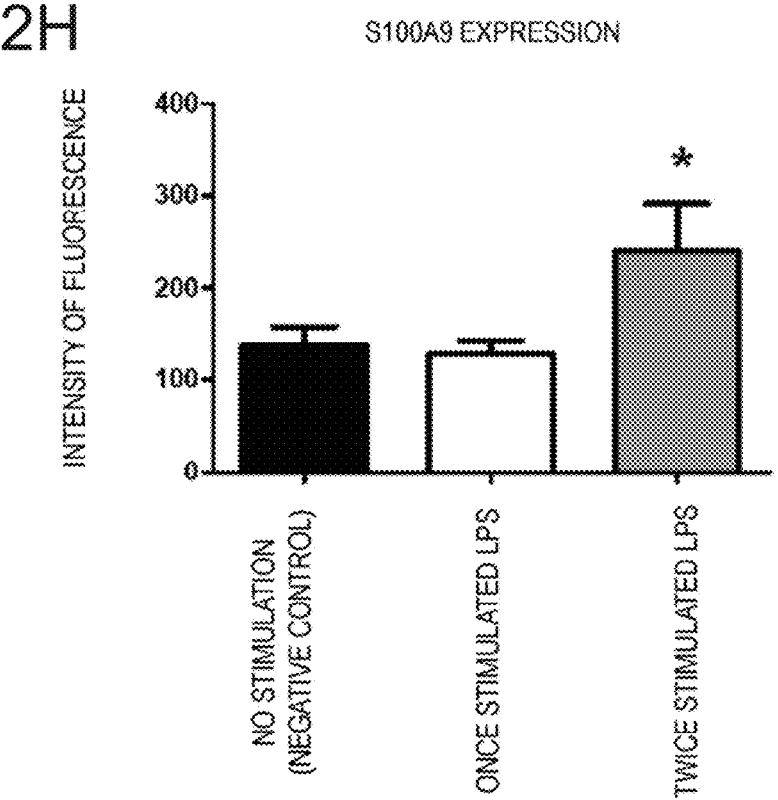
Figure 2I:
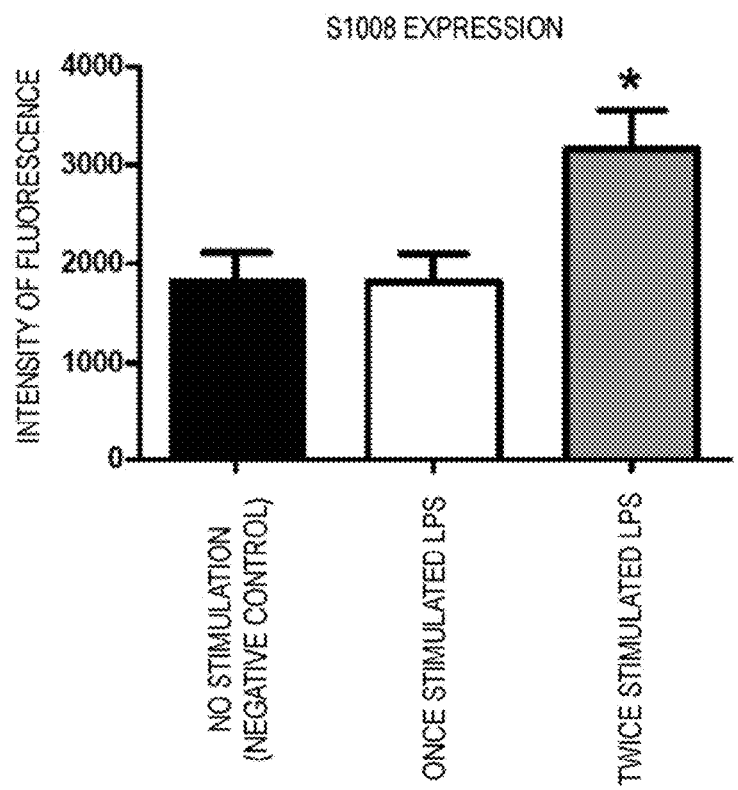
Figure 2J:
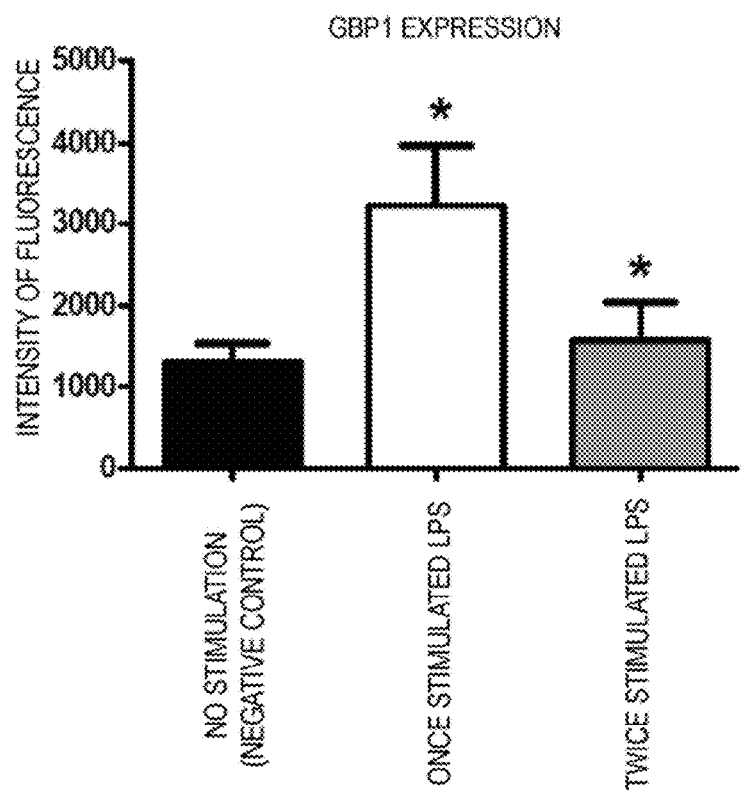
Figure 2K:
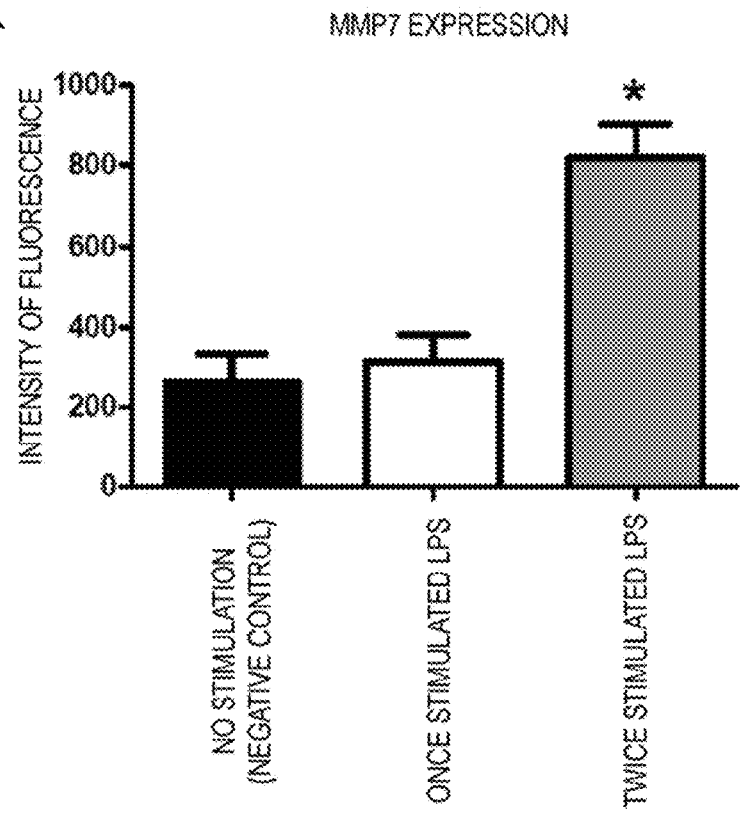
Figure 2L:
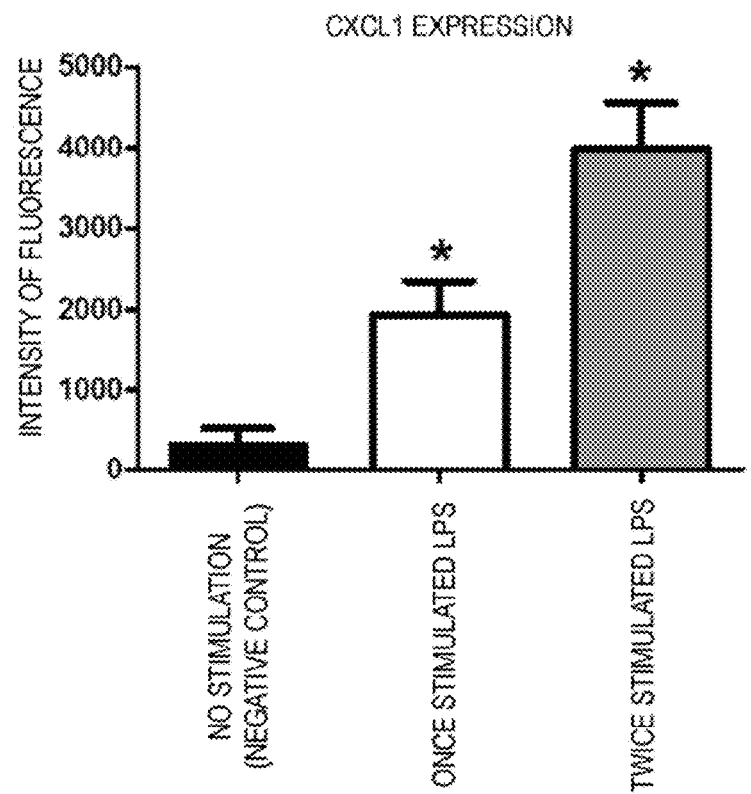
Figure 2M:
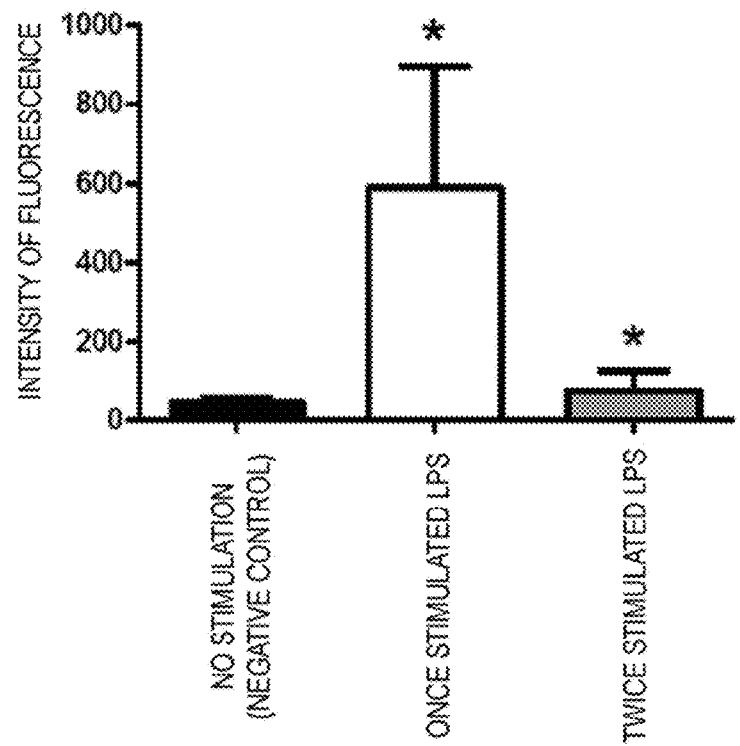
Figure 2N:
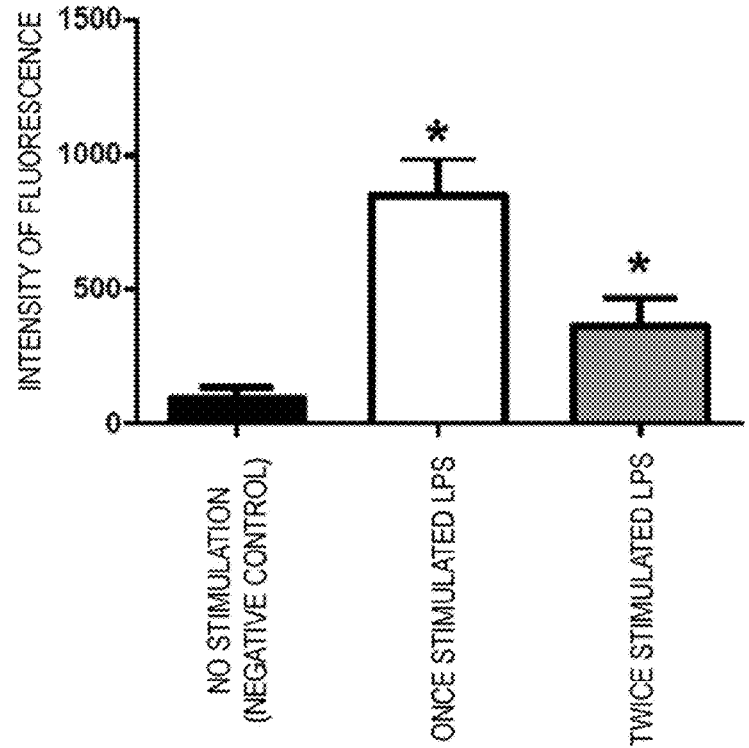
Figure 2O:
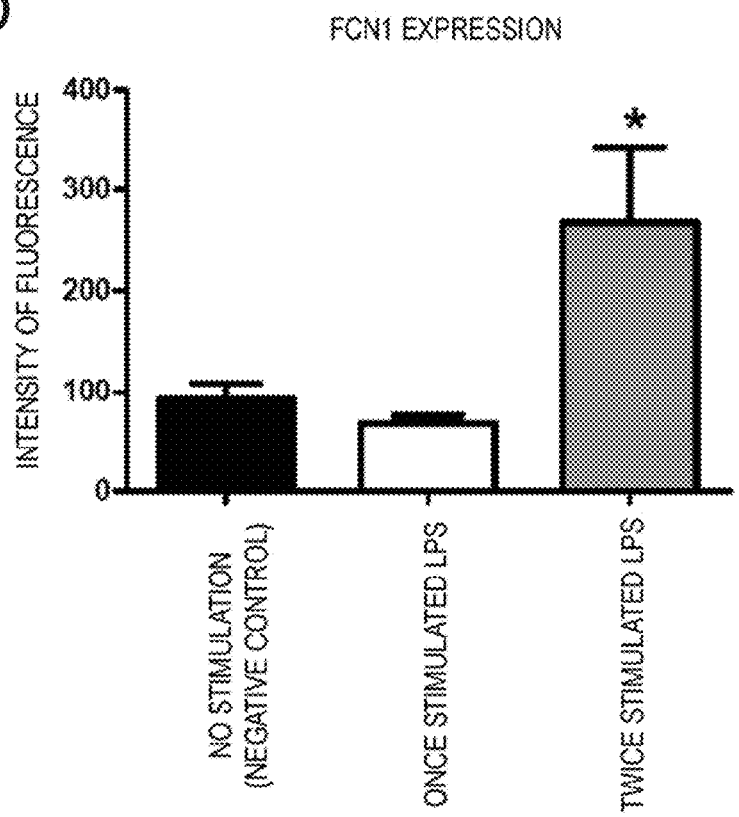
Figure 2P:
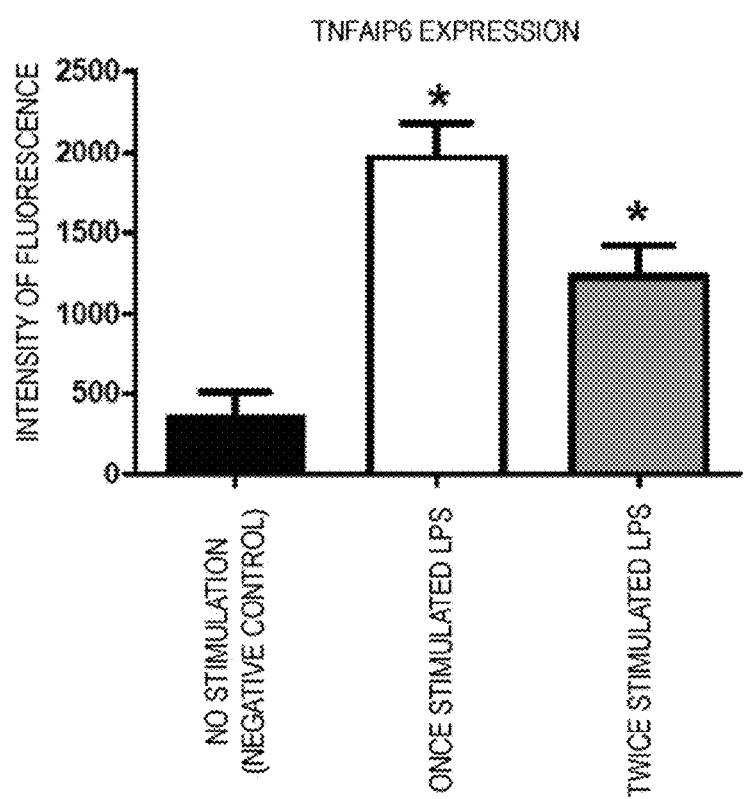
Figure 2Q:
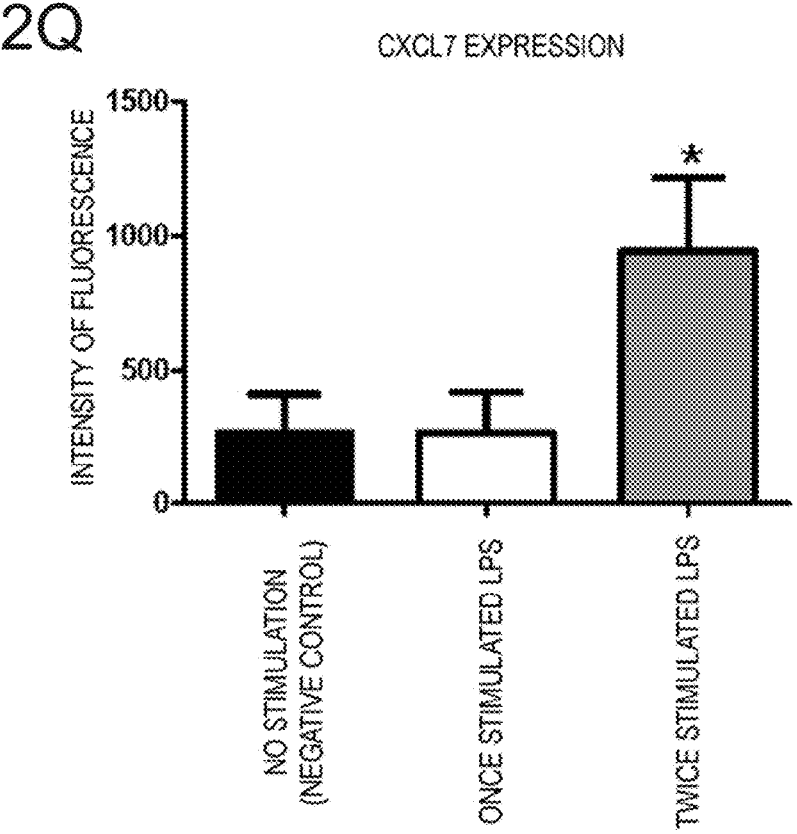
Figure 2R:
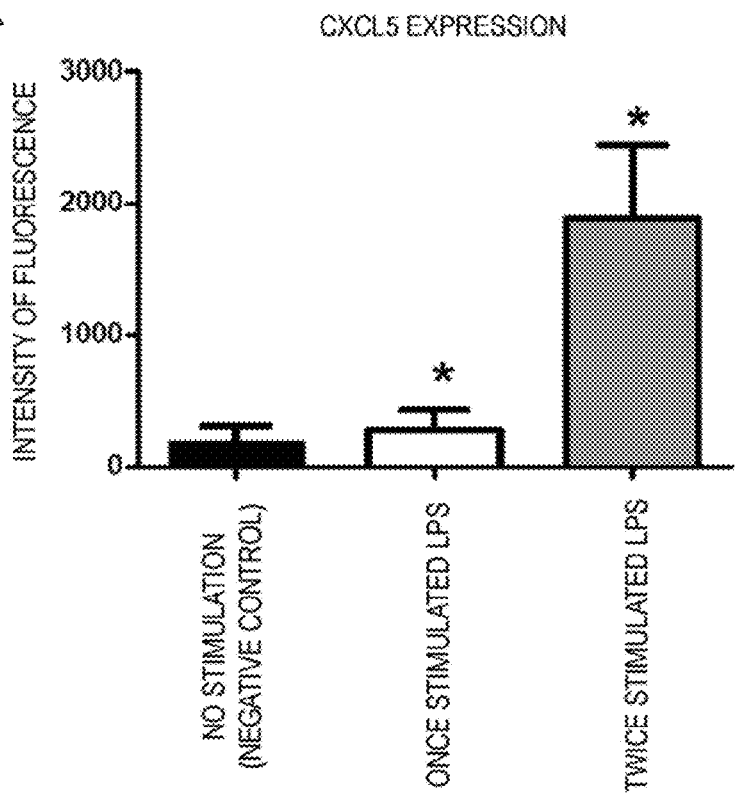
Figure 2S:
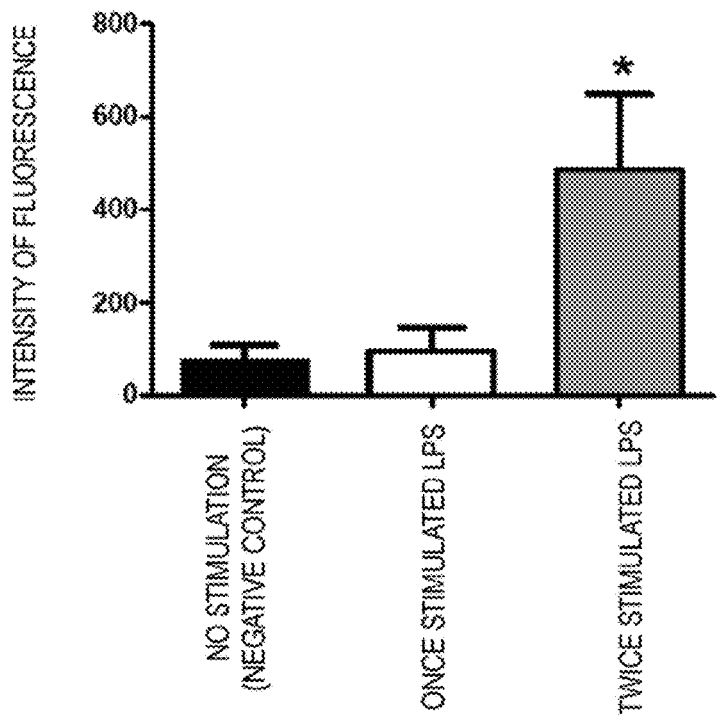
Figure 2T:
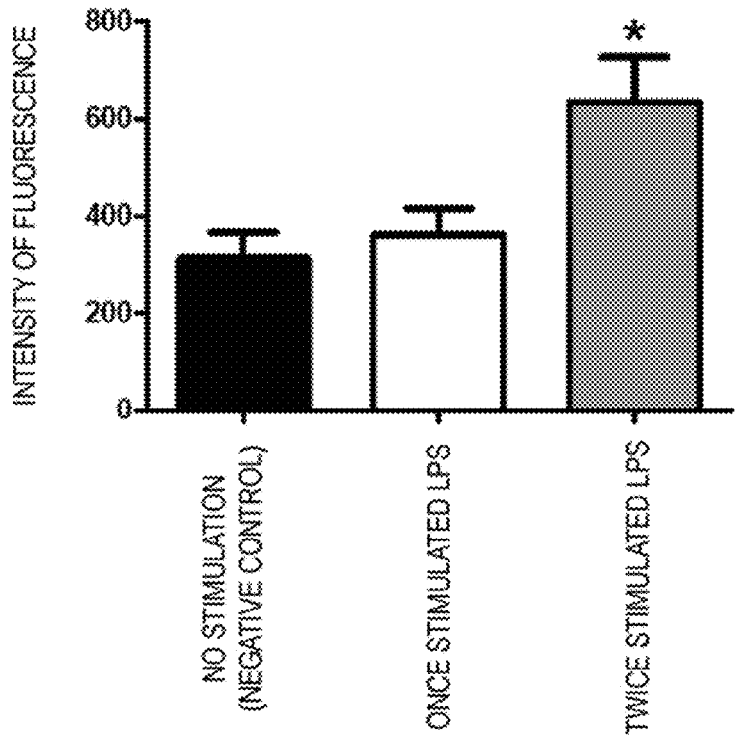

The ET models are characterised by a reduction of TNF-α production, associated with an increase in the secretion of IL-10 following a second stimulation by LPS. The production of these cytokines was therefore measured in the PBMC culturing supernatant following one or two stimulations by LPS. As shown in FIG. 1A, the cells stimulated twice by LPS produce low quantities of TNF-α (58.5±68.3 pg/mL) compared to cells stimulated only once (1208±594 pg/mL). However, as shown in FIG. 1B, these same cells secrete higher concentrations of IL-10 (63.2±58.2 pg/mL) compared to the cells stimulated once (8.4±6.9 pg/mL). In response to a second endotoxinic stimulation, the cells that are already stimulated release less TNF-α (58.5±68.3 pg/mL) than the cells stimulated only once (1208±594 pg/mL) and produce more IL-10 (63.2±58.2 vs. 8.4±6.9 pg/mL) than the cells stimulated once). These results are confirmed in the mRNA, since a significant decrease in the expression of TNF-α (FIG. 2A), coupled to an increase in the gene expression of IL-10 (FIG. 2B) in the cells stimulated twice by LPS were observed compared to PBMCs stimulated just once.

An analysis of the gene expression of PBMCs subjected to one or two stimulations with LPS was carried out on Affymetrix biochips. The genes with the greatest difference in expression between one or two stimulations with LPS ($p<0.05$ and expression difference $>2$), as well as genes known from the literature as being involved in this refractory state of ET or the immunosuppression phase induced by severe septic states are represented in FIG. 2. The second stimulation by bacterial endotoxin is accompanied by an increase in the mRNA expression of IL-10 (B), HLA-DRA (C), CIITA (D), IRAK-M (E), ABIN-3 (F) whereas the expression of TNF alpha (A) and LY64 (G) is decreased. The gene expression of the alarmins S100A9 (H) and S100A8 (I), of the chemokines CXCL1 (L), CXCL5 (R), and CXCL7 (Q), of MMP7 (K), FCN1 (O), PID1 (S) and RHOU (T) also increase following a second stimulation with LPS. Finally, the expression of the genes induced by interferon GBP1 (J) and CXCL10 (M), as well as of TNFAIP6 (P), decreases.

These data were then confirmed by qRT-PCR (FIG. 3) in which the same profile was obtained as that obtained on the biochips. In response to a second endotoxinic challenge, the inability to produce and express INF-α combined with the increase of IL-10 production and expression, of cells that have been exposed to a first dose of LPS, clearly indicates the development of an ET state.

Analysis of the Gene Expression in Patients in Septic Shock

In order to illustrate the clinical relevance of the model, the expression of these genes in patients in septic shock was studied respectively at the moment of diagnosis and 48 hours later. The expression of the genes was evaluated by an approach on biochip in a cohort of 19 patients described previously [9] and 9 healthy volunteers. As observed in the ET model, the results show an increase in the expression of IL-10, IRAK-M, CXCL7 and RHOU (FIGS. 4A, B, M and O) coupled to a reduction in the expression of Ly64, GBP1 and CXCL10 (FIGS. 4F, G and I) in patients in septic shock at the moment of diagnosis and even 48 hours later, compared to the healthy volunteers. In parallel, a slight reduction in the expression of INF-α is observed in the patients (FIG. 4E).

Overall, the clinical data confirm the mRNA changes observed ex vivo in the ET model, and underline the clinical relevance of this model.

IFN-γ and GM-CSF Significantly Improve the Production of TNF-α in the PBMCs Deactivated by LPS As shown in FIG. 1, the PBMCs stimulated one first time with LPS present a marked reduction of their INF-α production capacity in response to a second exposure to the endotoxin. Subsequently, it was investigated, in 7 successive trials, whether a 24-hour incubation in the presence of different immunomodulating drugs (IFN-γ, GM-CSF and Flt3-L) could restore this INF-α synthesis and reduce that of IL-10. IFN-γ and GM-CSF achieve this objective by inducing an increase in INF-α production (FIG. 5A). It is interesting to note that the drugs tested only impact on the reinforcement of the pro-inflammatory aspect, but still have no effect on the reduction of IL-10 production (FIG. 5B).

mRNA Monitoring of the Effect of the Immunostimulating Drugs During ET

Subsequently, in these same trials showing the beneficial effect of IFN-γ and GM-CSF on the restoration of INF-α synthesis in response to a second stimulation with LPS, the modulation of expression of a panel of genes was studied by biochips (FIG. 6) then validated by qRT-PCR (FIG. 7).

A significant induction of the mRNA expression of INF-α is observed in the presence of IFN-γ compared to the control values (FIG. 6A). The addition of the drugs induces a slight reduction in the mRNA expression of IL10 (FIG. 6B). In parallel, a significant increase in the gene expression of HLA-DRA and CIITA is observed when the cells pretreated with LPS are incubated with IFN-γ (FIG. 6C, 6D). With regard to the negative regulators of the LPS signalling path, the expression of ABIN-3 decreases significantly in the presence of IFN-γ (FIG. 6E, 6F). The expression of the LY64 and IRAKM genes also decreases in the presence of IFN-γ (FIG. 5G). The three drugs reduce the mRNA expression of the alarmins S100A9 and S100A8 (FIG. 6H, 6I). Furthermore, the presence of IFN-γ significantly increases the expression of the genes GBP1 (J), CXCL10 (M), COX 2 (N), TNFAIP6 (P) and significantly decreases that of MMP7 (K), CXCL1 (L), FCN1(O), CXCL7 (Q), CXCL5 (R), PID1 (S) and RHOU (T).

Effect of IFN-γ on the Whole Blood of Patients in Septic Shock

Figure 9A:
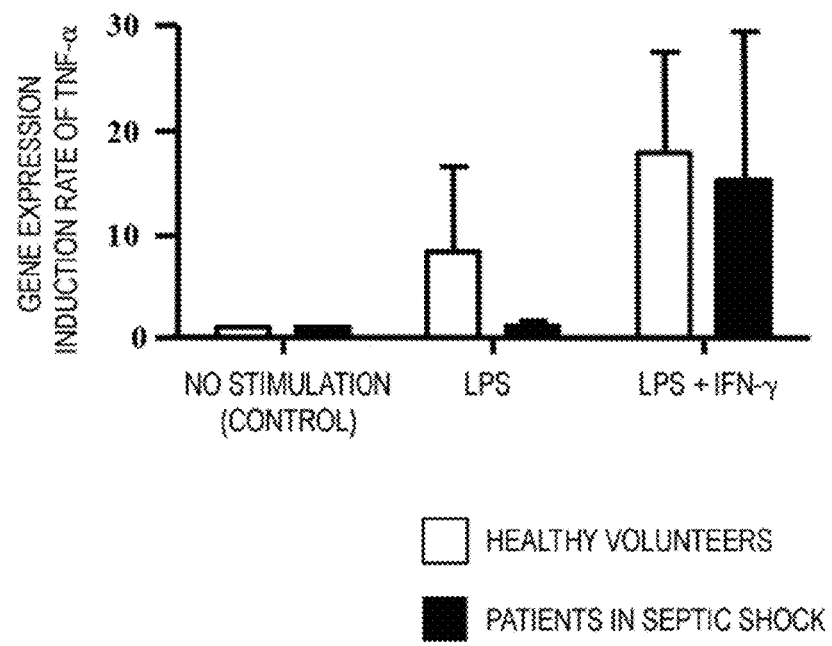
Figure 9B:
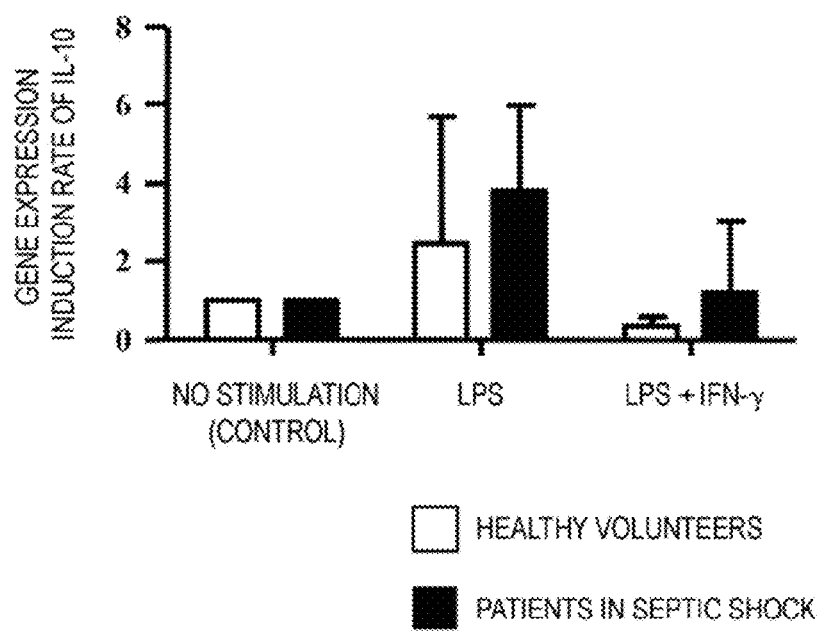
Figure 9C:
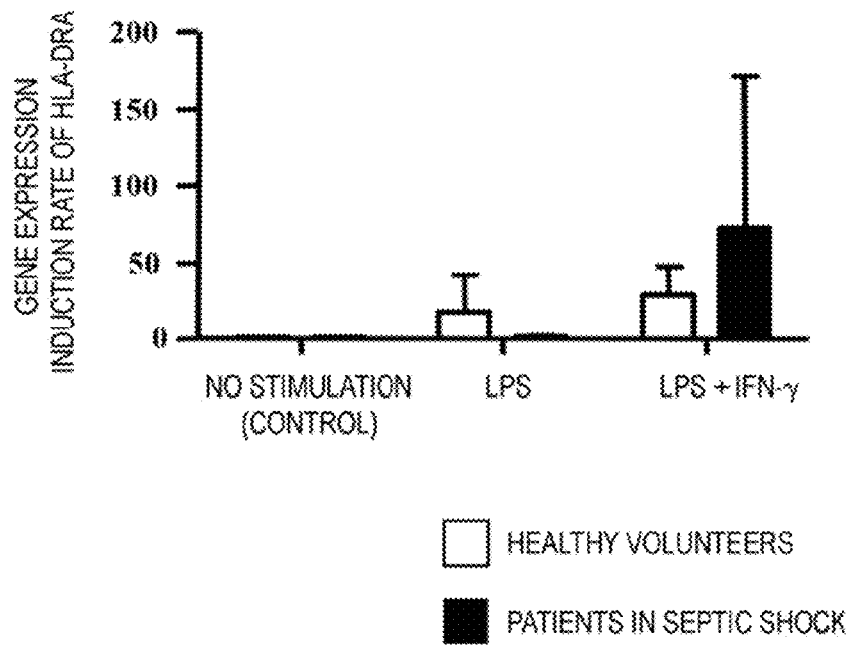
Figure 9D:
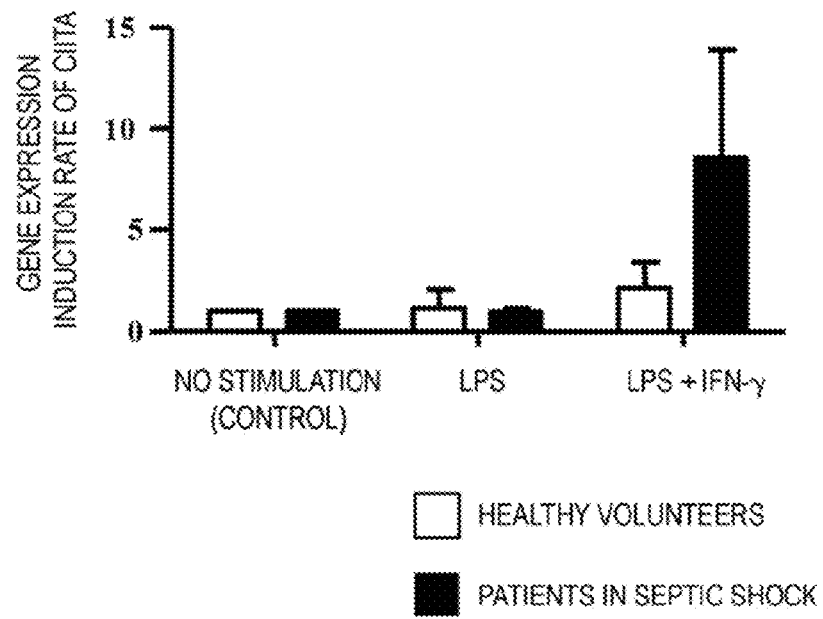
Figure 9E:
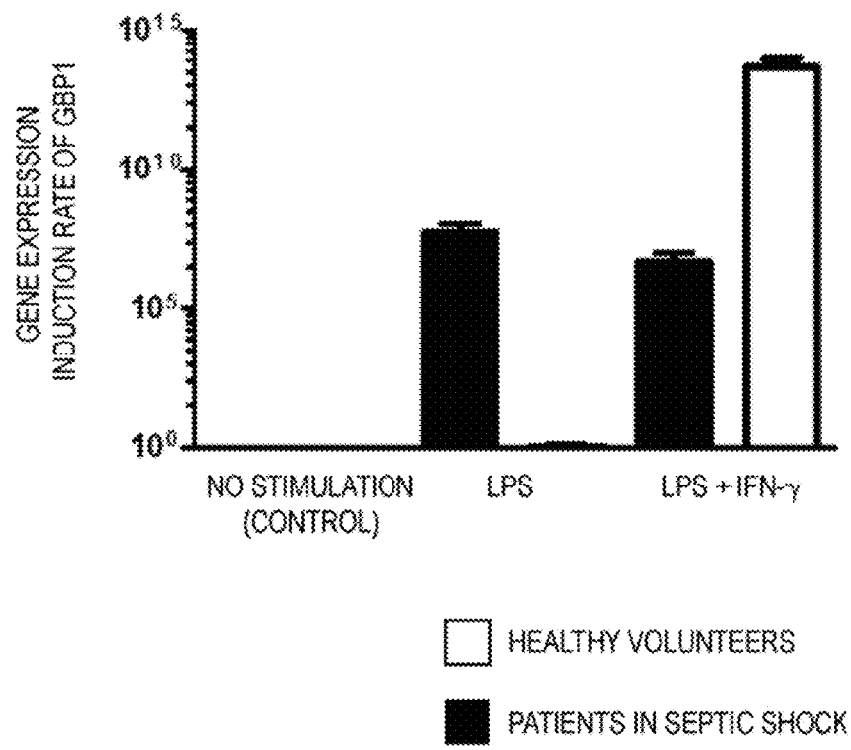
Figure 9F:
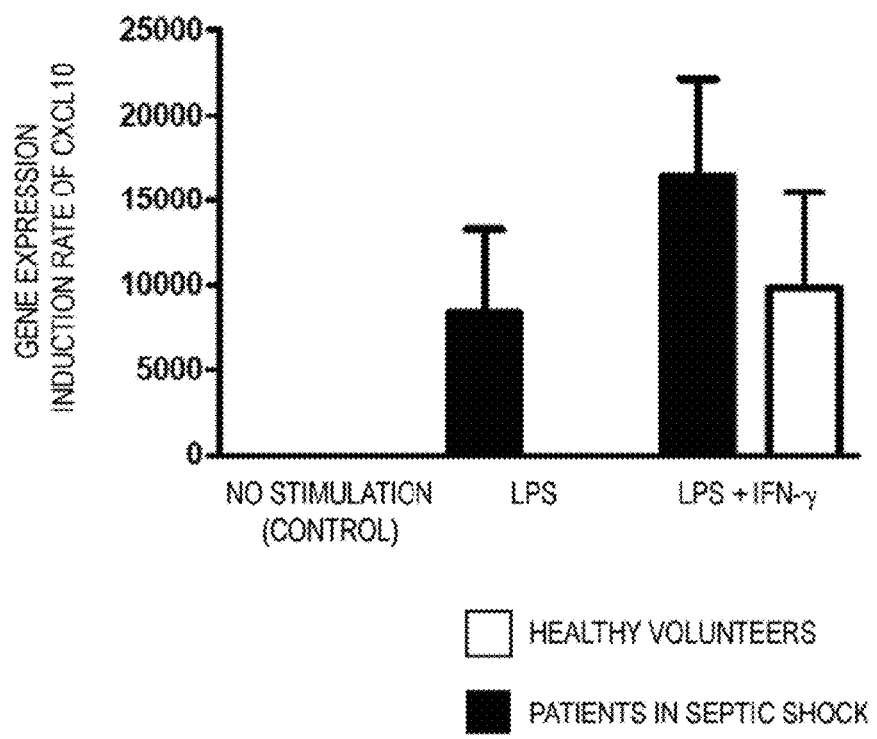
Figure 9G:
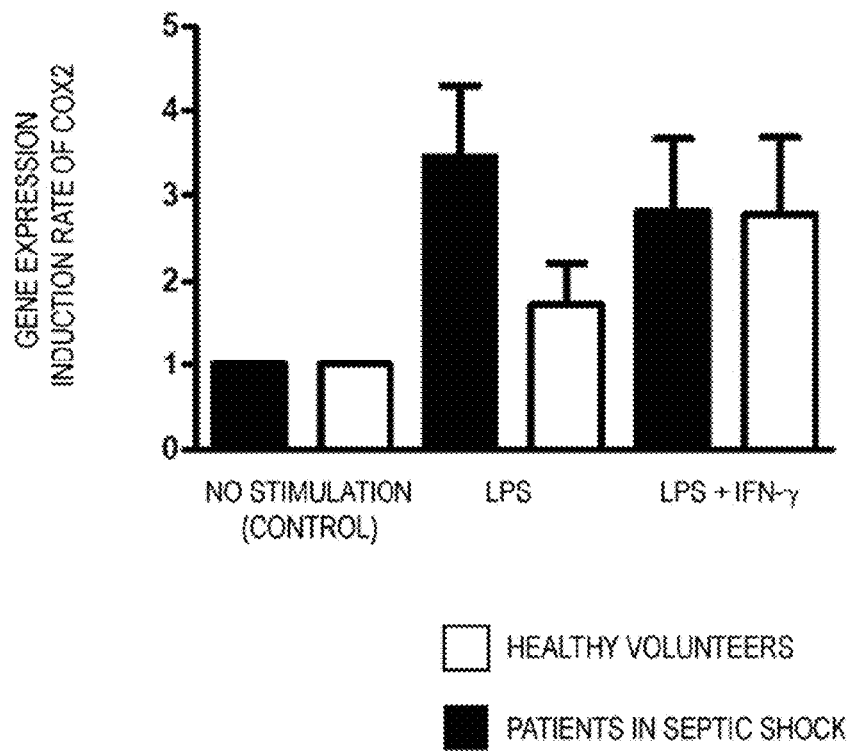
Figure 9H:
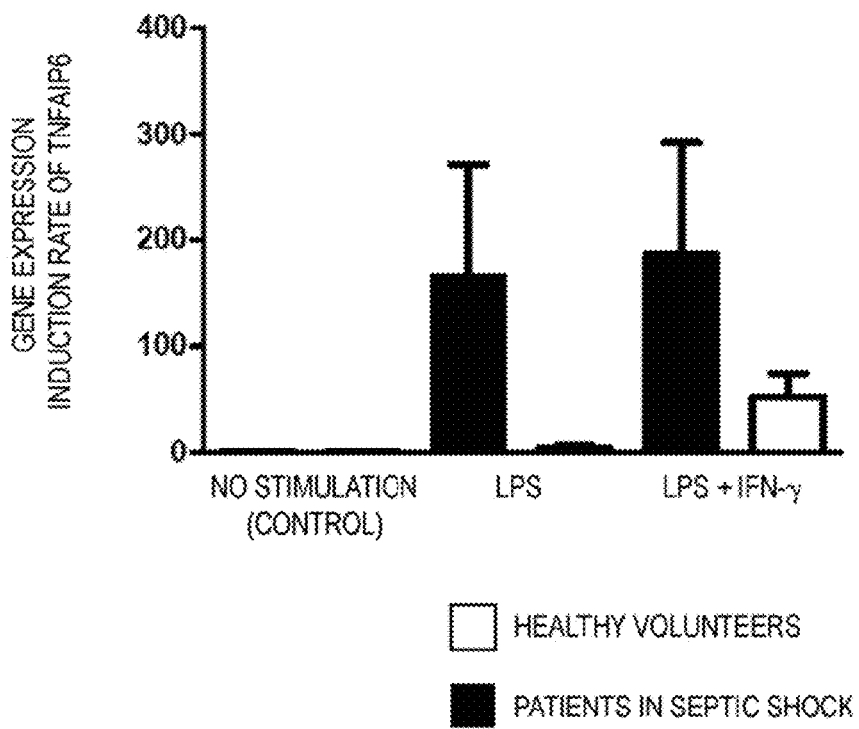

Finally, the results obtained were confirmed using whole blood of patients in septic shock. As expected, in response to a stimulation with LPS, the cells of patients produce less INF-α (FIG. 8A) and more IL-10 (FIG. 8B) than those of healthy volunteers, underlining the development of an ET state. The addition of IFN-γ totally restores the secretion of INF-α and completely inhibits the production of IL-10 in patients in septic shock. These protein results are confirmed with mRNA (FIG. 9A, B). Furthermore, the expression of GBP1 (FIG. 9E), of CXCL10 (FIG. 9F), of COX2 (FIG. 9G) and of TNFAIP6 (FIG. 9H) is very greatly reduced in the cells of patients following a stimulation with LPS relative to those of the healthy volunteers. The addition of IFN-γ restores the expression of these genes. In parallel, the cell of patients express much more CXCL5 (FIG. 9I) in response to a stimulation with LPS, and the expression of CXCL5 again becomes equivalent to that observed in the healthy donors after addition of IFN-γ. Finally, the gene expression of HLA-DRA and of CIITA also greatly increases in the patients in the presence of IFN-γ (FIG. 9C, D).

BIBLIOGRAPHIC REFERENCES

1. Kricka et al., Clinical Chemistry, 1999, No. 45(4), p.453-458.

2. Keller G. H. et al., DNA Probes, 2nd Ed., Stockton Press, 1993, sections 5 and 6, p.173-249.

3. Bustin SA *Journal of molecular endocrinology*, 2002, 29: 23-39.

4. Giulietti A Methods, 2001, 25: 386-401.

5. Nisonoff A. et al., 1960, Science, 132: 1770-1771).

6. Skerra A., 1993, Curr. Opin. Immunol., 5: 256-262).

7. Huston P. et al., 1988, Proc. Natl.Acad. Sci.USA, 85: 5879-5883.

8. Munoz C, J Clin Invest 1991.

9. Venet F, Shock 2010.

The invention claimed is:

1. A method comprising:
   a. obtaining a blood sample taken from an individual having Systemic Inflammatory Response Syndrome wherein the individual has undergone an immunomodulatory treatment,
   b. contacting the blood sample with reagents specific to products of expression of 5 to 21 target genes independently selected from the group consisting of: HLA-DR, CD, S100A9, S100A8, ABIN-3, IRAK-M, LY64, CIITA, TNF, IL-10, GBP1, MMP7, CXCL1, CXCL10, COX2, FCN1, TNFAIP6, CXCL7, CXCL5, PID1, and RHOU, and
   c. measuring expression levels of said 5 to 21 target genes in the blood sample.

2. The method according to claim 1, further comprising extracting peripheral blood mononuclear cells from the blood sample obtained in step a, and carrying out steps b. and c. on said peripheral blood mononuclear cells.

3. The method according to claim 1, wherein the reagents specific to the products of expression of the 5 to 21 target genes are selected from the group consisting of amplification primers, hybridization probes, and antibodies.

4. The method according to claim 1, further comprising administering an immunostimulant or an immunosuppressor to the individual.

5. The method according to claim 4, wherein the individual has a deregulated immune response.

6. The method according to claim 1, further comprising administering an immunostimulant or an immunosuppressor to the individual when the measured expression levels of said 5 to 21 target genes indicate that at least one component of the immune response of the individual is deregulated.

7. The method according to claim 1, wherein the individual has sepsis, severe sepsis, or septic shock.

8. A method comprising:
   a. obtaining a blood sample taken from an individual that is in septic shock wherein the blood sample is taken after the start of vasopressor treatment,
   b. contacting the blood sample with reagents specific to products of expression of 5 to 21 target genes independently selected from the group consisting of: HLA-DR, CD, S100A9, S100A8, ABIN-3, IRAK-M, LY64, CIITA, TNF, IL-10, GBP1, MMP7, CXCL1, CXCL10, COX2, FCN1, TNFAIP6, CXCL7, CXCL5, PID1, and RHOU, and
   c. measuring expression levels of said 5 to 21 target genes in the blood sample.

9. The method according to claim 8, further comprising extracting peripheral blood mononuclear cells from the blood sample obtained in step a., and carrying out steps b. and c. on said peripheral blood mononuclear cells.

10. The method according to claim 8, wherein the reagents specific to the products of expression of the 5 to 21 target genes are selected from the group consisting of amplification primers, hybridization probes, and antibodies.

11. The method according to claim 8, further comprising administering an immunostimulant or an immunosuppressor to the individual.

12. The method according to claim 11, wherein the individual has a deregulated immune response.

13. The method according to claim 8, further comprising administering an immunostimulant or an immunosuppressor to the individual when the measured expression levels of said 5 to 21 target genes indicate that at least one component of the immune response of the individual is deregulated.

* * * * *

SEQUENCE LISTING

<160> NUMBER OF SEQ ID NOS: 16

<210> SEQ ID NO 1
<211> LENGTH: 21
<212> TYPE: DNA
<213> ORGANISM: Artificial
<220> FEATURE:
<223> OTHER INFORMATION: Synthetic Construct - Amorce

<400> SEQUENCE: 1
aataaggttt ctcaaggggc t                                              21

<210> SEQ ID NO 2
<211> LENGTH: 22
<212> TYPE: DNA
<213> ORGANISM: Artificial
<220> FEATURE:
<223> OTHER INFORMATION: Synthetic Construct - Amorce

<400> SEQUENCE: 2
agaaccaaga cccagacatc aa                                             22

<210> SEQ ID NO 3
<211> LENGTH: 21
<212> TYPE: DNA
<213> ORGANISM: Artificial
<220> FEATURE:
<223> OTHER INFORMATION: Synthetic Construct - Amorce

<400> SEQUENCE: 3
gccaacctgg aaatcatgac a                                              21

<210> SEQ ID NO 4
<211> LENGTH: 19
<212> TYPE: DNA
<213> ORGANISM: Artificial
<220> FEATURE:
<223> OTHER INFORMATION: Synthetic Construct - Amorce

<400> SEQUENCE: 4
agggctgttc gtgagcaca                                                 19

<210> SEQ ID NO 5
<211> LENGTH: 21
<212> TYPE: DNA
<213> ORGANISM: Artificial
<220> FEATURE:
<223> OTHER INFORMATION: Synthetic Construct - Amorce

<400> SEQUENCE: 5
gctgggattc ctacacaatg c                                              21

<210> SEQ ID NO 6
<211> LENGTH: 24
<212> TYPE: DNA
<213> ORGANISM: Artificial
<220> FEATURE:
<223> OTHER INFORMATION: Synthetic Construct - Amorce

<400> SEQUENCE: 6
cgggttctga gtagagctca atct                                           24

<210> SEQ ID NO 7
<211> LENGTH: 20
<212> TYPE: DNA
<213> ORGANISM: Artificial

```
<220> FEATURE:
<223> OTHER INFORMATION: Synthetic Construct - Amorce

<400> SEQUENCE: 7
tttgaatgca gccagtctga                                               20

<210> SEQ ID NO 8
<211> LENGTH: 20
<212> TYPE: DNA
<213> ORGANISM: Artificial
<220> FEATURE:
<223> OTHER INFORMATION: Synthetic Construct - Amorce

<400> SEQUENCE: 8
gcattgctta tggagccaat                                               20

<210> SEQ ID NO 9
<211> LENGTH: 22
<212> TYPE: DNA
<213> ORGANISM: Artificial
<220> FEATURE:
<223> OTHER INFORMATION: Synthetic Construct - Amorce

<400> SEQUENCE: 9
gaattcccag ataaaagctt gt                                            22

<210> SEQ ID NO 10
<211> LENGTH: 19
<212> TYPE: DNA
<213> ORGANISM: Artificial
<220> FEATURE:
<223> OTHER INFORMATION: Synthetic Construct - Amorce

<400> SEQUENCE: 10
gacagtctgg tgggtgctc                                                19

<210> SEQ ID NO 11
<211> LENGTH: 20
<212> TYPE: DNA
<213> ORGANISM: Artificial
<220> FEATURE:
<223> OTHER INFORMATION: Synthetic Construct - Amorce

<400> SEQUENCE: 11
tcaaagagct ggtgcgaaaa                                               20

<210> SEQ ID NO 12
<211> LENGTH: 20
<212> TYPE: DNA
<213> ORGANISM: Artificial
<220> FEATURE:
<223> OTHER INFORMATION: Synthetic Construct - Amorce

<400> SEQUENCE: 12
aactcctcga agctcagctg                                               20

<210> SEQ ID NO 13
<211> LENGTH: 20
<212> TYPE: DNA
<213> ORGANISM: Artificial
<220> FEATURE:
<223> OTHER INFORMATION: Synthetic Construct - Amorce

<400> SEQUENCE: 13
atttccatgc cgtctacagg                                               20
```

```
<210> SEQ ID NO 14
<211> LENGTH: 20
<212> TYPE: DNA
<213> ORGANISM: Artificial
<220> FEATURE:
<223> OTHER INFORMATION: Synthetic Construct - Amorce

<400> SEQUENCE: 14
caccagaatg aggaactcct                                                   20

<210> SEQ ID NO 15
<211> LENGTH: 22
<212> TYPE: DNA
<213> ORGANISM: Artificial
<220> FEATURE:
<223> OTHER INFORMATION: Synthetic Construct - Amorce

<400> SEQUENCE: 15
gcattgagaa agaagccaac aa                                                22

<210> SEQ ID NO 16
<211> LENGTH: 21
<212> TYPE: DNA
<213> ORGANISM: Artificial
<220> FEATURE:
<223> OTHER INFORMATION: Synthetic Construct - Amorce

<400> SEQUENCE: 16
gaaaagtgtc ttcatgtatc c                                                 21
```